US007750144B2

(12) United States Patent
Zamore et al.

(10) Patent No.: US 7,750,144 B2
(45) Date of Patent: Jul. 6, 2010

(54) METHODS AND COMPOSITIONS FOR ENHANCING THE EFFICACY AND SPECIFICITY OF RNA SILENCING

(75) Inventors: Phillip D. Zamore, Northboro, MA (US); György Hutvágner, Worcester, MA (US); Dianne Schwarz, Westborough, MA (US); Martin Simard, Deschambault (CA)

(73) Assignee: University of Massachusetts, Boston, MA (US)

( * ) Notice: Subject to any disclaimer, the term of this patent is extended or adjusted under 35 U.S.C. 154(b) by 846 days.

(21) Appl. No.: 10/912,440

(22) Filed: Aug. 4, 2004

(65) Prior Publication Data

US 2005/0186586 A1    Aug. 25, 2005

Related U.S. Application Data

(63) Continuation-in-part of application No. 10/859,321, filed on Jun. 2, 2004.

(60) Provisional application No. 60/475,331, filed on Jun. 2, 2003, provisional application No. 60/507,928, filed on Sep. 30, 2003, provisional application No. 60/575,268, filed on May 28, 2004.

(51) Int. Cl.
*C07H 21/00* (2006.01)
*C07H 21/02* (2006.01)
*C07H 21/04* (2006.01)
*C12P 19/34* (2006.01)

(52) U.S. Cl. .................. 536/25.3; 536/24.5; 536/23.1; 435/91.1

(58) Field of Classification Search .................. None
See application file for complete search history.

(56) References Cited

U.S. PATENT DOCUMENTS

| 6,506,559 | B1 | 1/2003 | Fire et al. |
|---|---|---|---|
| 2002/0086356 | A1 | 7/2002 | Tuschl et al. |
| 2003/0108923 | A1 | 6/2003 | Tuschl et al. |
| 2004/0096843 | A1 | 5/2004 | Rossi et al. |
| 2004/0175703 | A1 | 9/2004 | Kreutzer et al. |
| 2004/0180351 | A1 | 9/2004 | Giese et al. |
| 2004/0192629 | A1 | 9/2004 | Xu et al. |
| 2004/0203145 | A1 | 10/2004 | Zamore et al. |
| 2004/0214198 | A1 | 10/2004 | Rana |
| 2004/0229266 | A1 | 11/2004 | Tuschl et al. |
| 2004/0248299 | A1 | 12/2004 | Jayasena et al. |
| 2004/0259247 | A1 | 12/2004 | Tuschl et al. |
| 2004/0259248 | A1 | 12/2004 | Tuschl et al. |
| 2005/0020521 | A1 | 1/2005 | Rana |
| 2005/0026278 | A1 | 2/2005 | Tuschl et al. |
| 2005/0037988 | A1 | 2/2005 | Zamore et al. |
| 2005/0059005 | A1 | 3/2005 | Tuschl et al. |
| 2005/0181382 | A1 | 8/2005 | Zamore et al. |
| 2005/0182005 | A1 | 8/2005 | Tuschl et al. |
| 2005/0186586 | A1 | 8/2005 | Zamore et al. |
| 2005/0227256 | A1 | 10/2005 | Zamore et al. |
| 2005/0227940 | A1 | 10/2005 | Rossi et al. |
| 2005/0234007 | A1 | 10/2005 | Tuschl et al. |
| 2005/0244858 | A1 | 11/2005 | Rossi et al. |
| 2005/0246794 | A1 | 11/2005 | Khvorova et al. |
| 2005/0256072 | A1 | 11/2005 | Aronin et al. |
| 2005/0273868 | A1 | 12/2005 | Rana |
| 2005/0277610 | A1 | 12/2005 | Rossi et al. |
| 2006/0009402 | A1 | 1/2006 | Zamore et al. |
| 2006/0069050 | A1 | 3/2006 | Rana |
| 2006/0134787 | A1 | 6/2006 | Zamore et al. |
| 2006/0166910 | A1 | 7/2006 | Tuschl et al. |
| 2006/0178334 | A1 | 8/2006 | Rossi et al. |
| 2006/0212950 | A1 | 9/2006 | Tuschl et al. |
| 2007/0003960 | A1 | 1/2007 | Tuschl et al. |
| 2007/0003961 | A1 | 1/2007 | Tuschl et al. |
| 2007/0003962 | A1 | 1/2007 | Tuschl et al. |
| 2007/0003963 | A1 | 1/2007 | Tuschl et al. |
| 2007/0031844 | A1 | 2/2007 | Khvorova et al. |
| 2007/0039072 | A1 | 2/2007 | Khvorova et al. |
| 2007/0093445 | A1 | 4/2007 | Tuschl et al. |
| 2007/0104688 | A1 | 5/2007 | Rossi et al. |
| 2007/0111228 | A1 | 5/2007 | Jayasena et al. |
| 2007/0207974 | A1 | 9/2007 | Khvorova et al. |
| 2007/0265220 | A1 | 11/2007 | Rossi et al. |

FOREIGN PATENT DOCUMENTS

CA          2432341 A1     7/2002

(Continued)

OTHER PUBLICATIONS

Opalinska, et al. (2006) Nucleic Acid Therapeutics for Hematologic Malignancies—Theoretical Considerations. Ann. N.Y. Acad. Sci., v.1082:124-136.*
Opalinska and Gewirtz. (2002) Nucleic-Acid Therapeutics: Basic Principles and Recent Applications. Nature Reviews Drug Discovery, v.1:503-514.*
McManus, et al. (2002) Gene Silencing in Mammals by Small Interfering RNAS. Nature Reviews Genetics, v.3:737-47.*
Bartel DP. MicroRNAs: genomics, biogenesis, mechanism, and function. Cell. Jan. 23, 2004;116(2):281-97.
Boden D, Pusch O, Lee F, Tucker L, Ramratnam B. Efficient gene transfer of HIV-1-specific short hairpin RNA into human lymphocytic cells using recombinant adeno-associated virus vectors. Mol Ther. Mar. 2004;9(3):396-402.

(Continued)

*Primary Examiner*—Tracy Vivlemore
*Assistant Examiner*—Jennifer Pitrak
(74) *Attorney, Agent, or Firm*—Lahive & Cockfield, LLP; Debra J. Milasincic, Esq.; James H. Velema, Esq.

(57) ABSTRACT

The present invention provides methods of enhancing the efficacy and specificity of RNA silencing. The invention also provides compositions for mediating RNA silencing. In particular, the invention provides siRNAs, siRNA-like molecules, shRNAs, vectors and transgenes having improved specificity and efficacy in mediating silencing of a target gene. Therapeutic methods are also featured.

36 Claims, 33 Drawing Sheets

FOREIGN PATENT DOCUMENTS

| | | |
|---|---|---|
| CA | 2432350 A1 | 7/2002 |
| DE | 10160151 A1 | 6/2003 |
| EP | 1389637 A1 | 2/2004 |
| EP | 1527176 B1 | 5/2005 |
| EP | 1857547 A2 | 11/2007 |
| WO | WO-02/44321 A2 | 6/2002 |
| WO | WO-02/055692 A2 | 7/2002 |
| WO | WO-02/055693 A2 | 7/2002 |
| WO | WO-03/020931 A2 | 3/2003 |
| WO | WO-03/035869 A1 | 5/2003 |
| WO | WO-03/068797 A1 | 8/2003 |
| WO | WO-2004/015107 A2 | 2/2004 |
| WO | WO-2004/029212 A2 | 4/2004 |
| WO | WO-2004/045543 A2 | 6/2004 |
| WO | WO-2004/046324 A2 | 6/2004 |
| WO | WO-2005/001043 A2 | 1/2005 |
| WO | WO-2005062937 A3 | 7/2005 |
| WO | WO-2005/069987 A2 | 8/2005 |
| WO | WO-2005/079532 A2 | 9/2005 |
| WO | WO-2005/079533 A2 | 9/2005 |
| WO | WO-2005/089287 A2 | 9/2005 |
| WO | WO-2006015389 A2 | 2/2006 |

OTHER PUBLICATIONS

Boden D, Pusch O, Silbermann R, Lee F, Tucker L, Ramratnam B. Enhanced gene silencing of HIV-1 specific siRNA using microRNA designed hairpins. Nucleic Acids Res. Feb. 13, 2004;32(3):1154-8.

Bonnet E, Wuyts J, Rouze P, Van De Peer Y. Evidence that microRNA precursors, unlike other non-coding RNAs, have lower folding free energies than random sequences. Bioinformatics. Jun. 24, 2004.

Chi JT, Chang HY, Wang NN, Chang DS, Dunphy N, Brown PO. Genomewide view of gene silencing by small interfering RNAs. Proc Natl Acad U S A. May 27, 2003;100(11):6343-6.

Dharmacon RNA Technologies. Products for RNA Interference. Company brochure.

Dharmacon RNA Technologies. On-Target siRNA. Company Brochure.

Doench JG, Petersen CP, Sharp PA. siRNAs can function as miRNAs. Genes Dev. Feb. 15, 2003;17(4):438-42.

Haley B, Zamore PD. Kinetic analysis of the RNAi enzyme complex. Nat Struct Mol Biol. Jul. 2004;11(7):599-606.

Holen T, Amarzguioui M, Babaie E, Prydz H. Similar behaviour of single-strand and double-strand siRNAs suggests they act through a common RNAi pathway. Nucleic Acids Res. May 1, 2003;31(9):2401-7.

Jackson AL, Bartz SR, Schelter J, Kobayashi SV, Burchard J, Mao M, Li B, Cavet G, Linsley PS. Expression profiling reveals off-target gene regulation by RNAi. Nat Biotechnol. Jun. 2003;21(6):635-7.

Ketting RF, Fischer SE, Bernstein E, Sijen T, Hannon GJ, Plasterk RH. Dicer functions in RNA interference and in synthesis of small RNA involved in developmental timing in C. elegans. Genes Dev. Oct. 15, 2001;15(20):2654-9.

Khvorova A, Reynolds A, Jayasena SD. Functional siRNAs and miRNAs exhibit strand bias. Cell. Oct. 17, 2003;115(2):209-16.

Krol J, Sobczak K, Wilczynska U, Drath M, Jasinska A, Kaczynska D, Krzyzosiak WJ. Structural Features of MicroRNA (miRNA) Precursors and Their Relevance to miRNA Biogenesis and Small Interfering RNA/Short Hairpin RNA Design. J Biol Chem. Oct. 1, 2004;279(40):42230-9. Epub Aug. 2, 2004.

Lai EC. Micro RNAs are complementary to 3' UTR sequence motifs that mediate negative post-transcriptional regulation. Nat Genet. Apr. 2002;30(4):363-4.

Mallory AC, Reinhart BJ, Jones-Rhoades MW, Tang G, Zamore PD, Barton MK, Bartel DP. MicroRNA control of Phabulosa in leaf development: importance of pairing to the microRNA 5' region. EMBO J. Aug. 18, 2004;23(16):3356-64. Epub Jul. 29, 2004.

Martinez J, Patkaniowska A, Urlaub H, Luhrmann R, Tuschl T. Single-stranded antisense siRNAs guide target RNA cleavage in RNAi. Cell. Sep. 6, 2002;110(5):563-74.

McManus MT, Petersen CP, Haines BB, Chen J, Sharp PA. Gene silencing using micro-RNA designed hairpins. RNA. Jun. 2002;8(6):842-50.

Meister G, Landthaler M, Dorsett Y, Tuschl T. Sequence-specific inhibition of microRNA- and siRNA-induced RNA silencing. RNA. Mar. 2004;10(3):544-50.

Murchison EP, Hannon GJ. miRNAs on the move: miRNA biogenesis and the RNAi machinery. Curr Opin Cell Biol. Jun. 2004;16(3):223-9.

Nykanen A, Haley B, Zamore PD. ATP requirements and small interfering RNA structure in the RNA interference pathway. Cell. Nov. 2, 2001;107(3):309-21.

Pusch O, Boden D, Silbermann R, Lee F, Tucker L, Ramratnam B. Nucleotide sequence homology requirements of HIV-1-specific short hairpin RNA. Nucleic Acids Res. Nov. 15, 2003;31(22):6444-9.

Reynolds A, Leake D, Boese Q, Scaringe S, Marshall WS, Khvorova A. Rational siRNA design for RNA interference. Nat Biotechnol. Mar. 2004;22(3):326-30.

Schwarz DS, Hutvagner G, Du T, Xu Z, Aronin N, Zamore PD. Asymmetry in the assembly of the RNAi enzyme complex. Cell. Oct. 17, 2003;115(2):199-208.

Schwarz DS, Zamore PD. Why do miRNAs live in the miRNP? Genes Dev. May 1, 2002;16(9)1025-31.

Schwarz DS, Tomari Y, Zamore PD. The RNA-induced silencing complex is a $Mg^{2+}$- dependent endonuclease. Curr Biol. May 4, 2004;14(9):787-91.

Semizarov D, Frost L, Sarthy A, Kroeger P, Halbert DN, Fesik SW. Specificity of short interfering RNA determined through gene expression signatures. Proc Nati Acad Sci U S A. May 27, 2003;100(11):6347-52.

Tang G, Zamore PD. Biochemical dissection of RNA silencing in plants. Methods Mol Biol. 2004;257:223-44.

Tomari Y, Du T, Haley B, Schwarz DS, Bennett R, Cook HA, Koppetsch BS, Theurkauf WE, Zamore PD. RISC assembly defects in the Drosophila RNAi mutant armitage. Cell. Mar. 19, 2004;116(6):831-41.

Vargason JM, Szittya G, Burgyan J, Tanaka Hall TM. Size selective recognition of siRNA by an RNA silencing suppressor. Cell. Dec. 26, 2003;115(7):799-811.

Hohjoh, H., "Enhancement of RNAi activity by improved siRNA duplexes," *FEBS Letters*, vol. 557(1-3):193-198 (2004).

Invitation to Pay Additional Fees for Application No. PCT/US2005/029011, dated Feb. 20, 2006.

Amarzguioui, Mohammed et al., "Tolerance for mutations and chemical modifications in a siRNA," *Nucleic Acids Research*, vol. 31(2):589-595 (2003).

Czaudema, Frank et al., "Structural variations and stabilising modifications of synthetic siRNAs in mammalian cells," *Nucleic Acids Research*, vol. 31(11):2705-2716 (2003).

Parrish, Susan et al., "Functional Anatomy of a dsRNA Trigger: Differential Requirement for the Two Trigger Strands in RNA Interference," *Molecular Cell*, vol. 6:1077-1087 (2000).

Written Opinion and International Search Report for Application No. PCT/US2005/029011, dated Apr. 13, 2006.

Invitation to Pay Additional Fees for Application No. PCT/US2005/029011, dated Feb. 20, 2006.

European Search Report for Application No. 04753972.1-2402, dated Oct. 31, 2006.

Akhtar, S et al., "Nonviral delivery of synthetic siRNAs in vivo", The Journal of Clinical Investigation. 117(12):3623-3632 (2007).

Bumcrot, David et al., "RNAi therapeutics: a potential new class of pharmaceutical drugs", Nature Chemical Biology. 2(12): 711-719 (2006).

Corey, David R. et al., "Chemical modification: the key to clinical application of RNA interference?" The Journal of Clinical Investigation. 117(12): 3615-3622 (2007).

Doench, John G. et al., "Specificity of microRNA target selection in translational repression," *Genes & Development*, 2004:504-511 (2004).

Gerwitz, Alan M. "On future's doorstep: RNA interference and the pharmacopeia of tomorrow", The Journal of Clinical Investigation. 117(12): 3612-3614 (2007).

Grimm D and Kay MA. "Therapeutic application of RNAi: is mRNA targeting finally ready for prime time?" *The Journal of Clinical Investigation*. 117(12): 3633-3641 (2007).

Grzelinski, Marius et al, "RNA Interference-Mediated Gene Silencing of Pleiotrophin Through Polyethylenimine-Complexed Small Interfering RNAs In Vivo Exerts Antitumoral Effects in Glioblastoma Xenografts," *Human Gene Therapy*, 17:751-766 (2006).

Hu-Lieskovan, Siwen et al, "Sequence-Specific Knockdown of EWS-FLI1 by Targeted, Nonrival Delivery of Small Interfering RNA Inhibits Tumor Growth in a Murine Model of Metastatic Ewing's Sarcoma," *Cancer Research*, 65:(19) 8984-8992 (2005).

Kim, DH and Rossi, JJ, "Strategies for silencing human disease using RNA interference", *Nature Reviews Genetics*, 8: 173-184 (2007).

Li, Bao-jian et al, "Using siRNA in Pophylactic and Therapeutic Regimens Against SARS Coronavirus in Rhesus Macaque," *Nature Medicine*, vol. 11:9, 944-951 (2005).

Reich, Samuel J. et al., "Small Interfering RNA (siRNA) targeting VEGF Effectively Inhibits Ocular Neovascularization in a Mouse Model," *Molecular Vision*, vol. 9, 210-216 (2003).

Soutschek, Jurgen et al, "Therapeutic Silencing of an Endogenous Gene by Systemic Administration of Modified si RNAs," *Nature Publishing Group*, vol. 432, 173-178 (2004).

Tan, P. H. et al, "Gene Knockdown with Intrathecal siRNA of NMDA Receptor NR2B Subunit Reduces Formalin-induced Nocicéstion in the Rat," *Gene Therapy*, vol. 12, 59-66 (2005).

Thakker, Deepak R. et al, "Neurochemical and Behavioral Consequences of Widespred Gene Knockdown in the Adult Mouse Brain by Using Nonrival Interference," *PNAS*, vol. 101:49, 17270-17275 (2004).

Zhang, Yingjie et al, "Engineering Mucosal RNA Interference in Vivo," *Molecular Therapy*, vol. 14:3, 336-342 (2006).

Zimmermann, Tracy S. et al, "RNAi-mediated Gene Silencing in Non-human Primates," *Nature*, vol. 441, 111-114 (2006).

Ambros, Victor et al., "MicroRNAs and Other Tiny Endogenous RNAs in *C. elegans*," *Current Biology*, vol. 13:807-818 (2003).

Aravin, Alexei A. et al., "The Small RNA Profile during *Drosophila melanogaster* Development," *Development Cell*, vol. 5:337-350 (2003).

Bernstein, Emily et al., "Role for a bidentate ribonuclease in the initiation step of RNA interference," *Nature*, vol. 409:363-366 (2001).

Boutla, Alexandra et al., "Development defects by antisense-mediated inactivation of micro-RNAs 2 and 13 in Drosophila and the identification of putative target genes," *Nucleic Acids Research*, vol. 31(17):4973-4980 (2003).

Brennecke, Julius et al., "*bantam* Encodes a Developmentally Regulated microRNA that Controls Cell Proliferation and Regulates the Proapoptotic Gene hid in *Drosophila*," *Cell*, vol. 113:25-36 (2003).

Brennecke, Julius et al., "Towards a complete description of the microRNA complement of animal genomes," *Genome Biology*, vol. 4:228-228.3 (2003).

Caplen, Natasha J. et al., "dsRNA-mediated gene silencing in the cultured *Drosophila* cells: a tissue culture model for the analysis of RNA interference," *Gene*, vol. 252:95-105 (2000).

Caplen, Natasha J. et al., "Specific inhibition of gene expression by small double-stranded RNAs in invertebrate and vertebrate systems," *PNAS*, vol. 98(17):9742-9747 (2001).

Carthew, Richard W., "Gene silencing by double-stranded RNA," *Current Opinion in Cell Biology*, vol. 13:244-248 (2001).

Catalanotto, Caterina et al., "Gene silencing in worms and fungi," *Nature*, vol. 404:245 (2000).

Catalanotto, Caterina et al., "Involvement of small RNAs and role of the *qde* genes in the gene silencing pathway in *Neurospora*," *Genes & Development*, vol. 16:790-795 (2002).

Caudy, Amy A. et al., "Fragile X-related protein and VIG associate with the RNA interference machinery," *Genes & Development*, vol. 16:2491-2496 (2002).

Cogoni, Carlo et al., "Isolation of quelling-defective (*qde*) mutants impaired in posttranscriptional transgene-induced gene silencing in *Neurospora crassa*," *Proc. Natl. Acad. Sci. USA*, vol. 94:10233-10238 (1997).

Cogoni, Carlo et al., "Gene silencing in *Neurospora crassa* requires a protein homologous to RNA-dependent RNA polymerase," *Nature*, vol. 399:166-168 (1999).

Cogoni, Carlo et al., "Posttranscriptional Gene Silencing in *Neurospora* by a RecQ DNA Helicase," *Science*, vol. 286:2342-2344 (1999).

Conte, Darryl Jr. et al., "RNA Interference in *Caenorhabditis elegans*," *Current Protocols in Molecular Biology*, F.M. Asubel et al., eds., John Wiley & Sons, pp. 26.3.1-26.3.20 (2003).

Dalmay, Tamas et al., "An RNA-Dependent RNA Polymerase Gene in *Arabidopsis* Is Required for Posttranscriptional Gene Silencing Mediated by a Transgene but Not by a Virus," *Cell*, vol. 101:543-553 (2000).

Dalmay, Tamas et al., "*SDE3* encodes an RNA helicase required for posttranscriptional gene silencing in *Arabidopsis*," *The EMBO Journal*, vol. 20(8):2069-2077 (2001).

Dostie, Josée et al., "Numerous microRNPs in neuronal cells containing novel microRNAs," *RNA*, vol. 9:180-186 (2003).

Elbashir, Sayda M. et al., "Duplexes of 21-nucleotide RNAs mediated RNA interference in cultured mammalian cells," *Nature*, vol. 411:494-498 (2001).

Elbashir, Sayda M. et al., "Functional anatomy of siRNAs for mediating efficient RNAi in *Drosophila melanogaster* embryo lysate," *The EMBO Journal*, vol. 20(23):6877-6888 (2001).

Elbashir, Sayda M. et al., "RNA interference is mediated by 21- and 22-nucleotide RNAs," *Genes & Development*, vol. 15:188-200 (2001).

Enright, Anton J. et al., "MicroRNA targets in *Drosophila*," *Genome Biology*, vol. 5:R1 (2003).

Fagard, Mathilde et al., "AG01, QDE-2, and RDE-1 are related proteins required for post-transcriptional gene silencing in plants, quelling ni fungi, and RNA interference in animals," *PNAS*, vol. 97(21):11650-11654 (2000).

Fire, Andrew et al., "Potent and specific genetic interference by double-stranded RNA in *Caenorhabditis elegans*," *Nature*, vol. 391:806-811 (1998).

Grishok, Alla et al., "Genes and Mechanisms Related to RNA Interference Regulate Expression of the Small Temporal RNAs that Control *C. elegans* Developmental Timing," *Cell*, vol. 106:23-34 (2001).

Grishok, Alla et al., "Genetic Requirements for Inheritance of RNAi in *C. elegans*," *Science*, vol. 287:2494-2497 (2000).

Grishok, Alla et al., "RNAi (Nematodes *Caenorhabditis elegans*)," *Advances in Genetics*, vol. 46:339-360 (2002).

Ha, Ilho et al., "A bulged *lin-4/lin-14* RNA duplex is sufficient for *Caenorhabditis elegans lin-14* temporal gradient formation," *Genes & Development*, vol. 10:3041-3050 (1996).

Haley, Benjamin et al., "In vitro analysis of RNA interference in *Drosophila melanogaster*," *Methods*, vol. 30:330-336 (2003).

Hammond, Scott M. et al., "Argonaute2, a Link Between Genetic and Biochemical Analyses of RNAi," *Science*, vol. 293:1146-1150 (2001).

Hammond, Scott M. et al., "Post-Transcriptional Gene Silencing by Double-Stranded RNA," *Nature*, vol. 2:110-119 (2001).

Hutvágner, György et al., "A Cellular Function for the RNA-Interference Enzyme Dicer in the Maturation of the *let-7* Small Temporal RNA," *Science*, vol. 293:834-838 2001.

Hutvágner, György et al., "A microRNA in a Multiple-Turnover RNAi Enzyme Complex," *Science*, vol. 297:2056-2060 (2002).

Ketting, René F. et a., "*mut-7* of *C. elegans*, Required for Transposon Silencing and RNA Interference, Is a Homolog of Werner Syndrome Helicase and RNaseD," *Cell*, vol. 99:133-141 (1999).

Ketting, René F. et a., "A genetic link between co-suppression and RNA interference ni *C. elegans*," *Nature*, vol. 404:296-298 (2000).

Knight, Scott W. et al., "A Role for the RNase III Enzyme DCR-1 in RNA Interference and Germ Line Development in *Caenorhabditis elegans*," *Science*, vol. 293:2269-2271 (2001).

Lagos-Quintana, Mariana et al., "Identification of Novel Genes Coding for Small Expressed RNAs," *Science*, vol. 294:853-858 (2001).

Lagos-Quintana, Mariana et al., "Identification of Tissue-Specific MicroRNAs from Mouse," *Current Biology*, vol. 12:735-739 (2002).

Lagos-Quintana, Mariana et al., "New microRNAs from mouse and human," *RNA*, vol. 9:175-179 (2003).

Lau, Nelson C. et al., "An Abundant Class of Tiny RNAs with Probable Regulatory Roles in *Caenorhabditis elegans*," *Science*, vol. 294:858-862 (2001).

Lee, Rosalind C. et al., "An Extensive Class of Small RNAs in *Caenorhabditis elegans*," *Science*, vol. 294:862-864 (2001).

Lee, Rosalind C. et al., "The *C. elegans* Heterochronic Gene *lin-4* Encodes Small RNAs with Antisense Complementarity to *lin-14*," *Cell*, vol. 75:843-854 (1993).

Lewis, Benjamin P. et al., "Prediction of Mammalian MicroRNA Targets," *Cell*, vol. 115:787-798 (2003).

Liang, Xue-hai et al., "Small nuclear RNA interference induced by antisense or double-stranded RNA in trypanosomatids," *PNAS*, vol. 100(13):7521-7526 (2003).

Lim, Lee P. et al., "The microRNAs of *Caenorhabditis elegans*," *Genes & Development*, vol. 17:991-1008 (2003).

Lim, Lee P. et al., "Vertebrate MicroRNA Genes," *Science*, vol. 299:1540 (2003).

Liu, Qinghua et al., "R2D2, a Bridge Between the Initiation and Effector Steps of the *Drosophila* RNAi Pathway," *Science*, vol. 301:1921-1925 (2003).

Moss, Eric G. et al., "The Cold Shock Domain Protein LIN-28 Controls Developmental Timing in *C. elegans* and Is Regulated by the *lin-4* RNA," *Cell*, vol. 88:637-646 (1997).

Mourelatos, Zissimos et al., "miRNPs: a novel class of ribonucleoproteins containing numerous microRNAs," *Genes & Development*, vol. 16:720-728 (2002).

Mourrain, Philippe et al., "*Arabidopsis SGS2* and *SGS3* Genes Are Required for Posttranscriptional Gene Silencing and Natural Virus Resistance," *Cell*, vol. 101:533-542 2000.

Olsen, Philip H. et al., "The *lin-4* Regulatory RNA Controls Developmental Timing in *Caenorhabditis elegans* by Blocking LIN-14 Protein Synthesis after the Initiation of Translation," *Developmental Biology*, vol. 216:671-680 (1999).

Persengiev, Stephan P. et al., "Nonspecific, concentration-dependent stimulation and repression of mammalian gene expression by small interfering RNAs (siRNAs)," *RNA*, vol. 10:12-18 (2004).

Poy, Matthew N. et al., "A pancraetic islet-specific microRNA regulates insulin secretion," *Nature*, vol. 432:226-230 (2004).

Reinhart, Brenda J. et al., "MicroRNAs in plants," *Genes & Development*, vol. 16:1616-1626 (2002).

Reinhart, Brenda J. et al., "The 21-nucleotide let-7 RNA regulates developmental timing in *Caenorhabditis elegans*," *Nature*, vol. 403:901-906 (2000).

Saxena, Sandeep et al., "Small RNAs with Imperfect Match to Endogenous mRNA Repress Translation," *The Journal of Biological Chemistry*, vol. 278(45):44312-44319 (2003).

Schwarz, Dianne S. et al., "Evidence that siRNAs Function as Guides, Not Primers, in the *Drosophila* and Human RNAi Pathways," *Molecular Cell*, vol. 10:537-548 (2002).

Seggerson, Kathy et al., "Two Genetic Circuits Repress the *Caenorhabditis elegans* Heterochronic Gene *lin-28* after Translation Initiation," *Developmental Biology*, vol. 243:215-225 (2002).

Slack, Frank J. et al., "The *lin-41* RBCC Gene Acts in the *C. elegans* Heterochronic Pathway between the *let-7* Regulatory Rna and the LIN-29 Transcription Factor," *Molecular Cell*, vol. 5:659-669 (2000).

Sledz, Carol A. et al., "Activation of the interferon system by short-interfering RNAs," *Nature Cell Biology*, vol. 5(9):834-838 (2003).

Stark, Alexander et al., "Identification of *Drosophila* MicroRNA Targets," *PLOS Biology*, vol. 1(3):397-409 (2003).

Tabara, Hiroaki et al., "The dsRNA Binding Protein RDE-4 Interacts with RDE-1, DCR-1, and a DExH-Box Helicase to Direct RNAi in *C. elegans*," *Cell*, vol. 109:861-871 (2002).

Tabara, Hiroaki et al., "The *rde-1* Gene, RNA Interference and Transposon Silencing in *C. elegans*," *Cell*, vol. 99:123-132 (1999).

Tang, Guiliang et al., "A biochemical framework for RNA silencing in plants," *Genes & Development*, vol. 17:49-63 (2003).

Tijsterman, Marcel et al., "RNA Helicase MUT-14-Dependent Gene Silencing Triggered in *C. elegans* by Short Antisense RNAs," *Science*, Vo. 295:694-697 (2002).

Tijsterman, Marcel et al., "PPW-1, a PAZ/PIWI Protein Required for Efficient Germline RNAi, Is Defective in a Natural Isolate of *C. elegans*," *Current Biology*, vol. 12:1535-1540 (2002).

Tuschl, Thomas et al., "Targeted mRNA degradation by double-stranded RNA in vitro," *Genes & Development*, vol. 13:3191-3197 (1999).

Vella, Monica C. et al., "The *C. elegans* microRNA *let-7* binds to imperfect *let-7* complementary sites from the *lin-41* 3'UTR," *Genes & Development*, vol. 18:132-137 (2004).

Wightman, Bruce et al., "Posttranscriptional Regulation of the Heterochronic Gene *lin-14* by *lin-4* Mediates Temporal Pattern Formation in *C. elegans*," *Cell*, vol. 75:855-862 (1993).

Wu-Sharf, Dancia et al., "Transgene and Transposon Silencing in *Chlamydomonas reinhardtii* by a DEAH-Box RNA Helicase," *Science*, vol. 290:1159-1162 (2000).

Xu, Peizhang et al., "The *Drosophila* MicroRNA Mir-14 Suppresses Cell Death and Is Required for Normal Fat Metabolism," *Current Biology*, vol. 13:790-795 (2003).

Zamore, Phillip D. et al., "RNAi: Double-Stranded RNA Directs the ATP-Dependent Cleavage of mRNA at 21 to 23 Nucleotide Intervals," *Cell*, vol. 101:25-33 (2000).

Zeng, Yan et al., "Both Natural and Designed Micro RNAs Can Inhibit the Expression of Cognate mRNAs When Expressed in Human Cells," *Molecular Cell*, vol. 9:1327-1333 (2002).

Zeng, Yan et al., "MicroRNAs and small interfering RNAs can inhibit mRNA expression by similar mechanisms," *PNAS*, vol. 100(17):9779-9784 (2003).

Zeng, Yan et al., "Sequence requirements for micro RNA processing and function in human cells," *RNA*, vol. 9:112-123 (2003).

Amarzguioui, Mohammed et al., "Rational design and in vitro and in vivo delivery of Dicer substrate siRNA," *Nature Protocols*, vol. 1(2):508-517 (2006).

Bailly, Christian et al., "The use of diaminopurine to investigate structural properties of nucleic acids and molecular recognition between ligands and DNA," *Nucleic Acids Research*, vol. 26(19):4309-4314 (1998).

Boutla, Alexandra et al., "Short 5'-phosphorylated double-stranded RNAs induce RNA interference in *Drosophila*," *Current Biology*, vol. 11:1776-1780 (2001).

Caccone, Adalgisa et al., "Calibration of the Change in Thermal Stability of DNA Duplexes and Degree of Base Air Pair Mismatch," *Journal of Molecular Evolution*, vol. 27:212-216 (1988).

Chiu, Ya-Lin et al., "RNAi in Human Cells: Basic Structural and Functional Features of Small Interfering RNA," *Molecular Cell*, vol. 10:549-561 (2002).

Chiu, Ya-Lin et al., "siRNA function in RNAi: A chemical modification analysis," *RNA*, vol. 9:1034-1048 (2003).

Hannon, Gregory J. et al., "Unlocking the potential of the human genome with RNA interference," *Nature*, vol. 431:371-378 (2004).

Heale, Bret S.E. et al., "siRNA target site secondary structure predictions using local stable substructures," *Nucleic Acids Research*, vol. 33(3):1-10 (2005).

Kim, Daniel H. et al., "Strategies for silencing human disease using RNA interference," *Nature Reviews Genetics*, vol. 8:173-184 (2007).

Kim, Dong-Ho et al., "Synthetic dsRNA Dicer substrates enhances RNAi potency and efficacy," *Nature Biotechnology*, vol. 23(2):222-226 (2005).

Lewis, David L. et al., "Efficient delivery of siRNA for inhibition of gene expression in postnatal mice," *Nature Genetics*, vol. 32:107-108 (2002).

Lieberman, Judy et al., "Interfering with disease: opportunities and roadblocks to harnessing RNA interference," *Trends in Molecular Medicine*, vol. 9(9):397-403 (2003).

McCaffrey, Anton P. et al., "RNA interference in adult mice," *Nature*, vol. 418:38-39 (2002).

Merriam-Webster online, "engineer," retrieved online at http://www.merriam-webster.com/dictonary (2008).

Molecular Biology of the Cell, Fourth Edition, "DNA Replication Mechanisms," retrieved online at http://www.ncbi.nlm.nih.gov/books/bv.fcgi?highlight=DNA&rid=mboc4.section.754 (2008).

Molecular Biology of the Cell, Fourth Edition, "Figure 4-4," retrieved online at http://www.ncbi.nlm.nih.gov/books/bv.fcgi?rid=mboc4.figgrp (2008).

Molecular Biology of the Cell, Fourth Edition, "The Chemical Composition of a Cell," retrieved online at http://www.ncbi.nlm.nih.gov/books/bv.fcgi?highlight=hydrogen,dna,bond&rid=mboc4.section165 (2008).

Molecular Biology of the Cell, Fourth Edition, "Wobble base-pairing between codons and anticodons," retrieved online at http://www.ncbi.nlm.nih.gov/books/bv.fcgi?highlight=inosine&rid=mboc4.fig-grp.1058 (2008).

Rose, Scott D. et al., "Functional polarity is introduced by Dicer processing of short substrate RNAs," *Nucleic Acids Research*, vol. 33(13):4140-4156 (2005).

Scadden, A.D.J. et al., "RNAi is antagonized by A→I hyper-editing," *EMBO reports*, vol. 2(12):1109-1111 (2001).

Scherer, Lisa J. et al., "Approaches for the sequence-specific knockdown of mRNA," *Nature Biotechnology*, vol. 21(12):1457-1465 (2003).

Scherer, Lisa J. et al., "Rapid Assessment of Anti-HIV siRNA Efficacy Using PCR-Derived Pol III shRNA Cassettes," *Molecular Therapy*, vol. 10(3):597-603 (2004).

Scherer, Lisa J. et al., "Recent Applications of RNAi in Mammalian Systems," *Current Pharmaceutical Biotechnology*, vol. 5:355-360 (2004).

Scherer, Lisa et al., "Therapeutic Applications of RNA Interference: Recent Advances in siRNA Design," *Advances in Genetics*, vol. 52:1-21 (2004).

Snove, Ola Jr. et al., "Chemical Modifications Rescue Off-Target Effects of RNAi," *ACS Chemical Biology*, vol. 1(5):274-276 (2006).

Song, E. et al., "Intrahepatic Gene Silencing by RNA Interference," *Gastroenterology*, vol. 126(1):356-358 (2004).

Song, Erwei et al., "RNA interference targeting Fas protects mice from fulminant hepatitis," Nature Medicine, Vol. 9(3):347-351 (2003).

Sundaralingam, Muttaiya et al., "Hydrogen and hydration of DNA and RNA oligonucleotides," *Biophysical Chemistry*, vol. 95:273-282 (2002).

Tuschl, Thomas et al., "siRNAs and miRNAs," *Keystone Symposia, Abstract Book* (2004).

Wang, J. et al., "Fas siRNA Reduces Apoptotic Cell Death of Allogeneic-Transplanted Hepatocytes in Mouse Spleen," *Transplantation Proceedings*, Vo. 35:1594-1595 (2003).

Xia, Haibin et al., "siRNA-mediated gene silencing in vitro and in vivo," *Nature Biotechnology*, vol. 20:1006-1010 (2002).

Zamore, Phillip D. et al., "siRNAs knock down hepatitis," *Nature Medicine*, vol. 9(3):266-267 (2003).

Zhang, Haidi et al., "Human Dicer preferentially cleaves dsRNAs at their termini without a requirement for ATP," *The EMBO Journal*, vol. 21(21):5875-5885 (2002).

Office Action mailed Mar. 27, 2008 for U.S. Appl. No. 11/022,055 (Inventor: Phillip D. Zamore et al.).

Office Action mailed Aug. 17, 2007 for U.S. Appl. No. 11/022,055 (Inventor: Phillip D. Zamore et al.).

Office Action mailed Sep. 14, 2007 for U.S. Appl. No. 10/912,440 (Inventor: Phillip D. Zamore et al.).

Office Action mailed Jul. 2, 2008 for U.S. Appl. No. 10/912,440 (Inventor: Phillip D. Zamore et al.).

Office Action mailed Jan. 25, 2007 for U.S. Appl. No. 10/859,337 (Inventor: Phillip D. Zamore et al.).

Office Action mailed May 30, 2006 for U.S. Appl. No. 10/859,337 (Inventor: Phillip D. Zamore et al.).

International Search Report for Application No. PCT/US2005/029011, dated Apr. 13, 2006.

* cited by examiner

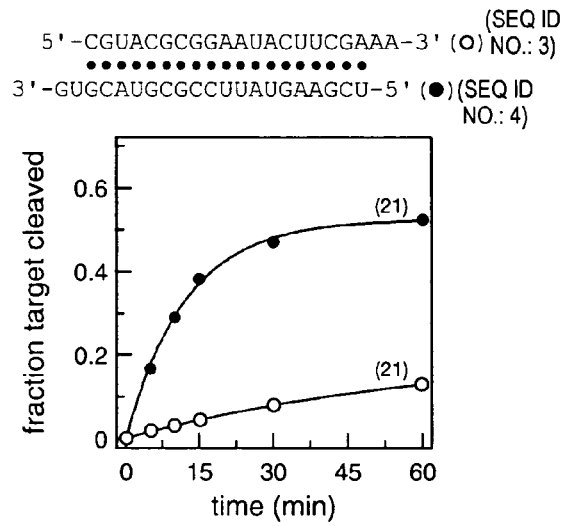
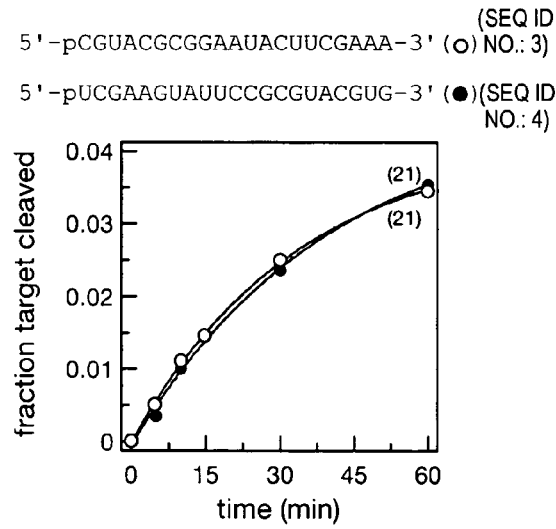
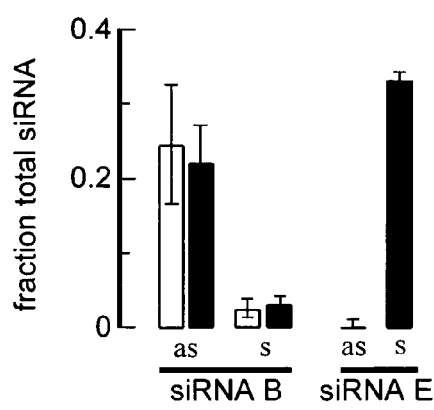
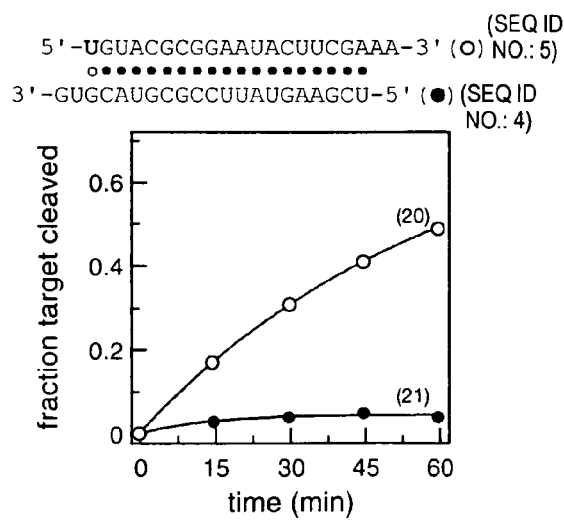

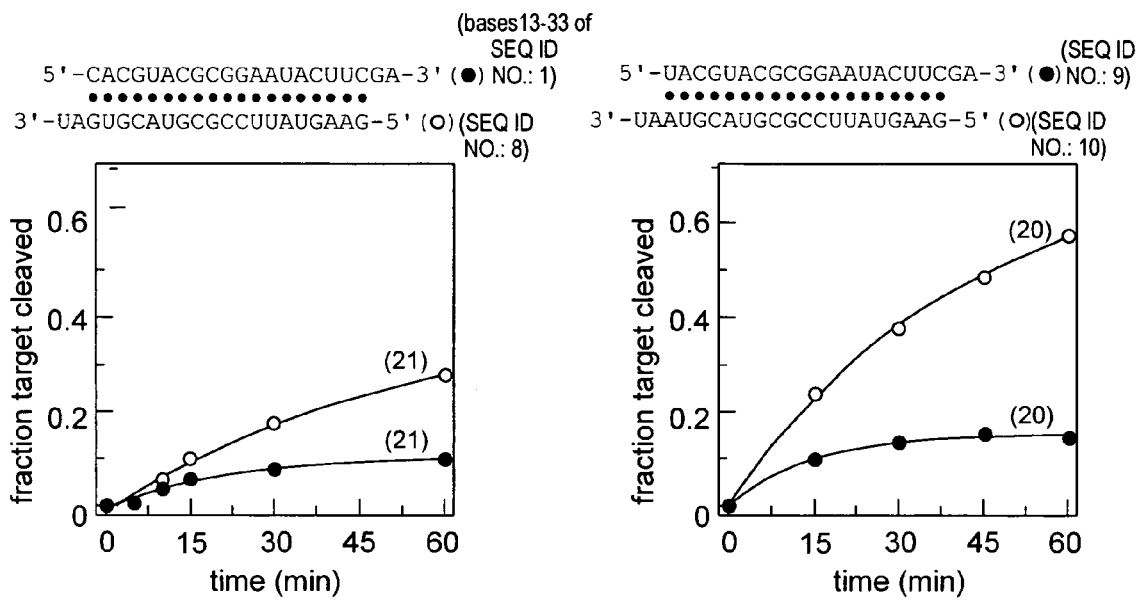
*Fig. 2A*
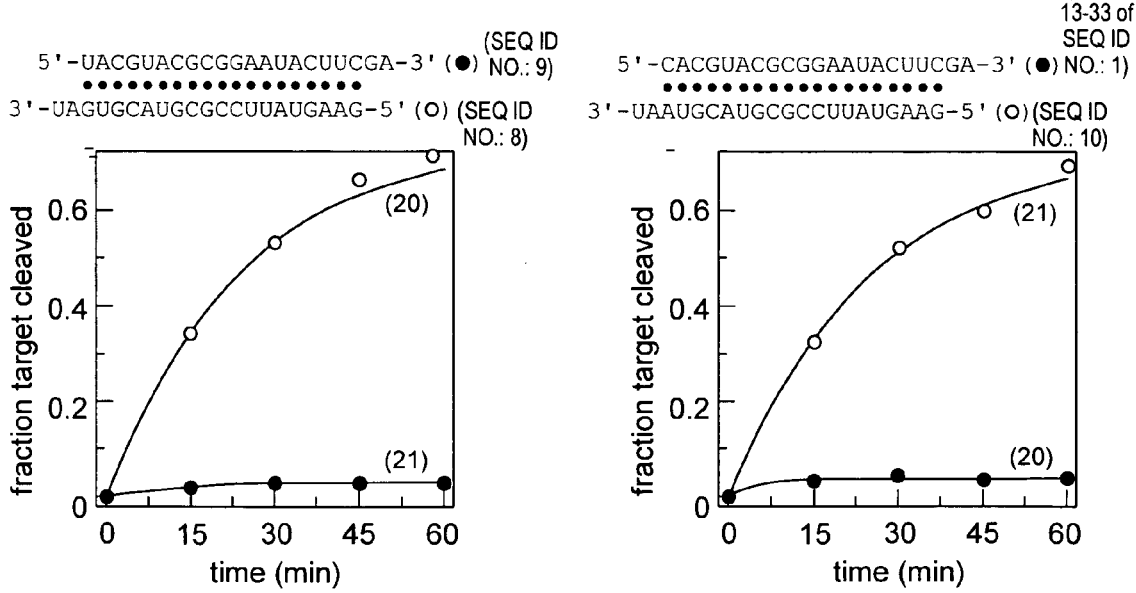

sod1 sense target: 5'-...agagaggcauguug<u>gagacuugggcaaugugac</u>ugcugacaa...3' (●)(SEQ ID NO.: 11)

sod1 anti-sense target: 3'-...cuccguacaac<u>cucugaacccguuacacuga</u>cgacuguuuc...5' (○) (SEQ ID NO.: 12)

Fig. 3A

5'-GAGACUUGGGCAAUGUGACdTdT-3' (○)(SEQ ID NO.: 13)
3'-dTdTCUCUGAACCCGUUACACUG-5' (●)(SEQ ID NO.: 14)

5'-GAGACUUGGGCAAUGUGAAdTdT-3' (○)(SEQ ID NO.: 15)
3'-dTdTCUCUGAACCCGUUACACUG-5' (●)(SEQ ID NO.: 14)

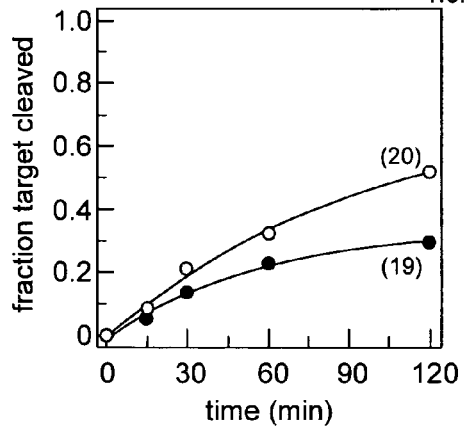

Fig. 3B

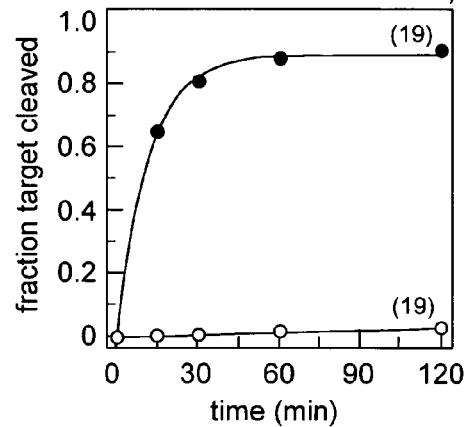

Fig. 3C

5'-GAGACUUGGGCAAUGUGACdTdT-3' (○)(SEQ ID NO.:13)
3'-dTdTCUCUGAACCCGUUACACUU-5' (●)(SEQ ID NO.: 16)

5'-GAGACUUGGGCAAUGUGAAdTdT-3' (○)(SEQ ID NO.: 15)
3'-dTdTCUCUGAACCCGUUACACUU-5' (●)(SEQ ID NO.: 16)

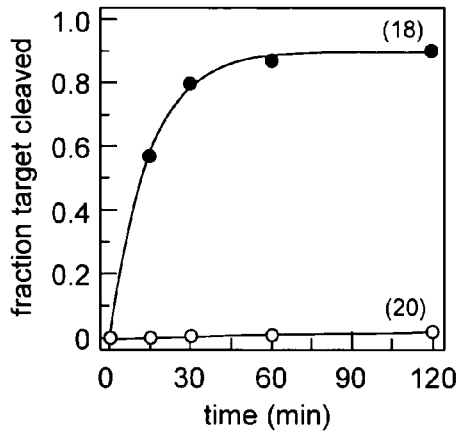

Fig. 3D

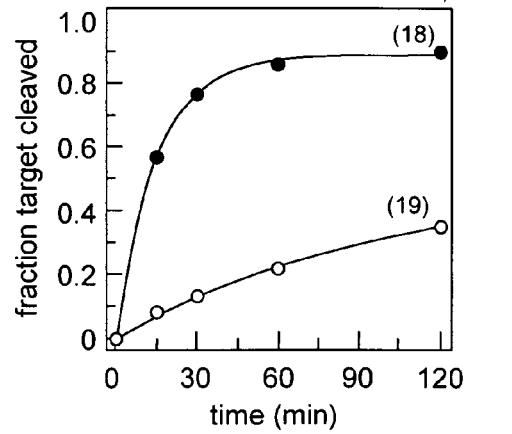

Fig. 3E

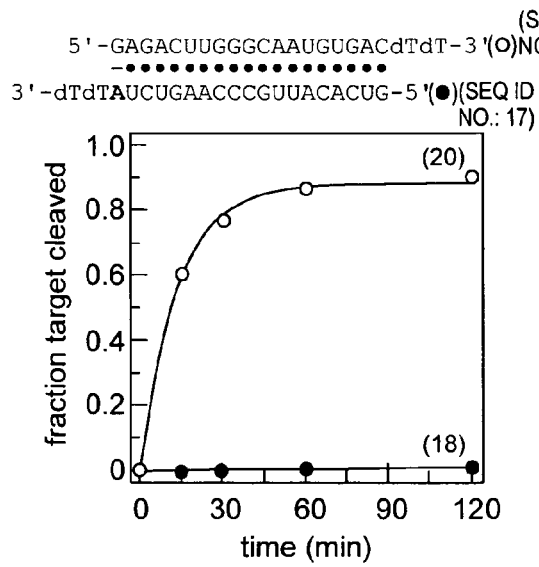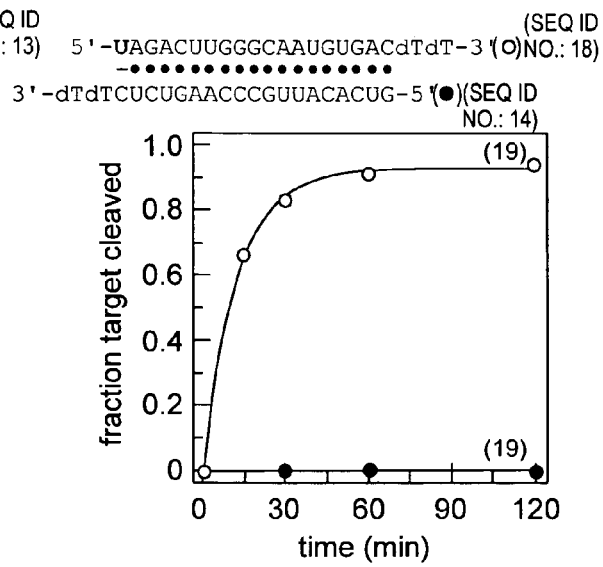
*Fig. 3F* *Fig. 3G*
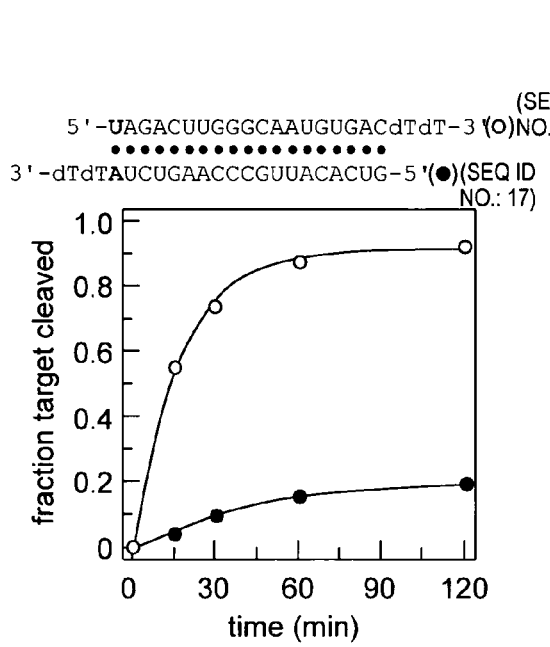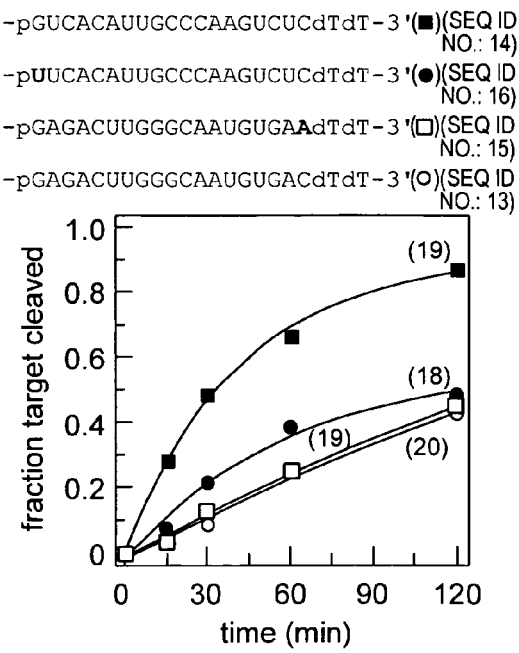
*Fig. 3H* *Fig. 3I*

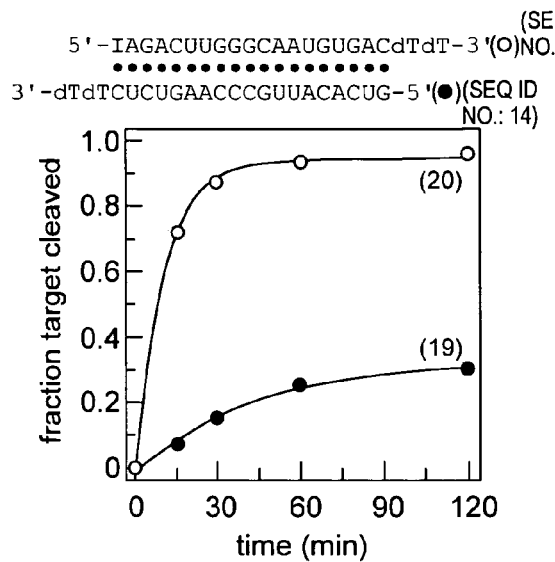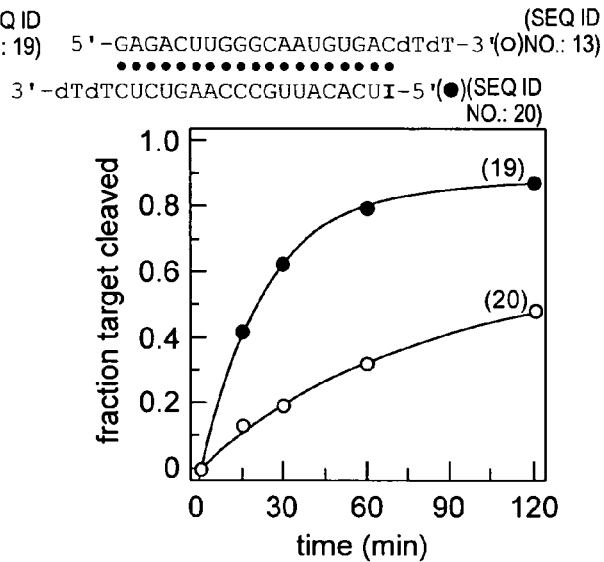
Fig. 4A
Fig. 4B
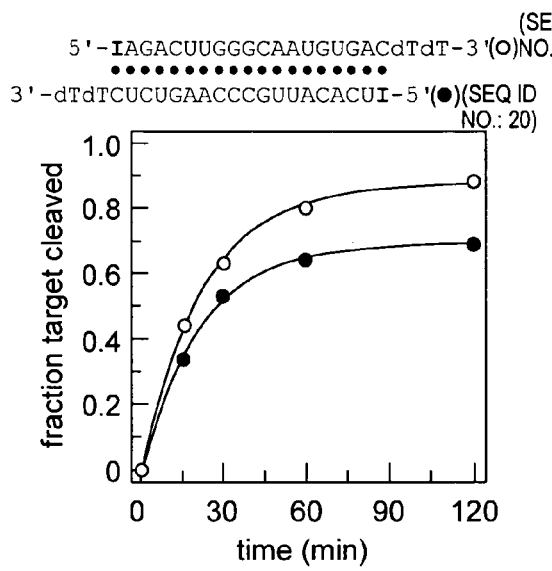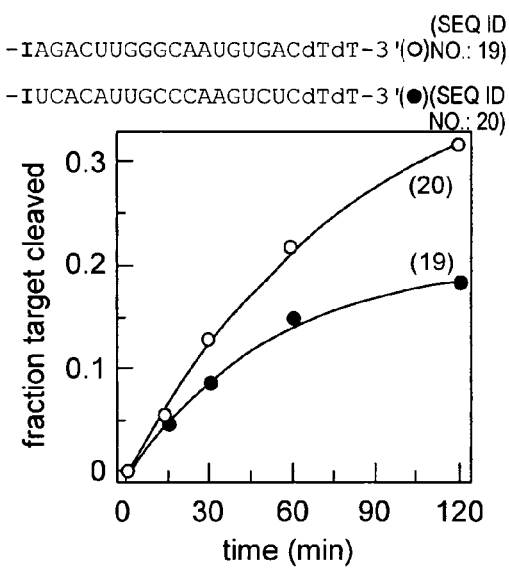
Fig. 4C
Fig. 4D

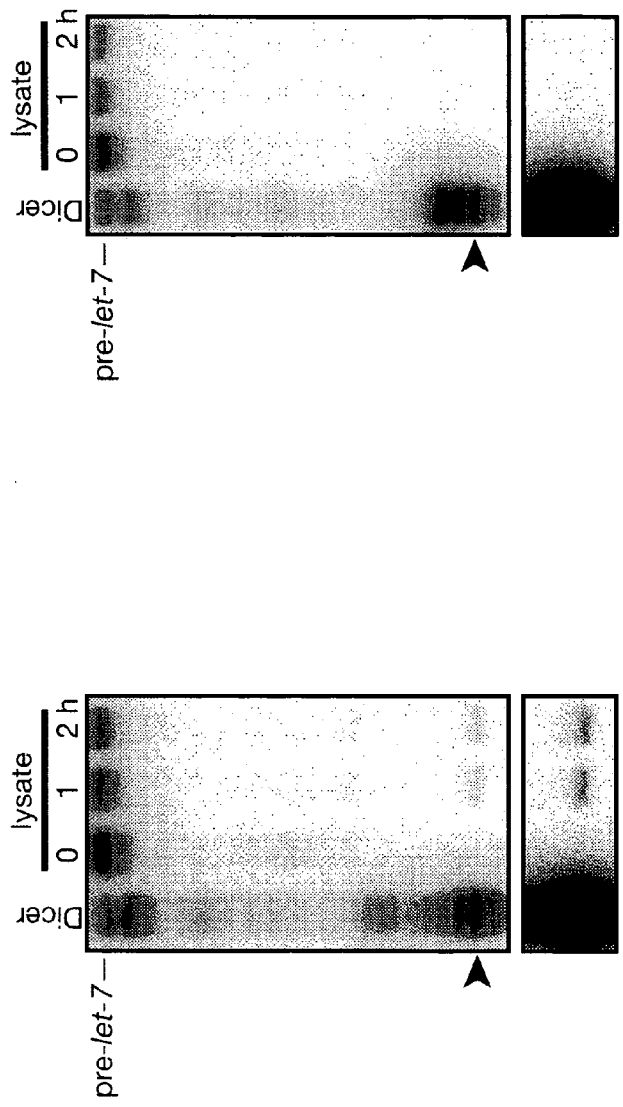
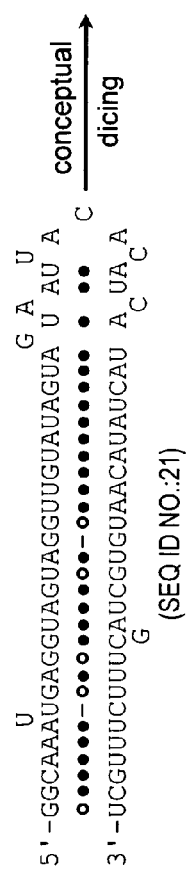
Fig. 5A
Fig. 5B
Fig. 5C

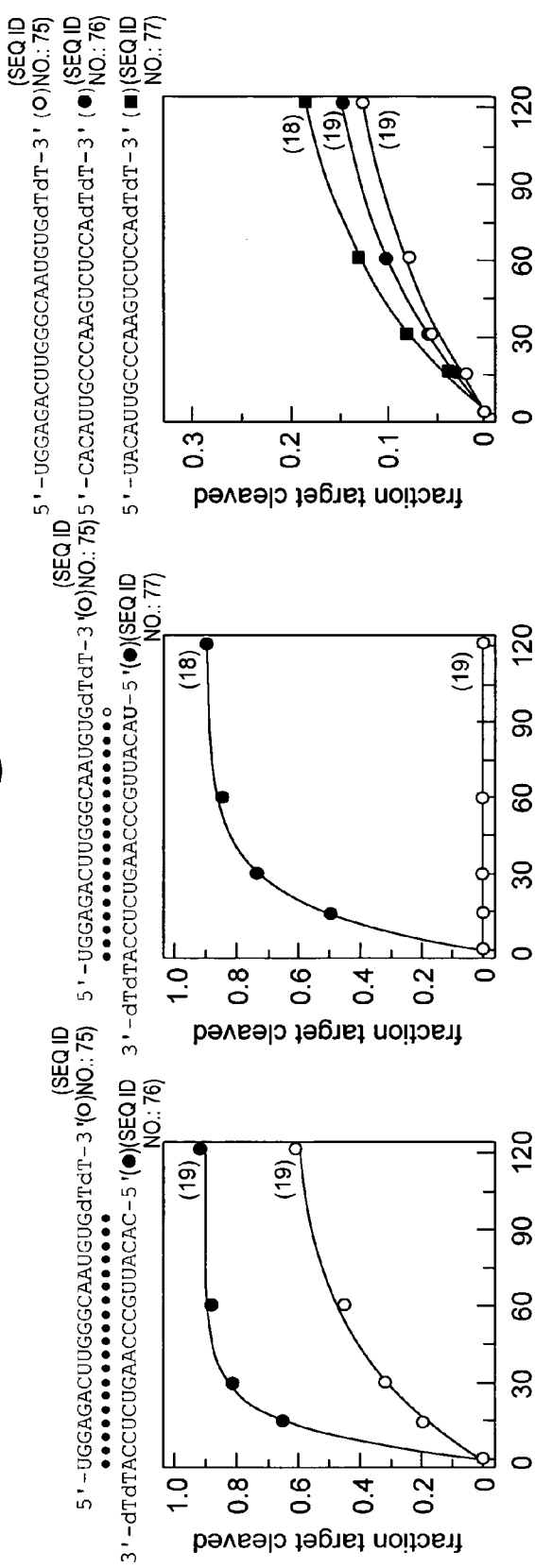

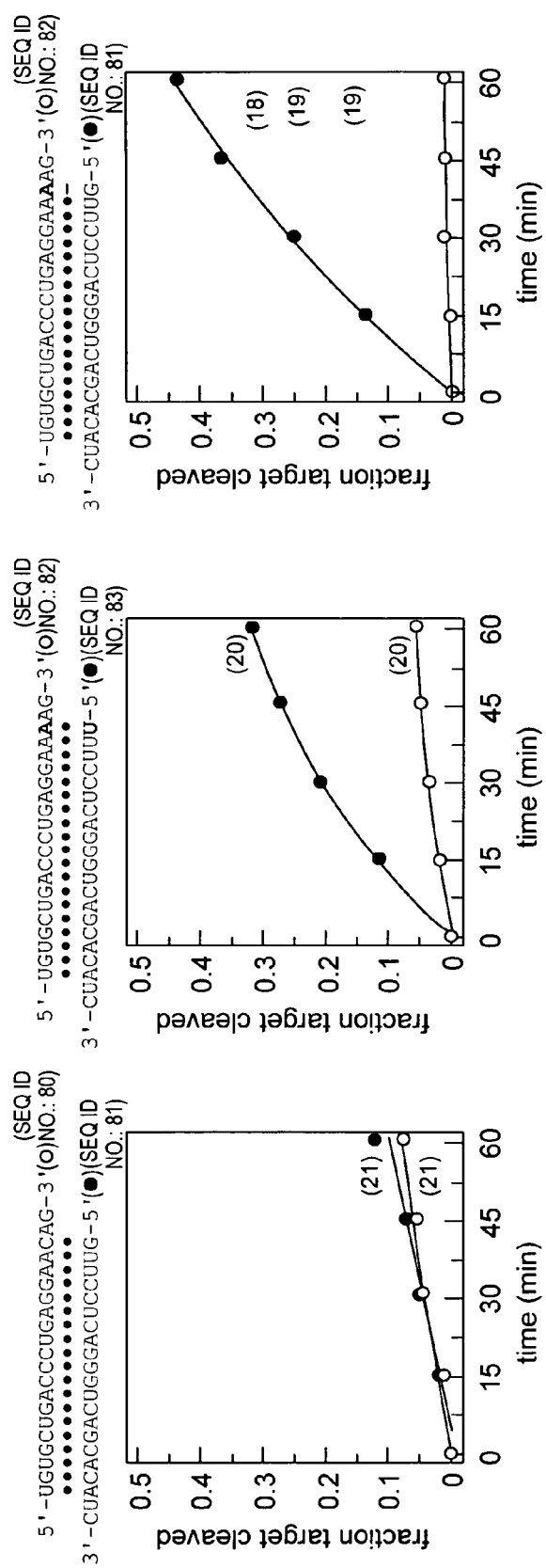

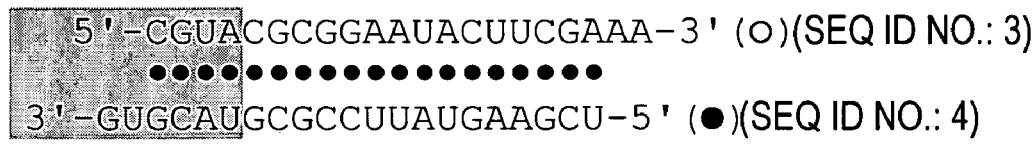
5'-CGUACGCGGAAUACUUCGAAA-3' (○)(SEQ ID NO.: 3)
●●●●●●●●●●●●●●●●●●●●
3'-GUGCAUGCGCCUUAUGAAGCU-5' (●)(SEQ ID NO.: 4)

```
        5'-CGUA
           ●●●●
        3'-GUGCAU
```

ΔG = -8.7 kcal/mol

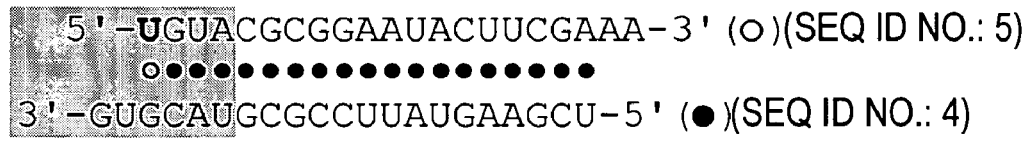
5'-UGUACGCGGAAUACUUCGAAA-3' (○)(SEQ ID NO.: 5)
○●●●●●●●●●●●●●●●●●●●●
3'-GUGCAUGCGCCUUAUGAAGCU-5' (●)(SEQ ID NO.: 4)

```
    5'-U
        GUA              5'-UGUA
        ●●●              ○●●●
        CAU              3'-GUGCAU
    3'-GAG
```
ΔG = -7.4 kcal/mol    ΔG = -7.2 kcal/mol 5'-CGUACGCGGAAUACUUCGAAA-3' (○)(SEQ ID NO.: 3)
●●●●●●●●●●●●●●●●●●●●
3'-GUGCAUGCGCCUUAUGAAGCU-5' (●)(SEQ ID NO.: 4)

```
        5'-UCGA
           ●●●●
        3'-AAAGCU
```

ΔG = -8.4 kcal/mol

*Fig. 10*

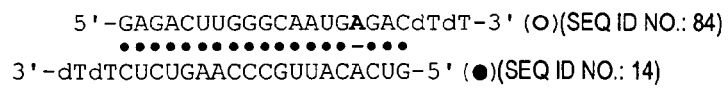
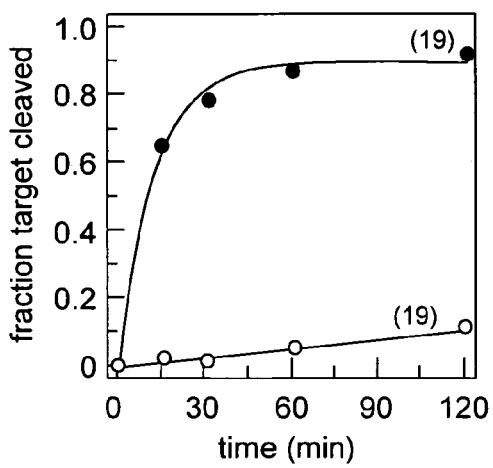
*Fig. 11A*
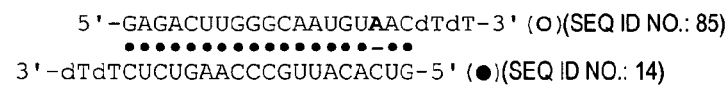
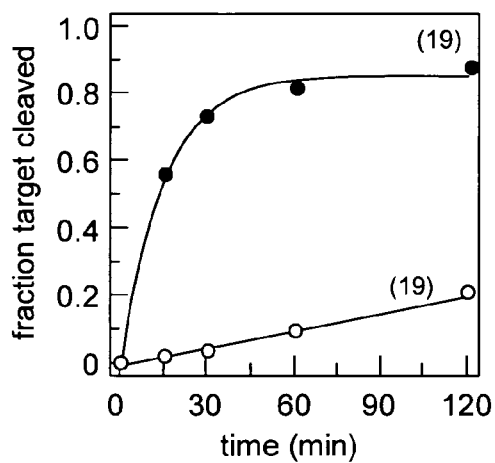
*Fig. 11B*
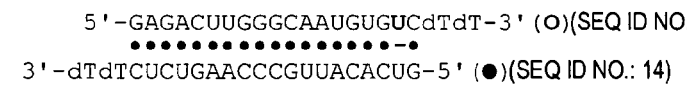
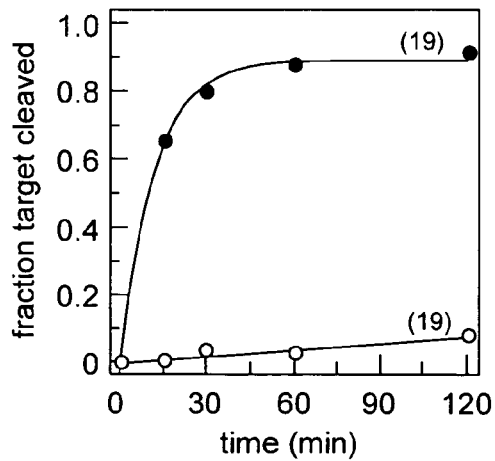
*Fig. 11C*

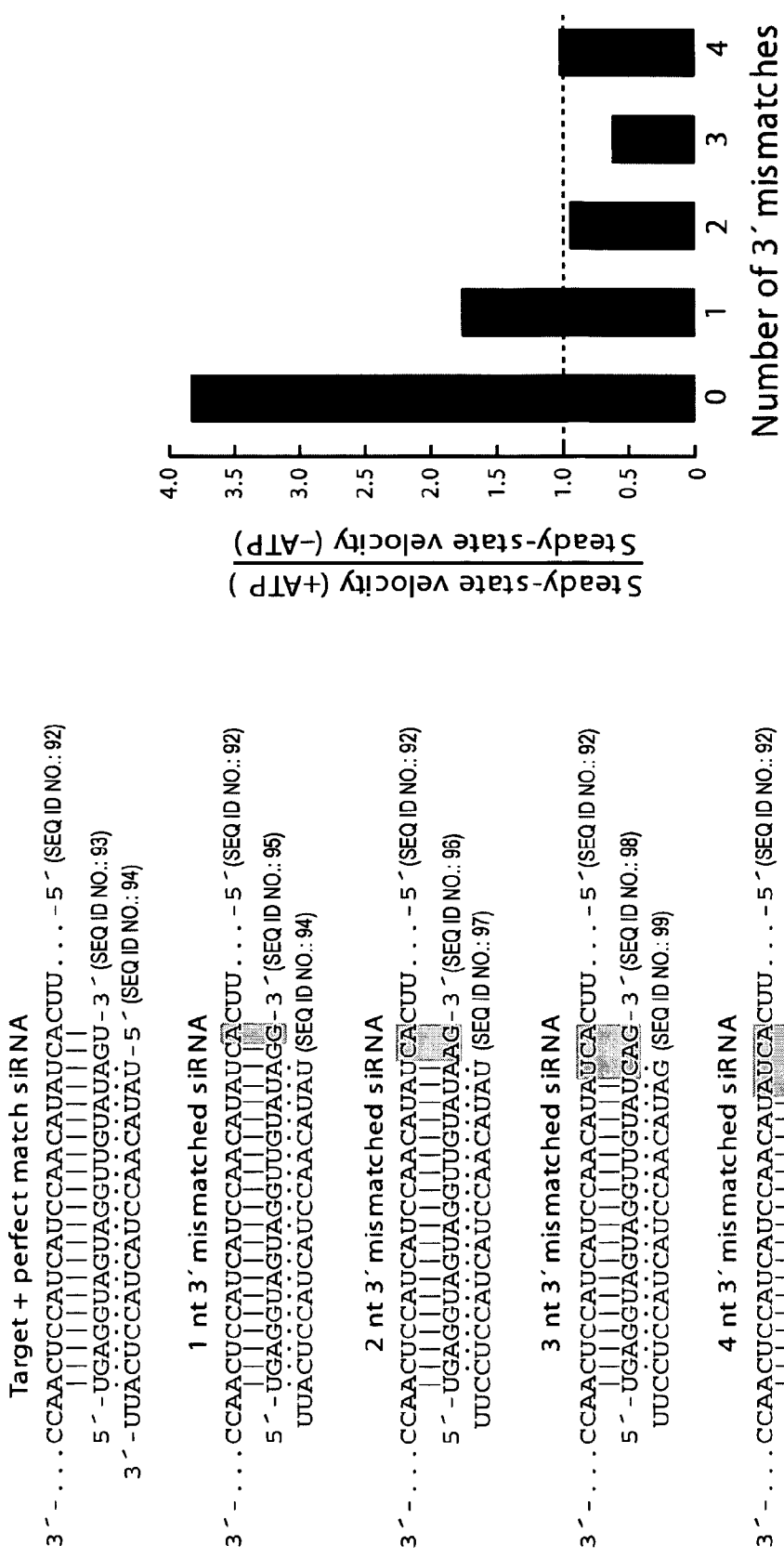

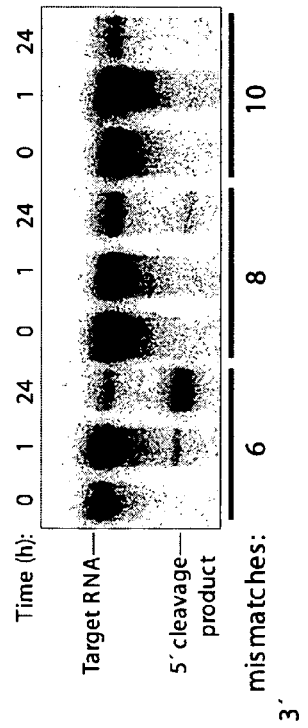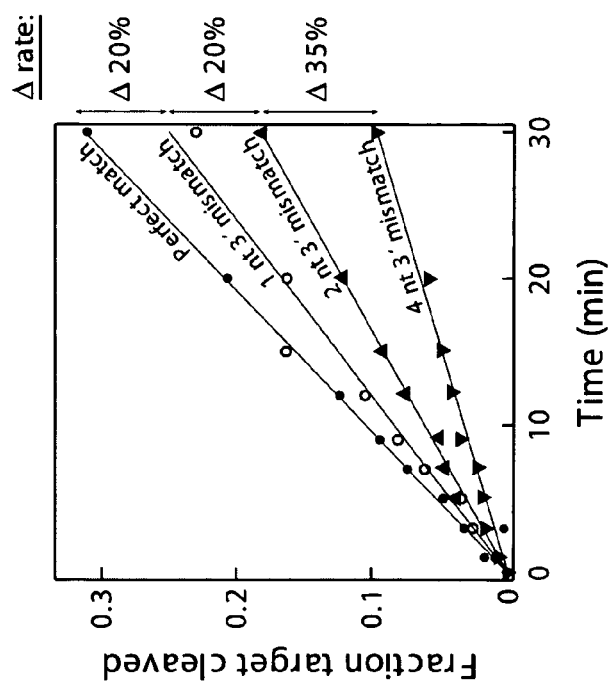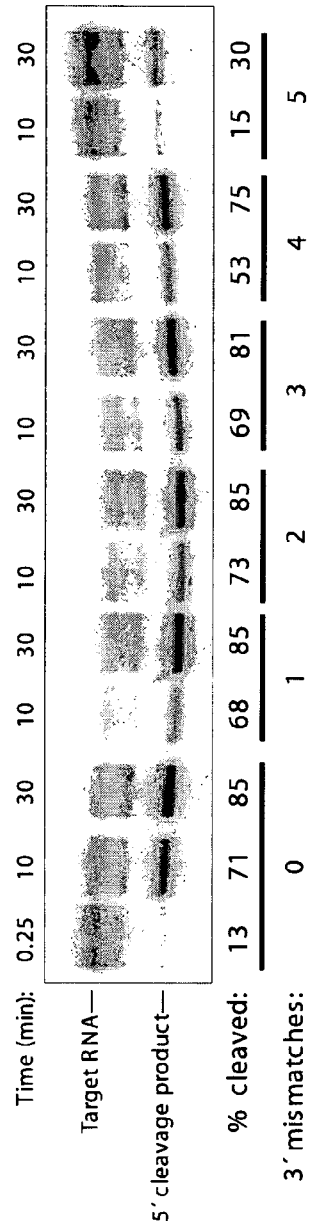
Fig. 15A
Fig. 15B
Fig. 15C

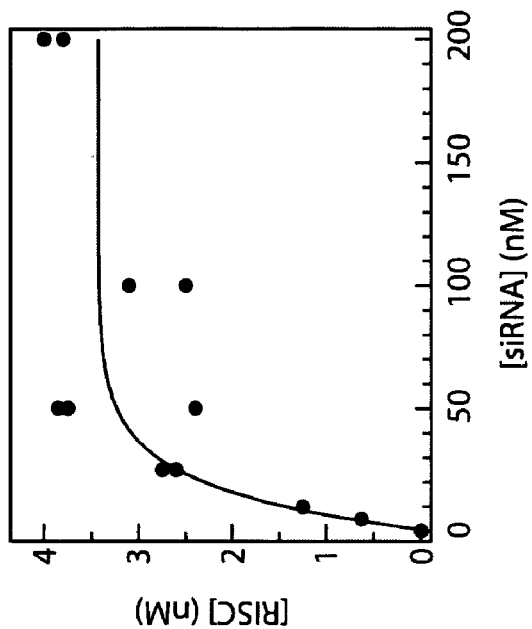
5'-*pUGAGGUAGGUUGUAUAGU-3' (SEQ ID NO.: 93)
3'-UUACUCCAUCCAACAUAU-5' (SEQ ID NO.: 94)
*Fig. 19A*
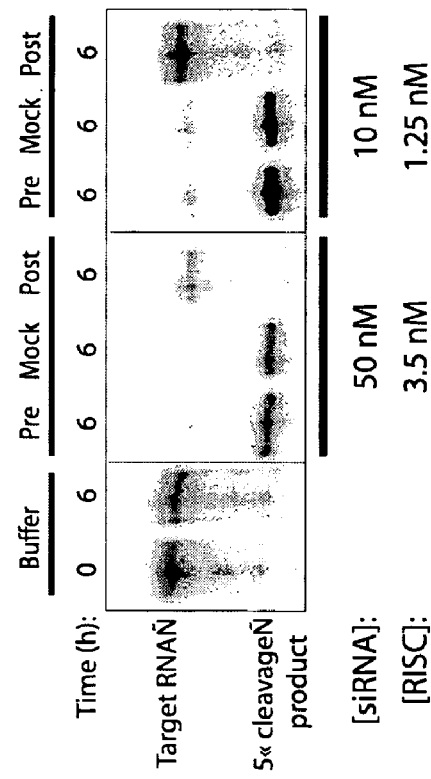
*Fig. 19C*
*Fig. 19B*

| Target and siRNA | Figure # |
|---|---|
| target: fully matched siRNA<br>3´-...CCAACUCCAUCAUCCAACAUAUCACUU...-5´ (SEQ ID NO.: 92)<br>       \|\|\|\|\|\|\|\|\|\|\|\|\|\|\|\|\|\|\|\|\|<br>5´-UGAGGUAGUAGGUUGUAUAGU-3´ (SEQ ID NO.: 93)<br>3´-UUACUCCAUCAUCCAACAUAU-5´ (SEQ ID NO.: 94)<br><br>target: 1 nt 3« mismatched siRNA<br>3´-...CCAACUCCAUCAUCCAACAUAUCACUU...-5´ (SEQ ID NO.: 92)<br>       \|\|\|\|\|\|\|\|\|\|\|\|\|\|\|\|\|\|\|\|<br>5´-UGAGGUAGUAGGUUGUAUAGG-3´ (SEQ ID NO.: 95)<br>UUACUCCAUCAUCCAACAUAU (SEQ ID NO.: 94)<br><br>target: 2 nt 3« mismatched siRNA<br>3´-...CCAACUCCAUCAUCCAACAUAUCACUU...-5´ (SEQ ID NO.: 92)<br>       \|\|\|\|\|\|\|\|\|\|\|\|\|\|\|\|\|\|\|<br>5´-UGAGGUAGUAGGUUGUAUAAG-3´ (SEQ ID NO.: 96)<br>UUCCUCCAUCAUCCAACAUAU (SEQ ID NO.: 97)<br><br>target: 3 nt 3« mismatched siRNA<br>3´-...CCAACUCCAUCAUCCAACAUAUCACUU...-5´ (SEQ ID NO.: 92)<br>       \|\|\|\|\|\|\|\|\|\|\|\|\|\|\|\|\|\|<br>5´-UGAGGUAGUAGGUUGUAUCAG-3´ (SEQ ID NO.: 98)<br>UUCCUCCAUCAUCCAACAUAG (SEQ ID NO.: 99)<br><br>target: 4 nt 3« mismatched siRNA<br>3´-...CCAACUCCAUCAUCCAACAUAUCACUU...-5´ (SEQ ID NO.: 92)<br>       \|\|\|\|\|\|\|\|\|\|\|\|\|\|\|\|\|<br>5´-UGAGGUAGUAGGUUGUAGCAG-3´ (SEQ ID NO.: 100)<br>UUCCUCCAUCAUCCAACAUCG (SEQ ID NO.: 101)<br><br>target: 5 nt 3« mismatched siRNA<br>3´-...CCAACUCCAUCAUCCAACAUAUCACUU...-5´ (SEQ ID NO.: 92)<br>       \|\|\|\|\|\|\|\|\|\|\|\|\|\|\|\|<br>5´-UGAGGUAGUAGGUUGUUGCAG-3´ (SEQ ID NO.: 102)<br>UUCCUCCAUCAUCCAACAACG (SEQ ID NO.: 103) | Figures 2b-d,<br>3a,b and 5a |

*Fig. 21A* target : 6 nt 3« mismatched siRNA

3´-...CCAACUCCAUCAUCCAACAUAUCACUU...-5´(SEQ ID NO.: 92)
　　　  |||||||||||||||
　　5´-UGAGGUAGUAGGUUGAUGCAG-3´(SEQ ID NO.: 104)
　　　  UUCCUCCAUCAUCCAACUACG (SEQ ID NO.: 105)

target : 8 nt 3« mismatched siRNA

3´-...CCAACUCCAUCAUCCAACAUAUCACUU...-5´(SEQ ID NO.: 92)
　　　  |||||||||||||
　　5´-UGAGGUAGUAGGUACAUGCAG-3´(SEQ ID NO.: 106)
　　　  UUCCUCCAUCAUCCAAGUACG (SEQ ID NO.: 107)

target : 10 nt 3« mismatched siRNA

3´-...CCAACUCCAUCAUCCAACAUAUCACUU...-5´(SEQ ID NO.: 92)
　　　  |||||||||||
　　5´-UGAGGUAGUAGCAACAUGCAG-3´(SEQ ID NO.: 108)
　　　  UUCCUCCAUCAUCCUUGUACG (SEQ ID NO.: 109)

Figure 3c

*Fig. 21B* target: 1 nt 5« mismatched siRNA
3´-...CCAACUCCAUCAUCCAACAUAUCACUU...-5´ (SEQ ID NO.: 92)
          ||||||||||||||||||||
     5´-AGAGGUAGUAGGUUGUAUAGU-3´ (SEQ ID NO.: 110)
        UUCCUCCAUCAUCCAACAUAU (SEQ ID NO.: 111)

target: 3 nt 5« mismatched siRNA
3´-...CCAACUCCAUCAUCCAACAUAUCACUU...-5´ (SEQ ID NO.: 92)
          ||||||||||||||||||
     5´-ACUGGUAGUAGGUUGUAUAGU-3´ (SEQ ID NO.: 112)
        UUCGACCAUCAUCCAACAUAU (SEQ ID NO.: 113)

target: 5 nt 5« mismatched siRNA
3´-...CCAACUCCAUCAUCCAACAUAUCACUU...-5´ (SEQ ID NO.: 92)
          ||||||||||||||||
     5´-ACUCCUAGUAGGUUGUAUAGU-3´ (SEQ ID NO.: 114)
        UUCGAGGAUCAUCCAACAUAU (SEQ ID NO.: 115)

target: 6 nt 5« mismatched siRNA
3´-...CCAACUCCAUCAUCCAACAUAUCACUU...-5´ (SEQ ID NO.: 92)
          |||||||||||||||
     5´-ACUCCAAGUAGGUUGUAUAGU-3´ (SEQ ID NO.: 116)
        UUCGAGGUUCAUCCAACAUAU (SEQ ID NO.: 117)

target: 7 nt 5« mismatched siRNA
3´-...CCAACUCCAUCAUCCAACAUAUCACUU...-5´ (SEQ ID NO.: 92)
          ||||||||||||||
     5´-ACUCCAUGUAGGUUGUAUAGU-3´ (SEQ ID NO.: 118)
        UUCGAGGUACAUCCAACAUAU (SEQ ID NO.: 119)

target: 8 nt 5« mismatched siRNA
3´-...CCAACUCCAUCAUCCAACAUAUCACUU...-5´ (SEQ ID NO.: 92)
          |||||||||||||
     5´-ACUCCAUCUAGGUUGUAUAGU-3´ (SEQ ID NO.: 120)
        UUCGAGGUAGAUCCAACAUAU (SEQ ID NO.: 121)

Figures 4a, d and 5a

*Fig. 21C*

8 nt 3« mismatched target : siRNA

3´-...CCAACUCCAUCAUCCAUGUACGUCCUU...-5´(SEQ ID NO.: 122)
　　　　　|||||||||||||
　　　　5´-UGAGGUAGUAGGUUGUAUAGU-3´(SEQ ID NO.: 123)
　　　　　UUCCUCCAUCAUCCAACAUAU (SEQ ID NO.: 111)

8 nt 5« mismatched target : siRNA

3´-...CCAUGAGGUAGAUCCAACAUAUCACUU...-5´(SEQ ID NO.: 124)
　　　　　　　|||||||||||||
　　　　5´-UGAGGUAGUAGGUUGUAUAGU-3´(SEQ ID NO.: 125)
　　　　　UUCCUCCAUCAUCCAACAUAU (SEQ ID NO.: 111)

Figure 4b

8 nt 5« mismatched target : 8 nt 5« mismatch siRNA

3´-...CCAUGAGGUAGAUCCAACAUAUCACUU...-5´(SEQ ID NO.: 124)
　　　　　|||||||||||||||||||||
　　　　5´-ACUCCAUCUAGGUUGUAUAGU-3´(SEQ ID NO.: 120)
　　　　　UUCGAGGUAGAUCCAACAUAU (SEQ ID NO.: 121)

*Fig. 21D* siRNA : 7 nt 3« mismatched target

3´- ... CCAACUCCAUCAUCCAAGUACGUCCUU ... -5´(SEQ ID NO.: 126)
        |||||||||||||
   5´-UGAGGUAGUAGGUUGUAUAGU-3´(SEQ ID NO.: 127)
    UUCCUCCAUCAUCCAACAUAU (SEQ ID NO.: 111)

1 nt 5« mismatched siRNA : 7 nt 3« mismatched target

3´- ... CCAACUCCAUCAUCCAAGUACGUCCUU ... -5´(SEQ ID NO.: 126)
        |||||||||||||
   5´-AGAGGUAGUAGGUUGUAUAGU-3´(SEQ ID NO.: 128)
    UUCCUCCAUCAUCCAACAUAU(SEQ ID NO.: 111)

2 nt 5« mismatched siRNA : 7 nt 3« mismatched target

3´- ... CCAAGUCCAUCAUCCAAGUACGUCCUU ... -5´(SEQ ID NO.: 129)
        |||||||||||
   5´-AGAGGUAGUAGGUUGUAUAGU-3´(SEQ ID NO.: 128)
    UUCCUCCAUCAUCCAACAUAU (SEQ ID NO.: 111)

3 nt 5« mismatched siRNA : 7 nt 3« mismatched target

3´- ... CCAACUCCAUCAUCCAAGUACGUCCUU ... -5´(SEQ ID NO.: 126)
        ||||||||||
   5´-ACUGGUAGUAGGUUGUAUAGU-3´(SEQ ID NO.: 130)
    UUCGACCAUCAUCCAACAUAU (SEQ ID NO.: 113)

4 nt 5« mismatched siRNA : 7 nt 3« mismatched target

3´- ... CCAACUCCAUCAUCCAAGUACGUCCUU ... -5´(SEQ ID NO.: 126)
        |||||||||
   5´-ACUCGUAGUAGGUUGUAUAGU-3´(SEQ ID NO.: 131)
    UUCGACCAUCAUCCAACAUAU (SEQ ID NO.: 113)

Figure 4c

*Fig. 21E* siRNA : 8 nt 3« mismatched target

3´-...CCAACUCCAUCAUCCAUGUACGUCCUU...-5´(SEQ ID NO.: 132)
      |||||||||||||
   5´-UGAGGUAGUAGGUUGUAUAGU-3´(SEQ ID NO.: 127)
      UUCCUCCAUCAUCCAACAUAU (SEQ ID NO.: 111)

1 nt 5« mismatched siRNA : 8 nt 3« mismatcheded target

3´-...CCAACUCCAUCAUCCAUGUACGUCCUU...-5´(SEQ ID NO.: 132)
      ||||||||||||
   5´-AGAGGUAGUAGGUUGUAUAGU-3´(SEQ ID NO.: 128)
      UUCCUCCAUCAUCCAACAUAU (SEQ ID NO.: 111)

2 nt 5« mismatched siRNA : 8 nt 3« mismatched target

3´-...CCAAGUCCAUCAUCCAUGUACGUCCUU...-5´(SEQ ID NO.: 133)
      |||||||||||
   5´-AGAGGUAGUAGGUUGUAUAGU-3´(SEQ ID NO.: 128)
      UUCCUCCAUCAUCCAACAUAU (SEQ ID NO.: 111)

3 nt 5« mismatched siRNA : 8 nt 3« mismatched target

3´-...CCAACUCCAUCAUCCAUGUACGUCCUU...-5´(SEQ ID NO.: 132)
      ||||||||||
   5´-ACUGGUAGUAGGUUGUAUAGU-3´(SEQ ID NO.: 130)
      UUCGACCAUCAUCCAACAUAU (SEQ ID NO.: 113)

4 nt 5« mismatched siRNA : 8 nt 3« mismatched target

3´-...CCAACUCCAUCAUCCAUGUACGUCCUU...-5´(SEQ ID NO.: 132)
      |||||||||
   5´-ACUCGUAGUAGGUUGUAUAGU-3´(SEQ ID NO.: 131)
      UUCGACCAUCAUCCAACAUAU (SEQ ID NO.: 113)

Figure 4c

Fig. 21F siRNA : 9 nt 3« mismatched target

3´-...CCAACUCCAUCAUCCUUGUACGUCCUU...-5´(SEQ ID NO.: 134)
    5´-UGAGGUAGUAGGUUGUAUAGU-3´(SEQ ID NO.: 127)
     UUCCUCCAUCAUCCAACAUAU (SEQ ID NO.: 111)

1 nt 5« mismatched siRNA : 9 nt 3« mismatched target

3´-...CCAACUCCAUCAUCCUUGUACGUCCUU...-5´(SEQ ID NO.: 134)
    5´-AGAGGUAGUAGGUUGUAUAGU-3´(SEQ ID NO.: 128)
     UUCCUCCAUCAUCCAACAUAU (SEQ ID NO.: 111)

2 nt 5« mismatched siRNA : 9 nt 3« mismatched target

3´-...CCAAGUCCAUCAUCCUUGUACGUCCUU...-5´(SEQ ID NO.: 135)
    5´-AGAGGUAGUAGGUUGUAUAGU-3´(SEQ ID NO.: 128)
     UUCCUCCAUCAUCCAACAUAU (SEQ ID NO.: 111)

3 nt 5« mismatched siRNA : 9 nt 3« mismatched target

3´-...CCAACUCCAUCAUCCUUGUACGUCCUU...-5´(SEQ ID NO.: 134)
    5´-ACUGGUAGUAGGUUGUAUAGU-3´(SEQ ID NO.: 130)
     UUCGACCAUCAUCCAACAUAU (SEQ ID NO.: 136)

4 nt 5« mismatched siRNA : 9 nt 3« mismatched target

3´-...CCAACUCCAUCAUCCUUGUACGUCCUU...-5´(SEQ ID NO.: 134)
    5´-ACUCGUAGUAGGUUGUAUAGU-3´(SEQ ID NO.: 131)
     UUCGACCAUCAUCCAACAUAU (SEQ ID NO.: 136)

Figure 4c

*Fig. 21G* perfect matched 2«-O-methyl target : siRNA
3´-UUCCAACUCCAUCAUCCAACAUAUCACUUCU-bi-5´(SEQ ID NO.: 137)
          |||||||||||||||||||||
     5´-UGAGGUAGUAGGUUGUAUAGU-3´(SEQ ID NO.:125)
        UUACUCCAUGAUCCAACAUAU(SEQ ID NO.: 138)

4 nt 5« mismatched 2«-O-methyl target : siRNA
3´-UUCCAACUCCAUCAUCCAACAUAUCACUUCU-bi—5´(SEQ ID NO.: 137)
              |||||||||||||||||
     5´-ACUCGUAGUAGGUUGUAUAGU-3´(SEQ ID NO.: 131)
        UUCGAGGUAGAUCCAACAUAU(SEQ ID NO.: 139)

8 nt 5« mismatched 2«-O-methyl target : siRNA
3´-UUCCAACUCCAUCAUCCAACAUAUCACUUCU-bi-5´(SEQ ID NO.: 137)
                  |||||||||||||
     5´-ACUCCAUCUAGGUUGUAUAGU-3´(SEQ ID NO.: 120)
        UUCGAGGUAGAUCCAACAUAU (SEQ ID NO.: 139)

4 nt 5« central mismatched 2«-O-methyl target : siRNA
3´-UUCCAACUCCAAGAACCAACAUAUCACUUAA-5´(SEQ ID NO.: 140)
        ||||||   |||||||||||||
     5´-UGAGGUAGUAGGUUGUAUAGU-3´(SEQ ID NO.: 125)
        UUACUCCAUCAUCCAACAUAU (SEQ ID NO.: 94)

4 nt 3« central mismatched 2«-O-methyl target : siRNA
3´-UUCCAACUCCAUCAAGGUACAUAUCACUUCU-5´(SEQ ID NO.: 141)
        ||||||||    ||||||||||
     5´-UGAGGUAGUAGGUUGUAUAGU-3´(SEQ ID NO.: 125)
        UUACUCCAUCAUCCAACAUAU (SEQ ID NO.: 94)

4 nt 3« mismatched 2«-O-methyl target : siRNA
3´-UUCCAACUCCAUCAUCCAACAUCAACCUUCU-5´(SEQ ID NO.: 142)
        |||||||||||||||||
     5´-UGAGGUAGUAGGUUGUAUAGU-3´(SEQ ID NO.: 125)
        UUACUCCAUCAUCCAACAUAU (SEQ ID NO.: 94)

7 nt 3« mismatched 2«-O-methyl target : siRNA
3´-UUCCAACUCCAUCAUCCAGAACCAACCUUCU-5´(SEQ ID NO.: 143)
        ||||||||||||||
     5´-UGAGGUAGUAGGUUGUAUAGU-3´(SEQ ID NO.: 125)
        UUACUCCAUCAUCCAACAUAU (SEQ ID NO.: 94)

8 nt 3« mismatched 2«-O-methyl target : siRNA
3´-UUCCAACUCCAUCAUCCAACAUAUCACUUCU-bi—5´(SEQ ID NO.: 137)
        |||||||||||||
     5´-UGAGGUAGUAGGUACAUGCAG-3´(SEQ ID NO.: 106)
        UUCCUCCAUCAUCCAAGUACG (SEQ ID NO.: 107)

SEQUENCE LISTING

<160> NUMBER OF SEQ ID NOS: 164

<210> SEQ ID NO 1
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
cgaggugaac aucacguacg cggaauacuu cgaaaugucc                              40

<210> SEQ ID NO 2
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
ggacauuucg aaguauuccg cguacgugau guucaccucg                              40

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
cguacgcgga auacuucgaa a                                                  21

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
ucgaaguauu ccgcguacgu g                                                  21

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
uguacgcgga auacuucgaa a                                              21

<210> SEQ ID NO 6
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
cgaggugaac aucacguacg cggaauacuu cgaaaugucc                          40

<210> SEQ ID NO 7
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
ggacauuucg aaguauuccg cguacgugau guucaccucg                          40

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
gaaguauucc gcguacguga u                                              21

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
uacguacgcg gaauacuucg a                                              21

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
gaaguauucc gcguacguaa u                                              21

<210> SEQ ID NO 11

```
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
agagaggcau guuggagacu ugggcaaugu gacugcugac aa                          42

<210> SEQ ID NO 12
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
cuuugucagc agucacauug cccaagucuc caacaugccu c                           41

<210> SEQ ID NO 13
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 13
gagacuuggg caaugugact t                                                 21

<210> SEQ ID NO 14
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 14
gucacauugc ccaagucuct t                                                 21

<210> SEQ ID NO 15
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 15
gagacuuggg caaugugaat t                                                 21

<210> SEQ ID NO 16
<211> LENGTH: 21
<212> TYPE: DNA
<213> ORGANISM: Artificial Sequence
<220> FEATURE:
<223> OTHER INFORMATION: Description of Combined DNA/RNA Molecule:
```

Synthetic oligonucleotide
<220> FEATURE:
<223> OTHER INFORMATION: Description of Artificial Sequence: Synthetic
      oligonucleotide

<400> SEQUENCE: 16
uucacauugc ccaagucuct t                                                    21

<210> SEQ ID NO 17
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 17
gucacauugc ccaagucuat t                                                    21

<210> SEQ ID NO 18
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 18
uagacuuggg caaugugact t                                                    21

<210> SEQ ID NO 19
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)
<223> OTHER INFORMATION: Inosine

<400> SEQUENCE: 19
nagacuuggg caaugugact t                                                    21

<210> SEQ ID NO 20
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)
<223> OTHER INFORMATION: Inosine

<400> SEQUENCE: 20
nucacauugc ccaagucuct t                                              21

<210> SEQ ID NO 21
<211> LENGTH: 72
<212> TYPE: RNA
<213> ORGANISM: Drosophila sp.

<400> SEQUENCE: 21
ggcaaauuga gguaguaggu uguauaguag uaauuacaca ucauacuaua caaugugcua    60
gcuuucuuug cu                                                        72

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
ugagguagua gguuguauag u                                              21

<210> SEQ ID NO 23
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
uauacaaugu gcuagcuuuc uu                                             22

<210> SEQ ID NO 24
<211> LENGTH: 22
<212> TYPE: RNA
<213> ORGANISM: Drosophila sp.

<400> SEQUENCE: 24
ccaugcuucc uugcauucaa ua                                             22

<210> SEQ ID NO 25
<211> LENGTH: 22
<212> TYPE: RNA
<213> ORGANISM: Drosophila sp.

<400> SEQUENCE: 25
uggaauguaa agaaguaugg ag                                             22

<210> SEQ ID NO 26
<211> LENGTH: 21
<212> TYPE: RNA
<213> ORGANISM: Drosophila sp.

<400> SEQUENCE: 26
ucucaaagug guugugaaau g                                              21

<210> SEQ ID NO 27
<211> LENGTH: 23
<212> TYPE: RNA
<213> ORGANISM: Drosophila sp.

<400> SEQUENCE: 27
uaucacagcc agcuuugaug agc                                            23

<210> SEQ ID NO 28
<211> LENGTH: 22
<212> TYPE: RNA
<213> ORGANISM: Drosophila sp.

<400> SEQUENCE: 28
cucaucaagu gguugugaua ug                                            22

<210> SEQ ID NO 29
<211> LENGTH: 22
<212> TYPE: RNA
<213> ORGANISM: Drosophila sp.

<400> SEQUENCE: 29
ucuucaaagu ggcagugaca ug                                            22

<210> SEQ ID NO 30
<211> LENGTH: 23
<212> TYPE: RNA
<213> ORGANISM: Drosophila sp.

<400> SEQUENCE: 30
uaucacagcc agcuuugagg agc                                           23

<210> SEQ ID NO 31
<211> LENGTH: 22
<212> TYPE: RNA
<213> ORGANISM: Drosophila sp.

<400> SEQUENCE: 31
ucuucaaagu gguugugaaa ug                                            22

<210> SEQ ID NO 32
<211> LENGTH: 22
<212> TYPE: RNA
<213> ORGANISM: Drosophila sp.

<400> SEQUENCE: 32
ggaugcaucu ugugcaguua ug                                            22

<210> SEQ ID NO 33
<211> LENGTH: 22
<212> TYPE: RNA
<213> ORGANISM: Drosophila sp.

<400> SEQUENCE: 33
ucacugggca aagugugucu ca                                            22

<210> SEQ ID NO 34
<211> LENGTH: 22
<212> TYPE: RNA
<213> ORGANISM: Drosophila sp.

<400> SEQUENCE: 34 cuuggucgu ccagccuuag gu                                             22

<210> SEQ ID NO 35
<211> LENGTH: 21
<212> TYPE: RNA
<213> ORGANISM: Drosophila sp.

<400> SEQUENCE: 35

-continued

```
auaaagcuag acaaccauug a                                    21

<210> SEQ ID NO 36
<211> LENGTH: 23
<212> TYPE: RNA
<213> ORGANISM: Drosophila sp.

<400> SEQUENCE: 36
aaaggaacga ucguugugau aug                                  23

<210> SEQ ID NO 37
<211> LENGTH: 22
<212> TYPE: RNA
<213> ORGANISM: Drosophila sp.

<400> SEQUENCE: 37
uaucacagug auuuccuuu au                                    22

<210> SEQ ID NO 38
<211> LENGTH: 22
<212> TYPE: RNA
<213> ORGANISM: Drosophila sp.

<400> SEQUENCE: 38
agggaauagu ugcugugcug ua                                   22

<210> SEQ ID NO 39
<211> LENGTH: 22
<212> TYPE: RNA
<213> ORGANISM: Drosophila sp.

<400> SEQUENCE: 39
uaucacagug gcuguucuuu uu                                   22

<210> SEQ ID NO 40
<211> LENGTH: 23
<212> TYPE: RNA
<213> ORGANISM: Drosophila sp.

<400> SEQUENCE: 40
agggaacuuc ugcugcugau aua                                  23

<210> SEQ ID NO 41
<211> LENGTH: 22
<212> TYPE: RNA
<213> ORGANISM: Drosophila sp.

<400> SEQUENCE: 41
uaucacagug gcuguucuuu uu                                   22

<210> SEQ ID NO 42
<211> LENGTH: 23
<212> TYPE: RNA
<213> ORGANISM: Drosophila sp.

<400> SEQUENCE: 42
agggaacggu ugcugaugau gua                                  23

<210> SEQ ID NO 43
<211> LENGTH: 23
<212> TYPE: RNA
<213> ORGANISM: Drosophila sp.

<400> SEQUENCE: 43
```
uggaagacua gugauuuugu ugu                                          23

<210> SEQ ID NO 44
<211> LENGTH: 26
<212> TYPE: RNA
<213> ORGANISM: Drosophila sp.

<400> SEQUENCE: 44
uaacaauaaa ucccuugucu ucuuac                                       26

<210> SEQ ID NO 45
<211> LENGTH: 22
<212> TYPE: RNA
<213> ORGANISM: Drosophila sp.

<400> SEQUENCE: 45
caucggaccg ggcagcauua ga                                           22

<210> SEQ ID NO 46
<211> LENGTH: 23
<212> TYPE: RNA
<213> ORGANISM: Drosophila sp.

<400> SEQUENCE: 46
uaauacuguc agguaaagau guc                                          23

<210> SEQ ID NO 47
<211> LENGTH: 23
<212> TYPE: RNA
<213> ORGANISM: Drosophila sp.

<400> SEQUENCE: 47
ucuuugguua ucuagcugua uga                                          23

<210> SEQ ID NO 48
<211> LENGTH: 23
<212> TYPE: RNA
<213> ORGANISM: Drosophila sp.

<400> SEQUENCE: 48
auaaagcuag cuuaccgaag uua                                          23

<210> SEQ ID NO 49
<211> LENGTH: 21
<212> TYPE: RNA
<213> ORGANISM: Drosophila sp.

<400> SEQUENCE: 49
acccuguaga uccgaauuug u                                            21

<210> SEQ ID NO 50
<211> LENGTH: 22
<212> TYPE: RNA
<213> ORGANISM: Drosophila sp.

<400> SEQUENCE: 50
aaauucgguu cuagagaggu uu                                           22

<210> SEQ ID NO 51
<211> LENGTH: 21
<212> TYPE: RNA
<213> ORGANISM: Drosophila sp.

```
<400> SEQUENCE: 51
aagaacuuuc ucugugaccc g                                              21

<210> SEQ ID NO 52
<211> LENGTH: 21
<212> TYPE: RNA
<213> ORGANISM: Drosophila sp.

<400> SEQUENCE: 52
caucacaguc ugaguucuug c                                              21

<210> SEQ ID NO 53
<211> LENGTH: 23
<212> TYPE: RNA
<213> ORGANISM: Drosophila sp.

<400> SEQUENCE: 53
ugaguauuac aucagguacu ggu                                            23

<210> SEQ ID NO 54
<211> LENGTH: 22
<212> TYPE: RNA
<213> ORGANISM: Drosophila sp.

<400> SEQUENCE: 54
caguacuuau gucauacuac gc                                             22

<210> SEQ ID NO 55
<211> LENGTH: 23
<212> TYPE: RNA
<213> ORGANISM: Drosophila sp.

<400> SEQUENCE: 55
uccucaaagg guugugaaau guc                                            23

<210> SEQ ID NO 56
<211> LENGTH: 23
<212> TYPE: RNA
<213> ORGANISM: Drosophila sp.

<400> SEQUENCE: 56
auaucacagc cauuugaug agu                                             23

<210> SEQ ID NO 57
<211> LENGTH: 25
<212> TYPE: RNA
<213> ORGANISM: Drosophila sp.

<400> SEQUENCE: 57
ucguuaaaau guuugugaac uuaug                                          25

<210> SEQ ID NO 58
<211> LENGTH: 22
<212> TYPE: RNA
<213> ORGANISM: Drosophila sp.

<400> SEQUENCE: 58
uaucacagcc auuuugacga gu                                             22

<210> SEQ ID NO 59
<211> LENGTH: 22
<212> TYPE: RNA
<213> ORGANISM: Drosophila sp.
```

<400> SEQUENCE: 59
gcgucaaaau gacugugagc ua					22

<210> SEQ ID NO 60
<211> LENGTH: 22
<212> TYPE: RNA
<213> ORGANISM: Drosophila sp.

<400> SEQUENCE: 60
uaucacagcc auuuugacga gu					22

<210> SEQ ID NO 61
<211> LENGTH: 21
<212> TYPE: RNA
<213> ORGANISM: Drosophila sp.

<400> SEQUENCE: 61
ggagcgagac ggggacucac u					21

<210> SEQ ID NO 62
<211> LENGTH: 21
<212> TYPE: RNA
<213> ORGANISM: Drosophila sp.

<400> SEQUENCE: 62
ucagucuuuu ucucucuccu a					21

<210> SEQ ID NO 63
<211> LENGTH: 22
<212> TYPE: RNA
<213> ORGANISM: Drosophila sp.

<400> SEQUENCE: 63
guauccacug uaggccuaua ug					22

<210> SEQ ID NO 64
<211> LENGTH: 21
<212> TYPE: RNA
<213> ORGANISM: Drosophila sp.

<400> SEQUENCE: 64
uaaggcacgc ggugaaugcc a					21

<210> SEQ ID NO 65
<211> LENGTH: 22
<212> TYPE: RNA
<213> ORGANISM: Drosophila sp.

<400> SEQUENCE: 65
ucccugagac ccuaacuugu ga					22

<210> SEQ ID NO 66
<211> LENGTH: 22
<212> TYPE: RNA
<213> ORGANISM: Drosophila sp.

<400> SEQUENCE: 66
acaaguuuug aucuccggua uu					22

<210> SEQ ID NO 67
<211> LENGTH: 23
<212> TYPE: RNA

<213> ORGANISM: Drosophila sp.

<400> SEQUENCE: 67
agcugguuga caucggguca gau            23

<210> SEQ ID NO 68
<211> LENGTH: 22
<212> TYPE: RNA
<213> ORGANISM: Drosophila sp.

<400> SEQUENCE: 68 uuggucccu ucaaccagcu gu              22

<210> SEQ ID NO 69
<211> LENGTH: 21
<212> TYPE: RNA
<213> ORGANISM: Drosophila sp.

<400> SEQUENCE: 69
ccuuaucauu cucucgcccc g              21

<210> SEQ ID NO 70
<211> LENGTH: 22
<212> TYPE: RNA
<213> ORGANISM: Drosophila sp.

<400> SEQUENCE: 70
uggacggaga acugauaagg gc             22

<210> SEQ ID NO 71
<211> LENGTH: 22
<212> TYPE: RNA
<213> ORGANISM: Drosophila sp.

<400> SEQUENCE: 71
cgguuuucga uuugguuuga cu             22

<210> SEQ ID NO 72
<211> LENGTH: 23
<212> TYPE: RNA
<213> ORGANISM: Drosophila sp.

<400> SEQUENCE: 72
ugagaucauu uugaaagcug auu            23

<210> SEQ ID NO 73
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
agagaggcau guuggagacu ugggcaaugu gacugcugac aa          42

<210> SEQ ID NO 74
<211> LENGTH: 41
<212> TYPE: RNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic -continued oligonucleotide

<400> SEQUENCE: 74
cuuugucagc agucacauug cccaagucuc caacaugccu c         41

<210> SEQ ID NO 75
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 75
uggagacuug ggcaaugugt t         21

<210> SEQ ID NO 76
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 76
cacauugccc aagucuccat t         21

<210> SEQ ID NO 77
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 77
uacauugccc aagucuccat t         21

<210> SEQ ID NO 78
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
ugcagcugau caucgaugug cugacccuga ggaacaguuc         40

<210> SEQ ID NO 79
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
gaacuguucc ucagggucag cacaucgaug aucagcugca         40

```
<210> SEQ ID NO 80
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
ugugcugacc cugaggaaca g                                              21

<210> SEQ ID NO 81
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
guuccucagg gucagcacau c                                              21

<210> SEQ ID NO 82
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
ugugcugacc cugaggaaaa g                                              21

<210> SEQ ID NO 83
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
uuuccucagg gucagcacau c                                              21

<210> SEQ ID NO 84
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 84
gagacuuggg caaugagact t                                              21

<210> SEQ ID NO 85
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
```

-continued

```
      oligonucleotide

<400> SEQUENCE: 85
gagacuuggg caauguaact t                                              21

<210> SEQ ID NO 86
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 86
gagacuuggg caauguguct t                                              21

<210> SEQ ID NO 87
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 87
gucacauugc ccaagacuct t                                              21

<210> SEQ ID NO 88
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 88
gucacauugc ccaaguguct t                                              21

<210> SEQ ID NO 89
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 89
gucacauugc ccaagucact t                                              21

<210> SEQ ID NO 90
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
```

<223> OTHER INFORMATION: Description of Artificial Sequence: Synthetic
oligonucleotide

<400> SEQUENCE: 90
gagacuuggg caauguggct t                                              21

<210> SEQ ID NO 91
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 91
guuacauugc ccaagucuct t                                              21

<210> SEQ ID NO 92
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
uucacuauac aaccuacuac cucaacc                                        27

<210> SEQ ID NO 93
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
ugagguagua gguuguauag u                                              21

<210> SEQ ID NO 94
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
uauacaaccu acuaccucau u                                              21

<210> SEQ ID NO 95
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
ugagguagua gguuguauag g                                              21

<210> SEQ ID NO 96
<211> LENGTH: 21
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 96
ugagguagua gguuguauaa g                                              21

<210> SEQ ID NO 97
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
uauacaaccu acuaccuccu u                                              21

<210> SEQ ID NO 98
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
ugagguagua gguuguauca g                                              21

<210> SEQ ID NO 99
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
gauacaaccu acuaccuccu u                                              21

<210> SEQ ID NO 100
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
ugagguagua gguuguagca g                                              21

<210> SEQ ID NO 101
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
gcuacaaccu acuaccuccu u                                              21

<210> SEQ ID NO 102
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 102
ugagguagua gguuguugca g                                              21

<210> SEQ ID NO 103
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
gcaacaaccu acuaccuccu u                                              21

<210> SEQ ID NO 104
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
ugagguagua gguugaugca g                                              21

<210> SEQ ID NO 105
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
gcaucaaccu acuaccuccu u                                              21

<210> SEQ ID NO 106
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
ugagguagua gguacaugca g                                              21

<210> SEQ ID NO 107
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
gcaugaaccu acuaccuccu u                                              21

<210> SEQ ID NO 108
<211> LENGTH: 21
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 108
ugagguagua gcaacaugca g          21

<210> SEQ ID NO 109
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
gcauguuccu acuaccuccu u          21

<210> SEQ ID NO 110
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
agagguagua gguuguauag u          21

<210> SEQ ID NO 111
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
uauacaaccu acuaccuccu u          21

<210> SEQ ID NO 112
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
acugguagua gguuguauag u          21

<210> SEQ ID NO 113
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
uauacaaccu acuaccagcu u          21

<210> SEQ ID NO 114
<211> LENGTH: 21
<212> TYPE: RNA
<213> ORGANISM: Artificial Sequence
<220> FEATURE:
<223> OTHER INFORMATION: Description of Artificial Sequence: Synthetic

```
                                    oligonucleotide

<400> SEQUENCE: 114
acuccaguaa gguuguauag u                                              21

<210> SEQ ID NO 115
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
uauacaaccu acuaggagcu u                                              21

<210> SEQ ID NO 116
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
acuccaagua gguuguauag u                                              21

<210> SEQ ID NO 117
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
uauacaaccu acuuggagcu u                                              21

<210> SEQ ID NO 118
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
acuccaugua gguuguauag u                                              21

<210> SEQ ID NO 119
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
uauacaaccu acauggagcu u                                              21

<210> SEQ ID NO 120
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 120
acuccaucua gguuguauag u                                              21

<210> SEQ ID NO 121
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
uauacaaccu agauggagcu u                                              21

<210> SEQ ID NO 122
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
uuccugcaug uaccuacuac cucaacc                                        27

<210> SEQ ID NO 123
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
ugagguagua gguuguauag u                                              21

<210> SEQ ID NO 124
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
uucacuauac aaccuagaug gaguacc                                        27

<210> SEQ ID NO 125
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
ugagguagua gguuguauag u                                              21

<210> SEQ ID NO 126
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 126
uuccugcaug aaccuacuac cucaacc                              27

<210> SEQ ID NO 127
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
ugagguagua gguuguauag u                                    21

<210> SEQ ID NO 128
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
agagguagua gguuguauag u                                    21

<210> SEQ ID NO 129
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
uuccugcaug aaccuacuac cugaacc                              27

<210> SEQ ID NO 130
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
acugguagua gguuguauag u                                    21

<210> SEQ ID NO 131
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
acucguagua gguuguauag u                                    21

<210> SEQ ID NO 132
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
uuccugcaug uaccuacuac cucaacc                                           27

<210> SEQ ID NO 133
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
uuccugcaug uaccuacuac cugaacc                                           27

<210> SEQ ID NO 134
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
uuccugcaug uuccuacuac cucaacc                                           27

<210> SEQ ID NO 135
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
uuccugcaug uuccuacuac cugaacc                                           27

<210> SEQ ID NO 136
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
uauacaaccu acuaccagcu u                                                 21

<210> SEQ ID NO 137
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
ucuucacuau acaaccuacu accucaaccu u                                      31

<210> SEQ ID NO 138
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
uauacaaccu aguaccucau u            21

<210> SEQ ID NO 139
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
uauacaaccu agauggagcu u            21

<210> SEQ ID NO 140
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
aauucacuau acaaccaaga accucaaccu u            31

<210> SEQ ID NO 141
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
ucuucacuau acauggaacu accucaaccu u            31

<210> SEQ ID NO 142
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
ucuuccaacu acaaccuacu accucaaccu u            31

<210> SEQ ID NO 143
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
ucuuccaacc aagaccuacu accucaaccu u            31

<210> SEQ ID NO 144
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
cgctaatacg actcactata gcagttggcg ccgcgaacga            40

<210> SEQ ID NO 145
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
gcgtaatacg actcactata gtcacatctc atctacctcc                              40

<210> SEQ ID NO 146
<211> LENGTH: 106
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
cccatttagg tgacactata gatttacatc gcgttgagtg tagaacggtt gtataaaagg        60
ttgaggtagt aggttgtata gtgaagagag gagttcatga tcagtg                      106

<210> SEQ ID NO 147
<211> LENGTH: 106
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
cccatttagg tgacactata gatttacatc gcgttgagtg tagaacggtt gtataaaagg        60
ttgaggtagt aggttcatgc aggaagagag gagttcatga tcagtg                      106

<210> SEQ ID NO 148
<211> LENGTH: 106
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      primer

<400> SEQUENCE: 148
cccatttagg tgacactata gatttacatc gcgttgagtg tagaacggtt gtataaaagg        60
ttgaggtagt aggtacaugc aggaagagag gagttcatga tcagtg                      106

<210> SEQ ID NO 149
<211> LENGTH: 106
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
cccatttagg tgacactata gatttacatc gcgttgagtg tagaacggtt gtataaaagg        60
ttgaggtagt aggaacatgc aggaagagag gagttcatga tcagtg                      106

<210> SEQ ID NO 150

```
<211> LENGTH: 106
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
cccatttagg tgacactata gatttacatc gcgttgagtg tagaacggtt gtataaaagg      60
tactccatct aggttgtata gtgaagagag gagttcatga tcagtg                   106

<210> SEQ ID NO 151
<211> LENGTH: 106
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
cccatttagg tgacactata gatttacatc gcgttgagtg tagaacggtt gtataaaagg      60
tactcgtagt aggttgtata gtgaagagag gagttcatga tcagtg                   106

<210> SEQ ID NO 152
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
gcgtaatacg actcactata ggaacagtat gtctcagaca tc                        42

<210> SEQ ID NO 153
<211> LENGTH: 21
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 153
uucgaaguau uccgcguacg u                                               21

<210> SEQ ID NO 154
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
gcgtaatacg actcactata ggacaagcct aattagtgat gc                        42

<210> SEQ ID NO 155
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
gaacagtatg tctcagacat c                                               21
```

<210> SEQ ID NO 156
<211> LENGTH: 41
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 156
gcgtaatacg actcactata gggctttgtt agcagccgga t          41

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 157
gggagaccac aacggtttcc c          21

<210> SEQ ID NO 158
<211> LENGTH: 31
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 158
acauuucgaa guauuccgcg uacgugaugu u          31

<210> SEQ ID NO 159
<211> LENGTH: 31
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 159
caucacguac gcggaauacu ucgaaauguc c          31

<210> SEQ ID NO 160
<211> LENGTH: 16
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 160
cguacuuuug uacgug          16

<210> SEQ ID NO 161
<211> LENGTH: 16
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 161
uguacuuuug uacgug          16

```
<210> SEQ ID NO 162
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
ucgaauuuuu cgaaa                                                        15

<210> SEQ ID NO 163
<211> LENGTH: 21
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 163
acaaauucgg aucuacaggg u                                                 21

<210> SEQ ID NO 164
<211> LENGTH: 22
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 164
aaaccucucu agaaccgaau uu                                                22
```

METHODS AND COMPOSITIONS FOR ENHANCING THE EFFICACY AND SPECIFICITY OF RNA SILENCING

RELATED APPLICATIONS

This application is continuation-in-part of U.S. Utility application Ser. No. 10/859,321, entitled "Methods and Compositions for Enhancing the Efficacy and Specificity of RNAi" (filed Jun. 2, 2004), which claims the benefit of U.S. Provisional Patent Application Ser. No. 60/475,331, entitled "Methods and Compositions for Enhancing the Efficacy and Specificity of RNAi," filed Jun. 2, 2003; U.S. Provisional Patent Application Ser. No. 60/507,928 entitled "Methods and Compositions for Enhancing the Efficacy and Specificity of RNAi," filed Sep. 30, 2003; and U.S. Provisional Patent Application Ser. No. 60/575,268 entitled "Methods and Compositions for Enhancing the Efficacy and Specificity of RNAi," filed May 28, 2004. The entire contents of the above-referenced patent applications are incorporated herein by this reference.

GOVERNMENT RIGHTS

This invention was made at least in part with government support under grant nos. R01 GM62862-01, GM65236-01, and R21 NS44952-01 awarded by the National Institutes of Health. The government may have certain rights in this invention.

BACKGROUND OF THE INVENTION

Two types of ~21 nt RNAs trigger post-transcriptional gene silencing in animals: small interfering RNAs (siRNAs) and microRNAs (miRNAs). Both siRNAs and miRNAs are produced by the cleavage of double-stranded RNA (dsRNA) precursors by Dicer, a nuclease of the RNase III family of dsRNA-specific endonucleases (Bernstein et al., 2001; Billy et al., 2001; Grishok et al., 2001; Hutvágner et al., 2001; Ketting et al., 2001; Knight and Bass, 2001; Paddison et al., 2002; Park et al., 2002; Provost et al., 2002; Reinhart et al., 2002; Zhang et al., 2002; Doi et al., 2003; Myers et al., 2003). siRNAs result when transposons, viruses or endogenous genes express long dsRNA or when dsRNA is introduced experimentally into plant or animal cells to trigger gene silencing, a process known as RNA interference (RNAi) (Fire et al., 1998; Hamilton and Baulcombe, 1999; Zamore et al., 2000; Elbashir et al., 2001a; Hammond et al., 2001; Sijen et al., 2001; Catalanotto et al., 2002). In contrast, miRNAs are the products of endogenous, non-coding genes whose precursor RNA transcripts can form small stem-loops from which mature miRNAs are cleaved by Dicer (Lagos-Quintana et al., 2001; Lau et al., 2001; Lee and Ambros, 2001; Lagos-Quintana et al., 2002; Mourelatos et al., 2002; Reinhart et al., 2002; Ambros et al., 2003; Brennecke et al., 2003; Lagos-Quintana et al., 2003; Lim et al., 2003a; Lim et al., 2003b). miRNAs are encoded by genes distinct from the mRNAs whose expression they control.

siRNAs were first identified as the specificity determinants of the RNA interference (RNAi) pathway (Hamilton and Baulcombe, 1999; Hammond et al., 2000), where they act as guides to direct endonucleolytic cleavage of their target RNAs (Zamore et al., 2000; Elbashir et al., 2001a). Prototypical siRNA duplexes are 21 nt, double-stranded RNAs that contain 19 base pairs, with two-nucleotide, 3' overhanging ends (Elbashir et al., 2001a; Nykänen et al., 2001; Tang et al., 2003). Active siRNAs contain 5' phosphates and 3' hydroxyls (Zamore et al., 2000; Boutla et al., 2001; Nykänen et al., 2001; Chiu and Rana, 2002). Similarly, miRNAs contain 5' phosphate and 3' hydroxyl groups, reflecting their production by Dicer (Hutvágner et al., 2001; Mallory et al., 2002).

In plants, miRNAs regulate the expression of developmentally important proteins, often by directing mRNA cleavage (Rhoades et al., 2002; Reinhart et al., 2002; Llave et al., 2002a; Llave et al., 2002b; Xie et al., 2003; Kasschau et al., 2003; Tang et al., 2003; Chen, 2003). Whereas plant miRNA's show a high degree of complementarity to their mRNA targets, animal miRNA's have only limited complementarity to the mRNAs whose expression they control (Lee et al., 1993; Wightman et al., 1993; Olsen and Ambros, 1999; Reinhart et al., 2000; Slack et al., 2000; Abrahante et al., 2003; Brennecke et al., 2003; Lin et al., 2003; Xu et al., 2003). Animal miRNAs are thought to repress mRNA translation, rather than promote target mRNA destruction (Lee et al., 1993; Wrightman et al., 1993; Olsen and Ambross, 1999; Brennecke et al., 2003). Recent evidence suggests that the two classes of small RNAs are functionally interchangeable, with the choice of mRNA cleavage or translational repression determined solely by the degree of complementarity between the small RNA and its target (Schwarz and Zamore, 2002; Hutvágner and Zamore, 2002; Zeng et al., 2003; Doench et al., 2003). Furthermore, siRNAs and miRNAs are found in similar, if not identical complexes, suggesting that a single, bifunctional complex—the RNA-induced silencing complex (RISC)-mediates both cleavage and translational control (Mourelatos et al., 2002; Hutvágner and Zamore, 2002; Caudy et al., 2002; Martinez et al., 2002). Nonetheless, studies in both plants and animals show that at steady-state, siRNAs and miRNAs differ in at least one crucial respect: in vivo and in vitro, siRNAs are double-stranded, whereas miRNAs are single-stranded (Lee et al., 1993; Hamilton and Baulcombe, 1999; Pasquinelli et al., 2000; Reinhart et al., 2000; Elbashir et al., 2001a; Djikeng et al., 2001; Nykänen et al., 2001; Lagos-Quintana et al., 2001; Lau et al., 2001; Lee and Ambros, 2001; Lagos-Quintana et al., 2002; Reinhart et al., 2002; Llave et al., 2002a; Silhavy et al., 2002; Llave et al., 2002b; Tang et al., 2003).

siRNA duplexes can assemble into RISC in the absence of target mRNA, both in vivo and in vitro (Tuschl et al., 1999; Hammond et al., 2000; Zamore et al., 2000). Each RISC contains only one of the two strands of the siRNA duplex (Martinez et al., 2002). Since siRNA duplexes have no foreknowledge of which siRNA strand will guide target cleavage, both strands must assemble with the appropriate proteins to form a RISC. Previously, we and others showed that both siRNA strands are competent to direct RNAi (Tuschl et al., 1999; Hammond et al., 2000; Zamore et al., 2000; Elbashir et al., 2001b; Elbashir et al., 2001a; Nykänen et al., 2001). That is, the anti-sense strand of an siRNA can direct cleavage of a corresponding sense RNA target, whereas the sense siRNA strand directs cleavage of an anti-sense target. In this way, siRNA duplexes appear to be functionally symmetric. The ability to control which strand of an siRNA duplex enters into the RISC complex to direct cleavage of a corresponding RNA target would provide a significant advance for both research and therapeutic applications of RNAi technology.

SUMMARY OF THE INVENTION

A key step in RNA interference (RNAi) is the assembly of a catalytically active protein-RNA complex, the RNA-induced silencing complex (RISC), that mediates target RNA cleavage. The instant invention is based, at least in part, on the discovery that the two strands of a siRNA duplex do not contribute equally to RISC assembly. Rather, both the absolute and the relative stabilites of the base pairs at the 5' ends of the two siRNA strands determines the degree to which each strand participates in the RNAi pathway. In fact, siRNA can be functionally asymmetric, with only one of the two strands able to trigger RNAi. The present invention is also based on the discovery that single stranded miRNAs are initially generated as siRNA-like duplexes whose structures predestine one strand to enter the RISC and the other strand to be destroyed. This finding helps to explain the biogenesis of single-stranded miRNAs; the miRNA strand of a short-lived, siRNA duplex-like intermediate is assembled into a RISC complex, causing miRNAs to accumulate in vivo as single-stranded RNAs.

The present invention is further based on the discovery that RISC can cleave RNA targets with up to five contiguous mismatches at the siRNA 5' end and eight mismatches at the siRNA 3' end, indicating that 5' bases contribute disproportionately to target RNA binding, but do not play a role in determining the catalytic rate, kcat. This finding explains how the 5', central and 3' sequences of the siRNA guide strand function to direct target cleavage.

The invention is further based on the discovery that the 3' bases of the siRNA contribute much less than 5' bases to the overall strength of binding, but instead help to establish the helical geometry required for RISC-mediated target cleavage, consistent with the view that catalysis by RISC requires a central A-form helix (Chiu et al., 2003). This finding indicates that complementarity is essential for translational repression by siRNAs designed to act like animal miRNAs, which typically repress translation (Doench et al., 2004).

The present invention is further based on the discovery that when an siRNA fails to pair with the first three, four or five nucleotides of the target RNA, the phosphodiester bond severed in the target RNA is unchanged; for perfectly matched siRNA, RISC measures the site of cleavage from the siRNA 5' end (Elbashir et al., 2001; Elbashir et al., 2001). This finding indicates that the identity of the scissile phosphate is determined prior to the encounter of the RISC with its target RNA, perhaps because the RISC endonuclease is positioned with respect to the siRNA 5' end during RISC assembly.

Accordingly, the instant invention features methods of enhancing the efficacy and specificity of RNAi. Also provided is a method of decreasing silencing of an inadvertent target by an RNAi agent. The invention further features compositions, including siRNAs, shRNAs, as well as vectors and transgenes, for mediating RNAi. The RNAi agents of the invention have improved specificity and efficacy in mediating silencing of a target gene.

The design rules for enhancing the efficacy and specificity of RNAi agents can also be applied to other RNA silencing agents, in particular agents that mediate translational repression of a target gene. Such silencing agents include, for example, siRNA-like duplexes that include a miRNA strand, as described supra. Methods featuring such silencing agents are also described herein.

Other features and advantages of the invention will be apparent from the following detailed description and claims.

BRIEF DESCRIPTION OF THE DRAWINGS

FIG. 1. RNAi mediated by asymmetric duplex and single-stranded siRNAs. (A) Schematic showing relevant portions of the sense and anti-sense target RNA sequences (SEQ ID NOS 1 & 2). (B) Schematic showing siRNA duplex sequence (SEQ ID NOS 3 & 4) and graph depicting RNAi mediated by the antisense and sense strands. (C) Schematic showing siRNA sequences of individual single strands (SEQ ID NOS 3 & 4) and graph depicting RNAi mediated by the single strands. (D) Bar graph depicting fraction of total siRNA present as single-strand. (E) Schematic showing siRNA duplex sequence (SEQ ID NOS 5 & 4) containing G:U wobble base pair and graph depicting RNAi mediated by the antisense and sense strands.

FIG. 2. RNAi mediated by asymmetric duplex siRNAs. (A) Schematic showing relevant portions of the sense and antisense target RNA sequences (SEQ ID NOS 6 & 7). (B) Schematic showing siRNA duplex sequence (bases 13-33 of SEQ ID NO: 1 & SEQ ID NO: 8) and graph depicting RNAi mediated by the antisense and sense strands. (C) Schematic showing siRNA duplex sequence (SEQ ID NOS 9 & 10) containing A:U mismatch and graph depicting RNAi mediated by the antisense and sense strands. (D) Schematic showing siRNA duplex sequence (SEQ ID NOS 9 & 8) containing G:U mismatch and graph depicting RNAi mediated by the antisense and sense strands. (E) Schematic showing siRNA duplex sequence (bases 13-33 of SEQ ID NO: 1 & SEQ ID NO: 10) containing C:A mismatch and graph depicting RNAi mediated by the antisense and sense strands.

FIG. 3. RNAi mediated by asymmetric duplex siRNAs. (A) Schematic showing relevant portions of the sense and antisense target RNA sequences (SEQ ID NOS 11 & 12). (B) Schematic showing siRNA duplex sequence (SEQ ID NOS 13 & 14) and graph depicting RNAi mediated by the antisense and sense strands. (C) Schematic showing siRNA duplex sequence (SEQ ID NOS 15 & 14) containing A:G mismatch and graph depicting RNAi mediated by the antisense and sense strands. (D) Schematic showing siRNA duplex sequence (SEQ ID NOS 13 & 16) containing C:U mismatch and graph depicting RNAi mediated by the antisense and sense strands. (E) Schematic showing siRNA duplex sequence (SEQ ID NOS 15 & 16) containing A:U base pair and graph depicting RNAi mediated by the antisense and sense strands. (F) Schematic showing siRNA duplex sequence (SEQ ID NOS 13 & 17) containing A:G mismatch and graph depicting RNAi mediated by the antisense and sense strands. (G) Schematic showing siRNA duplex sequence (SEQ ID NOS 18 & 14) containing C:U mismatch and graph depicting RNAi mediated by the antisense and sense strands. (H) Schematic showing siRNA duplex sequence (SEQ ID NOS 18 & 17) containing A:U base pair and graph depicting RNAi mediated by the antisense and sense strands. (I) Schematic of individual single-strands of siRNAs (SEQ ID NOS 14, 16, 15, & 13 respectively in order of appearance) and graph depicting RNAi mediated by the individual single-strands.

FIG. 4. RNAi mediated by asymmetric duplex siRNAs containing inosine. (A) Schematic showing siRNA duplex sequence (SEQ ID NOS 19 & 14) having inosine at 5' end of sense strand and graph depicting RNAi mediated by the antisense and sense strands. (B) Schematic showing siRNA duplex sequence (SEQ ID NOS 13 & 20) having inosine at 5' end of antisense strand and graph depicting RNAi mediated by the antisense and sense strands. (C) Schematic showing siRNA duplex sequence (SEQ ID NOS 19 & 20) containing insoine in both strands and graph depicting RNAi mediated by the antisense and sense strands. (D) Schematic showing individual siRNA strands (SEQ ID NOS 19 & 20) containing inosine and graph depicting RNAi mediated by the individual single-strands.

FIG. 5. Symmetric cleavage of pre-let-7 by Dicer. (A) Analysis of cleavage products produced on 5' side of precursor stem (let-7). (B) Analysis of cleavage products produced on 3' side of precursor stem (let-7*). (C) Conceptual dicing of pre-let-7 (SEQ ID NO: 21) to a deduced pre-let-7 siRNA (SEQ ID NOS 22 & 23).

FIG. 8. Reduction of off-target silencing by sense strand. (A) Sense and anti-sense sod1 target RNA sequences (SEQ ID NOS 73 & 74). (B) Schematic showing siRNA duplex sequence (SEQ ID NOS 75 & 76) and graph depicting RNAi mediated by the antisense and sense strands. (C) Schematic showing siRNA duplex sequence (SEQ ID NOS 75 & 77) containing G:U wobble base pair and graph depicting RNAi mediated by the antisense and sense strands. (D) Schematic showing individual siRNA strands (SEQ ID NOS 75-77) and graph depicting RNAi mediated by the individual single-strands. (E) Thermodynamic analysis of siRNA strand 5' ends for the siRNA duplex in (B). G (kcal/mole) was calculated in 1M NaCl at 37° C.

FIG. 9. Enhancement of silencing by antisense strand. (A) Schematic showing relevant portions of the sense (SEQ ID NO: 78) and anti-sense (SEQ ID NO: 79) target RNA sequences. (B) Schematic showing siRNA duplex sequence (SEQ ID NOS 80 & 81) and graph depicting RNAi mediated by the antisense and sense strands. (C) Schematic showing siRNA duplex sequence (SEQ ID NOS 82 & 83) containing A:U base pair and graph depicting RNAi mediated by the antisense and sense strands. (D) Schematic showing siRNA duplex sequence (SEQ ID NOS 82 & 81) containing A:G mismatch and graph depicting RNAi mediated by the antisense and sense strands. (E) Thermodynamic analysis of siRNA strand 5' ends for the siRNA duplex in (B). G (kcal/mole) was calculated in 1M NaCl at 37° C.

FIG. 10. The relative thermodynamic stability of the first four base pairs of the siRNA strands (SEQ ID NOS 3-5) explains siRNA functional asymmetry. Thermodynamic analysis of siRNA strand 5' ends for the siRNAs in FIGS. 1B and 1E. G (kcal/mole) was calculated in 1M NaCl at 37° C.

FIG. 15. Remarkable tolerance of RISC for 3' mismatches. (a) Each additional 3' mismatch further reduced the rate of cleavage by RISC. The steady-state rates of cleavage were determined for siRNA with zero, one, two, and four mismatches under multiple-turnover conditions (~49 nM target mRNA and ~4-6 nM RISC). (b) Analysis of siRNAs bearing zero to five 3' mismatches with the target RNA under conditions of slight enzyme excess (~2-fold more RISC than target). siRNA sequences and corresponding target RNA sequences used in (a) and (b) are shown in FIG. 14A and FIG. 21A. (c) Extended endpoint analysis of RISC cleavage under conditions of ~80-fold enzyme excess reveals that cleavage can occur for siRNAs with as many as eight mismatches to the target RNA. Note the different time scales in (c) versus (b). All reactions were under standard in vitro RNAi (+ATP) conditions. siRNA sequences and corresponding target RNA sequences used in (c) are shown in FIG. 21B.

FIG. 19. Exogenously programmed RISC is a bona fide enzyme siRNA was assembled into RISC for 1 hour in a standard in vitro RNAi reaction, then assembly was quenched with N-ethyl maleimide (NEM)21,29. The amount of RISC formed was determined by measuring 32P-radiolabeled siRNA retained on a tethered 5'-biotinylated, 31-nt, 2'-O-methyl oligonucleotide complementary to the guide strand of the siRNA. RISC binds essentially irreversibly to tethered 2'-O-methyl oligonucleotides, but cannot cleave these RNA-analogs (Hutvàgner et al., 2004; Schwartz et al., 2003). In all experiments, target-cleaving activity was not detected in the supernatant, demonstrating that all the active RISC was retained on the beads. (a) Sequence of the siRNA used (SEQ ID NOS 93 & 94) (guide strand in red, 32P-radiolabel marked with an asterisk). Drosophila let-7 is not expressed in 0-2 hour embryos (Hutvàgner et al., 2001), so the only source of let-7 in the in vitro reactions was the exogenous let-7 siRNA. The 5' end of the guide strand of the let-7 siRNA is predicted to be thermodynamically more stable than the 5' end of the passenger strand, explaining why only a low concentrations of let-7-programmed RISC is formed (Schwartz et al., 2003; Khvorova et al., 2003). The maximum amount of RISC assembled varies widely with siRNA sequence. The siRNAs used in FIGS. 3-8 were designed to load=5-fold more guide strand-containing RISC (Hutvàgner et al., 2001; Schwartz et al., 2003) (b) Representative gel confirming that the RISC was removed by the tethered 2'-O-methyl oligonucleotide. A reaction prior to incubation with the tethered 2'-O-methyl oligonucleotide (pre) was compared to the supernatant of a reaction incubated with beads alone (mock), and the supernatant of a reaction incubated with the complementary tethered 2'-O-methyl oligonucleotide (post). The buffer reaction contained no siRNA. (c) Analysis of the amount of RISC assembled at various siRNA concentrations. 5' 32P-radiolabeled siRNA was incubated with lysate for 1 hour, then reactions were quenched by treatment with NEM, and RISC concentration was measured using the tethered 2'-O-methyl oligonucleotide method.

FIG. 21. siRNAs, target sites, and 2'-O-methyl oligonucleotides (SEQ ID NOS 92-143) used in this study. (a) List of siRNA and corresponding target RNA sequences used in the experiments described in Table 1 and FIGS. 14B-D, 15A, 15B, 17A, and 20A. (b) List of siRNA and corresponding target RNA sequences used in the experiment described in FIG. 15C. (c) List of siRNA and corresponding target RNA sequences used in the experiment described in FIG. 16C. (d) List of siRNAs and corresponding target 2'-O-methyl oligonucleotide sequences used in the experiments described in FIGS. 17B and 20B. (e)-(g) List of siRNA and corresponding target RNA sequences used in the experiments described in FIGS. 16A, 16D, 17A, and Table 1. (h) List of siRNA and corresponding target RNA sequences used in the experiment described in FIG. 16B.

DETAILED DESCRIPTION OF THE INVENTION

Figure 6A:
FIG. 6. Analysis of *Drosphila* miRNA genes for predicted miRNA and miRNA*. (A) Conceptual dicing of 26 published *Drosphila* miRNA genes to a deduced duplex siRNA (SEQ ID NOS 24-72). (B) Amounts of miR-10 and miR-10* detected in vivo.
Figure 6B:
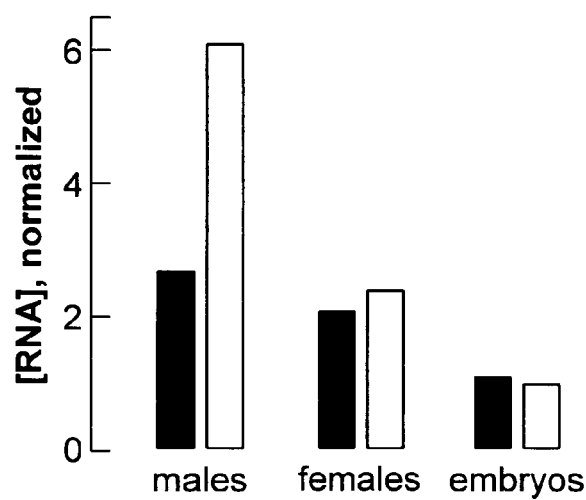
Figure 7:
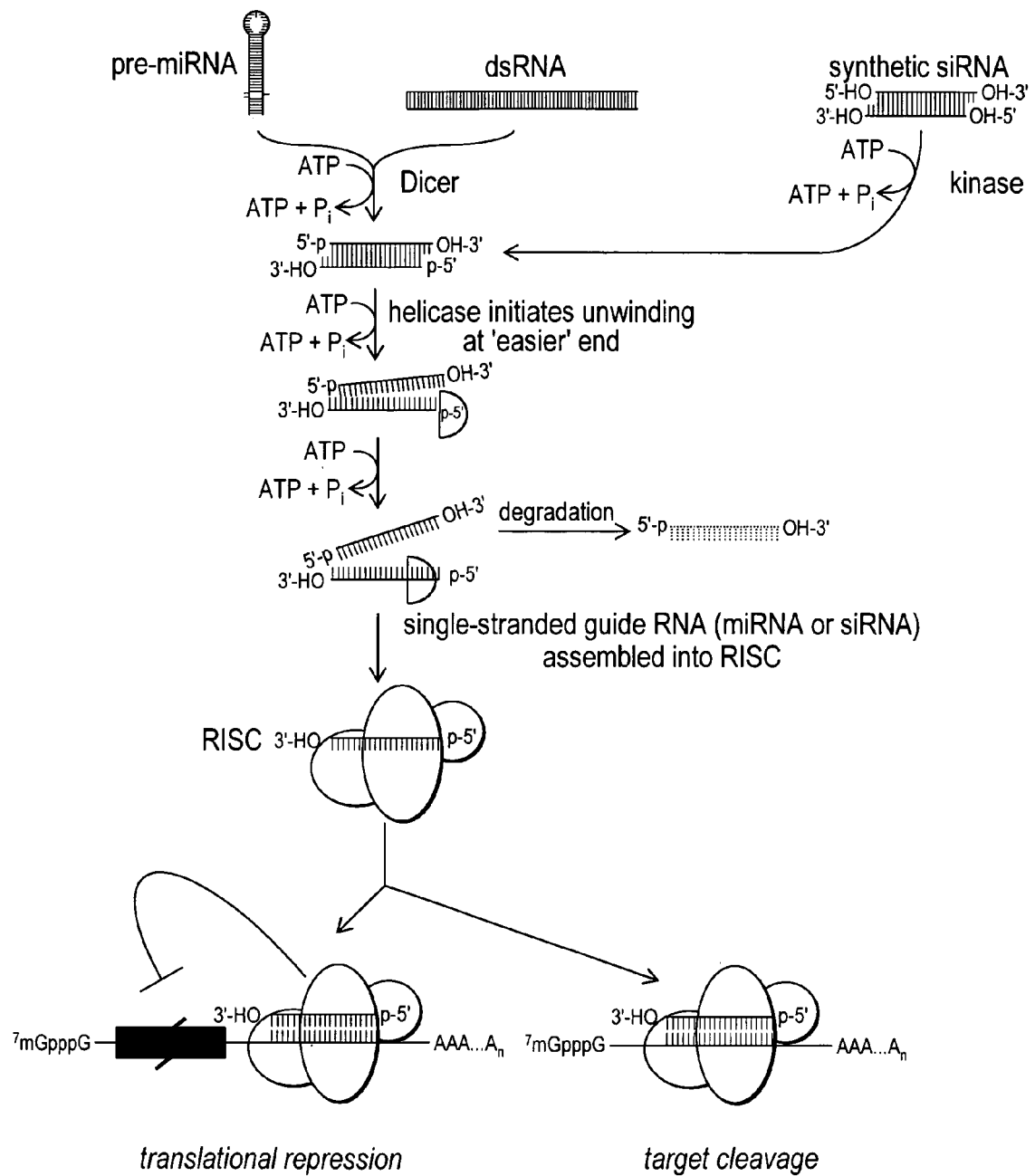
FIG. 7. Schematic representing mechanism of RISC assembly from pre-miRNA or dsRNA.
Figure 11D:
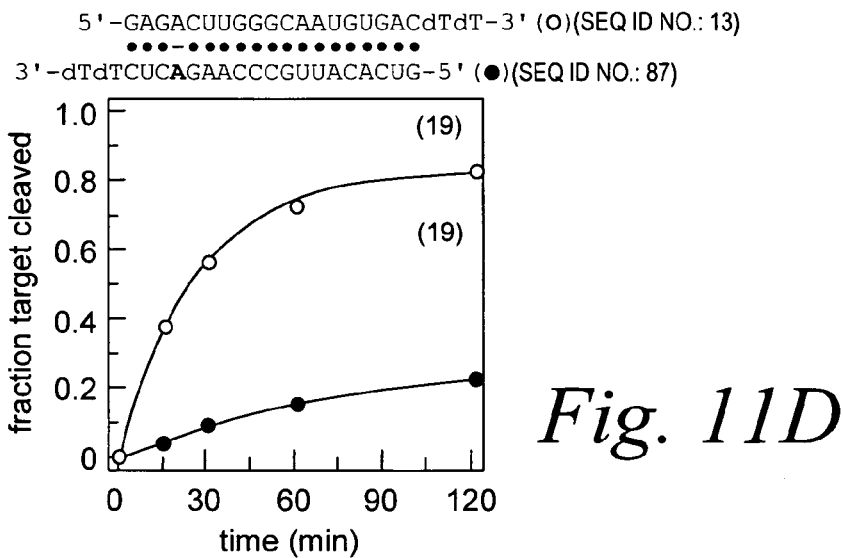
FIG. 11. The first four base pairs of the siRNA duplex determine strand-specific activity. Internal, single-nucleotide mismatches (A-F) (SEQ ID NOS 13, 14, & 84-89) near the 5' ends of an siRNA strand generate functional asymmetry, but internal G:U wobble pairs (G-I) (SEQ ID NOS 13, 14, 90, & 91) do not.
Figure 11E:
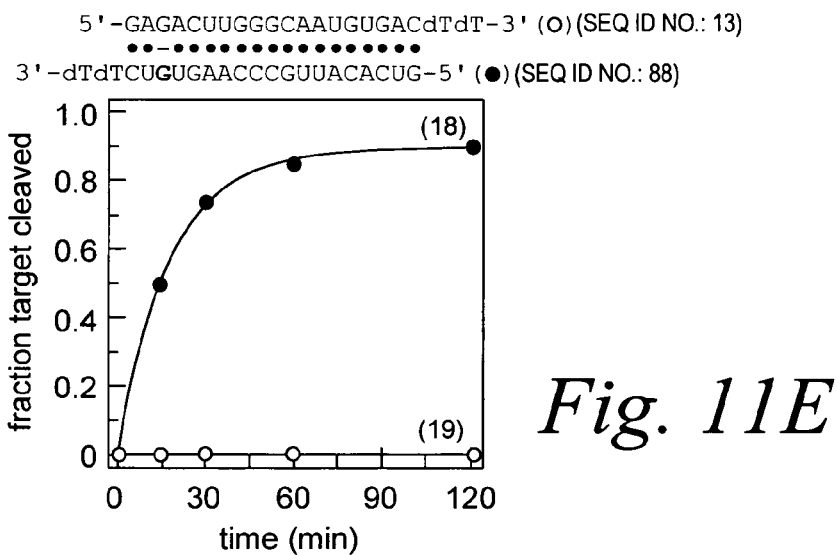
Figure 11F:
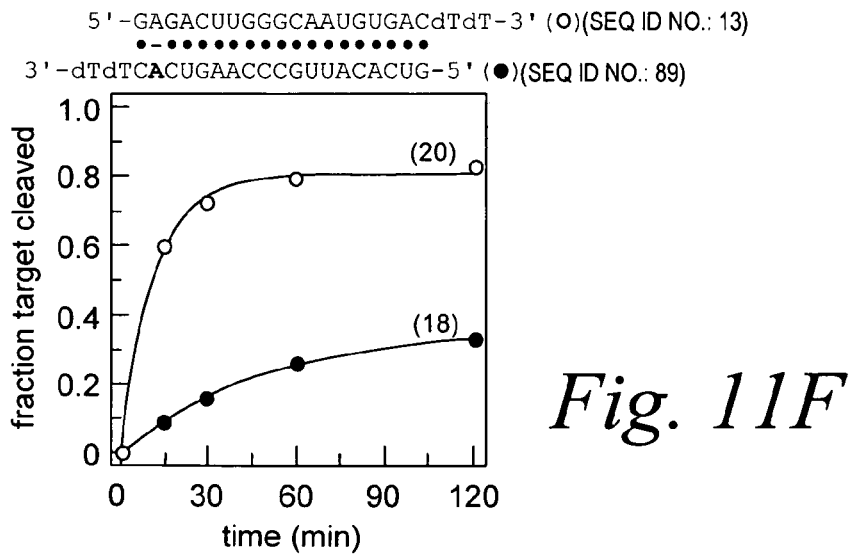
Figure 11G:
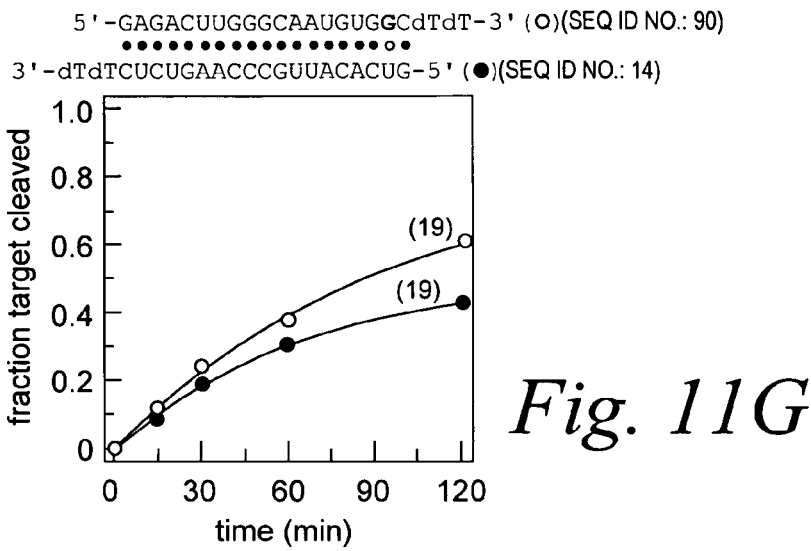
Figure 11H:
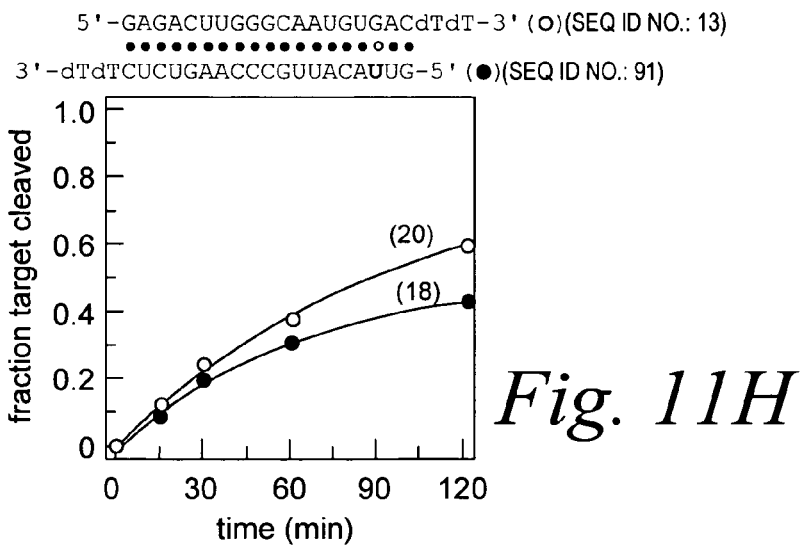
Figure 11I:
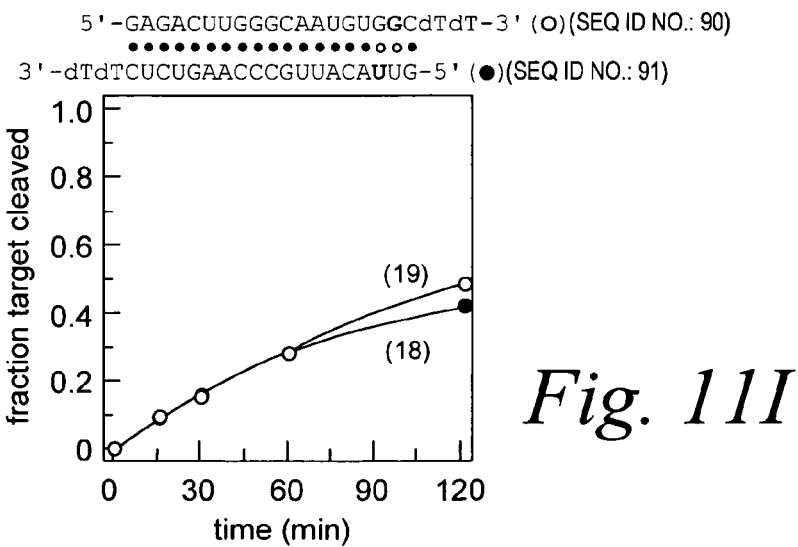

A key step in RNA interference (RNAi) is the assembly of a catalytically active protein-RNA complex, the RNA-induced silencing complex (RISC), that mediates target RNA cleavage. Each RISC contains one of the two strands of the small interfering RNA (siRNA) duplex that triggers RNAi. The instant invention is based, at least in part, on the discovery that the two siRNA strands do not contribute equally to RISC assembly. Small changes in siRNA sequence were found to have profound and predictable effects on the extent to which the two strands of an siRNA duplex enter the RNAi pathway, a phenomenon termed siRNA functional "asymmetry". The discoveries described herein reveal that the strength of the base-pairing interactions made by the 5' end of each siRNA strand with the 3' region of strand to which it is paired determines which of the two strands participates in the RNAi pathway. RISC assembly appears to be governed by an enzyme that initiates unwinding of an siRNA duplex at the siRNA strand whose 5' end is less tightly paired to the complementary siRNA strand.

Remarkably, such highly asymmetric siRNA duplexes resemble proposed intermediates in the biogenesis pathway of microRNA (miRNA) (Hutvágner and Zamore, 2002; Reinhart et al., 2002; Lim et al., 2003b). miRNAs are endogenous, ~21-nt single-stranded RNAs processed by Dicer from stem-loop RNA precursors that regulate gene expression in animals and plants. A striking feature of miRNA precursors is their lack of full complementarity in the stem region. The discoveries presented herein indicate an important role for the discontinuities in the stem region of miRNAs; it is likely that miRNAs are initially generated from their precursor RNAs as siRNA-like duplexes, and that the structure of these duplexes predestines the miRNA strand to enter the RISC and the other strand to be destroyed. Thus, nature appears to have optimized the stem portion of miRNAs to follow a set of rules dictating which strand enters the RISC complex.

The discoveries made by the instant inventors provide rules according to which siRNAs and shRNAs can be designed that are fully asymmetric, with only one of the two siRNA strands competent to enter the RISC complex. By applying these rules to the selection and design of a targeted RNAi agent, e.g., siRNAs and shRNAs, the antisense strand of the RNAi agent can be predictably directed to enter the RISC complex and mediate target RNA cleavage. Similarly, the sense strand can be discouraged from entering the RISC complex, thereby reducing or eliminating undesired silencing of an inadvertent target by the sense strand.

Accordingly, the instant invention provides methods for improving the efficiency (or specificity) of an RNAi reaction comprising identifying an off target RNAi activity mediated by the sense strand of an RNAi agent, and modifying the RNAi agent such that the base pair strength between the 5' end of the antisense strand and the 3' end of the sense strand is lessened relative to the base pair strength of the 5' end of the sense strand and the 3' end of the antisense strand (e.g., relative to the premodified RNAi agent), such that the sense strand is less effective at entering RISC (e.g., less effective than the premodified RNAi agent).

The instant invention also provides methods for improving the efficiency (or specificity) of an RNAi reaction comprising modifying (e.g., increasing) the asymmetry of the RNAi agent such that the ability of the sense or second strand to mediate RNAi (e.g., mediate cleavage of target RNA) is lessened. In preferred embodiments, the asymmetry is increased in favor of the 5' end of the first strand, e.g., lessening the bond strength (e.g., the strength of the interaction) between the 5' end of the first strand and 3' end of the second strand relative to the bond strength (e.g., the strength of the interaction) between the 5' end of the second strand and the 3' end of the first strand. In other embodiments, the asymmetry is increased in favor of the 5' end of the first strand by increasing bond strength (e.g., the strength of the interaction) between the 5' end of the second or sense strand and the 3' end of the first or antisense strand, relative to the bond strength (e.g., the strength of the interaction) between the 5' end of the first and the 3' end of the second strand. In embodiments of the invention, the bond strength is increased, e.g., the H bonding is increased between nucleotides or analogs at the 5' end, e.g., within 5 nucleotides of the second or sense strand (numbered from the 5' end of the second strand) and complementary nucleotides of the first or antisense strand. It is understood that the asymmetry can be zero (i.e., no asymmetry), for example, when the bonds or base pairs between the 5' and 3' terminal bases are of the same nature, strength or structure. More routinely, however, there exists some asymmetry due to the different nature, strength or structure of at least one nucleotide (often one or more nucleotides) between terminal nucleotides or nucleotide analogs.

Accordingly, in one aspect, the instant invention provides a method of enhancing the ability of a first strand of a RNAi agent to act as a guide strand in mediating RNAi, involving lessening the base pair strength between the 5' end of the first strand and the 3' end of a second strand of the duplex as compared to the base pair strength between the 3' end of the first strand and the 5' end of the second strand.

In a related aspect, the invention provides a method of enhancing the efficacy of a siRNA duplex, the siRNA duplex comprising a sense and an antisense strand, involving lessening the base pair strength between the antisense strand 5' end (AS 5') and the sense strand 3' end (S 3') as compared to the base pair strength between the antisense strand 3' end (AS 3') and the sense strand 5' end (S '5), such that efficacy is enhanced.

In another aspect of the invention, a method is provided for promoting entry of a desired strand of an siRNA duplex into a RISC complex, comprising enhancing the asymmetry of the siRNA duplex, such that entry of the desired strand is promoted. In one embodiment of this aspect of the invention, the asymmetry is enhanced by lessening the base pair strength between the 5' end of the desired strand and the 3' end of a complementary strand of the duplex as compared to the base pair strength between the 3' end of the desired strand and the 5' end of the complementary strand.

In another aspect of the invention, a siRNA duplex is provided comprising a sense strand and an antisense strand, wherein the base pair strength between the antisense strand 5' end (AS 5') and the sense strand 3' end (S 3') is less than the base pair strength between the antisense strand 3' end (AS 3') and the sense strand 5' end (S '5), such that the antisense strand preferentially guides cleavage of a target mRNA.

In one embodiment of these aspects of the invention, the base-pair strength is less due to fewer G:C base pairs between the 5' end of the first or antisense strand and the 3' end of the second or sense strand than between the 3' end of the first or antisense strand and the 5' end of the second or sense strand.

In another embodiment, the base pair strength is less due to at least one mismatched base pair between the 5' end of the first or antisense strand and the 3' end of the second or sense strand. Preferably, the mismatched base pair is selected from the group consisting of G:A, C:A, C:U, G:G, A:A, C:C and U:U.

In one embodiment, the base pair strength is less due to at least one wobble base pair, e.g., G:U, between the 5' end of the first or antisense strand and the 3' end of the second or sense strand.

In another embodiment, the base pair strength is less due to at least one base pair comprising a rare nucleotide, e.g, inosine (I). Preferably, the base pair is selected from the group consisting of an I:A, I:U and I:C.

In yet another embodiment, the base pair strength is less due to at least one base pair comprising a modified nucleotide. In preferred embodiments, the modified nucleotide is selected from the group consisting of 2-amino-G, 2-amino-A, 2,6-diamino-G, and 2,6-diamino-A.

In several embodiments of these aspects of the invention, the RNAi agent is a siRNA duplex or is derived from an engineered precursor, and can be chemically synthesized or enzymatically synthesized.

In another aspect of the instant invention, compositions are provided comprising a siRNA duplex of the invention formulated to facilitate entry of the siRNA duplex into a cell. Also provided are pharmaceutical composition comprising a siRNA duplex of the invention.

Further provided are an engineered pre-miRNA comprising a siRNA duplex as described above, as well as a vector encoding the pre-miRNA. In related aspects, the invention provides a pri-miRNA comprising the pre-miRNA, as well as a vector encoding the pri-miRNA.

Also featured in the instant invention are small hairpin RNA (shRNA) comprising nucleotide sequence identical to the sense and antisense strand of the siRNA duplexes as described above. In one embodiment, the nucleotide sequence identical to the sense strand is upstream of the nucleotide sequence identical to the antisense strand. In another embodiment, the nucleotide sequence identical to the antisense strand is upstream of the nucleotide sequence identical to the sense strand. Further provided are vectors and transgenes encoding the shRNAs of the invention.

In yet another aspect, the invention provides cells comprising the vectors featured in the instant invention. Preferably, the cell is a mammalian cell, e.g., a human cell.

In other aspects of the invention, methods of enhancing silencing of a target mRNA, comprising contacting a cell having an RNAi pathway with a RNAi agent as described above under conditions such that silencing is enhanced.

Also provided are methods of enhancing silencing of a target mRNA in a subject, comprising administering to the subject a pharmaceutical composition comprising a RNAi agent as described above such that silencing is enhanced.

Further provided is a method of decreasing silencing of an inadvertant target mRNA by a dsRNAi agent, the dsRNAi agent comprising a sense strand and an antisense strand involving the steps of: (a) detecting a significant degree of complementarity between the sense strand and the inadvertant target; and (b) enhancing the base pair strength between the 5' end of the sense strand and the 3' end of the antisense strand relative to the base pair strength between the 3' end of the sense strand and the 5' end of the antisense strand; such that silencing of the inadvertant target mRNA is decreased. In a preferred embodiment, the silencing of the inadvertant target mRNA is decreased relative to silencing of a desired target mRNA.

The design rules described supra can also be applied to other classes of RNA silencing agents, for example, siRNA-like duplexes that include a miRNA strand. In particular, the design rules can be applied to such siRNA-like duplexes to promote entry of the desired strand of the duplex (e.g., the miRNA strand) into a RISC complex. The degree of complementarity between the miRNA strand and its target determines whether the small RNA mediates mRNA cleavage or translational repression, as described supra. Such duplexes are useful for effectively delivering miRNAs, for example, to cells or animals for therapeutic purposes.

Accordingly, in one aspect, the instant invention provides a method of enhancing the ability of a first strand of a siRNA-like duplex to act in mediating RNA silencing (e.g., RNAi or translational repression), involving lessening the base pair strength between the 5' end of the first strand and the 3' end of a second strand of the duplex as compared to the base pair strength between the 3' end of the first strand and the 5' end of the second strand.

In a related aspect, the invention provides a method of enhancing the efficacy of a siRNA-like duplex, the siRNA-like duplex comprising a miRNA and an miRNA* strand, involving lessening the base pair strength between the miRNA strand 5' end (miRNA 5') and the miRNA* strand 3' end (miRNA* 3') as compared to the base pair strength between the miRNA strand 3' end (miRNA 3') and the miRNA* strand 5' end (miRNA* 5'), such that efficacy is enhanced.

In another aspect of the invention, a method is provided for promoting entry of a desired strand of an siRNA-like duplex into a RISC complex, comprising enhancing the asymmetry of the siRNA duplex, such that entry of the desired strand is promoted. In one embodiment of this aspect of the invention, the asymmetry is enhanced by lessening the base pair strength between the 5' end of the desired strand and the 3' end of a complementary strand of the duplex as compared to the base pair strength between the 3' end of the desired strand and the 5' end of the complementary strand.

In another aspect of the invention, a siRNA-like duplex is provided comprising a miRNA strand and an miRNA* strand, wherein the base pair strength between the miRNA strand 5' end (miRNA 5') and the miRNA* strand 3' end (miRNA* 3') is less than the base pair strength between the miRNA strand 3' end (miRNA 3') and the miRNA* strand 5' end (miRNA* 5'), such that the miRNA strand preferentially silences (e.g., cleaves or represses) a target mRNA.

In one embodiment of these aspects of the invention, the base-pair strength is less due to fewer G:C base pairs between the 5' end of the first or miRNA strand and the 3' end of the second or miRNA* strand than between the 3' end of the first or miRNA strand and the 5' end of the second or miRNA* strand.

In another embodiment, the base pair strength is less due to at least one mismatched base pair between the 5' end of the first or miRNA strand and the 3' end of the second or miRNA* strand. Preferably, the mismatched base pair is selected from the group consisting of G:A, C:A, C:U, G:G, A:A, C:C and U:U.

In one embodiment, the base pair strength is less due to at least one wobble base pair, e.g., G:U, between the 5' end of the first or miRNA strand and the 3' end of the second or miRNA* strand.

In another embodiment, the base pair strength is less due to at least one base pair comprising a rare nucleotide, e.g, inosine (I). Preferably, the base pair is selected from the group consisting of an I:A, I:U and I:C.

In yet another embodiment, the base pair strength is less due to at least one base pair comprising a modified nucleotide. In preferred embodiments, the modified nucleotide is selected from the group consisting of 2-amino-G, 2-amino-A, 2,6-diamino-G, and 2,6-diamino-A.

In several embodiments of these aspects of the invention, the RNA silencing agent is a siRNA-like duplex or is derived from an engineered precursor, and can be chemically synthesized or enzymatically synthesized.

In another aspect of the instant invention, compositions are provided comprising a siRNA-like duplex of the invention formulated to facilitate entry of the siRNA-like duplex into a cell. Also provided are pharmaceutical composition comprising a siRNA-like duplex of the invention.

Further provided are an engineered pre-miRNA comprising the siRNA-like duplex as described above, as well as a vector encoding the pre-miRNA. In related aspects, the invention provides a pri-miRNA comprising the pre-miRNA, as well as a vector encoding the pri-miRNA.

Also featured in the instant invention are small hairpin RNA (shRNA) comprising nucleotide sequence identical to the miRNA and miRNA* strand of the siRNA-like duplex as described above. In one embodiment, the nucleotide sequence identical to the miRNA strand is upstream of the nucleotide sequence identical to the miRNA* strand. In another embodiment, the nucleotide sequence identical to the miRNA* strand is upstream of the nucleotide sequence identical to the miRNA strand. Further provided are vectors and transgenes encoding the shRNAs of the invention.

In yet another aspect, the invention provides cells comprising the vectors featured in the instant invention. Preferably, the cell is a mammalian cell, e.g., a human cell.

In other aspects of the invention, methods of enhancing silencing of a target mRNA, comprising contacting a cell having an RNA silencing pathway with the RNA silencing agent as described above under conditions such that silencing is enhanced.

Also provided are methods of enhancing silencing of a target mRNA in a subject, comprising administering to the subject a pharmaceutical composition comprising the RNA silencing agent as described above such that silencing is enhanced.

Further provided is a method of decreasing silencing of an inadvertant target mRNA by a dsRNA silencing agent, the dsRNA silencing agent (e.g., a siRNA-like duplex) comprising a miRNA strand and a miRNA* strand involving the steps of: (a) detecting a significant degree of complementarity between the miRNA* strand and the inadvertant target; and (b) enhancing the base pair strength between the 5' end of the miRNA* strand and the 3' end of the miRNA strand relative to the base pair strength between the 3' end of the miRNA* strand and the 5' end of the miRNA strand; such that silencing of the inadvertant target mRNA is decreased. In a preferred embodiment, the silencing of the inadvertant target mRNA is decreased relative to silencing of a desired target mRNA.

'So that the invention may be more readily understood, certain terms are first defined.

The term "nucleoside" refers to a molecule having a purine or pyrimidine base covalently linked to a ribose or deoxyribose sugar. Exemplary nucleosides include adenosine, guanosine, cytidine, uridine and thymidine. The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms.

The term "RNA" or "RNA molecule" or "ribonucleic acid molecule" refers to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein, the term "RNA silencing agent" refers to an RNA which is capable of preventing complete processing (e.g, the full translation and/or expression) of a mRNA molecule through a post-transcriptional silencing mechanism. RNA silencing agents include small (<50 b.p.), noncoding RNA molecules, for example RNA duplexes comprising paired strands, as well as precursor RNAs from which such small non-coding RNAs can be generated. Exemplary RNA silencing agents include siRNAs, miRNAs, and siRNA-like duplexes, as well as precursors thereof.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference. Preferably, an siRNA comprises between about 15-30 nucleotides or nucleotide analogs, more preferably between about 16-25 nucleotides (or nucleotide analogs), even more preferably between about 18-23 nucleotides (or nucleotide analogs), and even more preferably between about 19-22 nucleotides (or nucleotide analogs) (e.g., 19, 20, 21 or 22 nucleotides or nucleotide analogs).

As used herein, the term "microRNA" ("miRNA"), also referred to in the art as "small temporal RNAs" ("stRNAs"), refers to a small (10-50 nucleotide) RNA which is capable of directed or mediating RNA silencing. A "natural miRNA" refers to a microRNA that occurs naturally. An "miRNA disorder" shall refer to a disease or disorder characterized by a aberrant expression or activity of a natural miRNA.

As used herein, the term "rare nucleotide" refers to a naturally occurring nucleotide that occurs infrequently, including naturally occurring deoxyribonucleotides or ribonucleotides that occur infrequently, e.g., a naturally occurring ribonucleotide that is not guanosine, adenosine, cytosine, or uridine. Examples of rare nucleotides include, but are not limited to, inosine, 1-methyl inosine, pseudouridine, 5,6-dihydrouridine, ribothymidine, $^2$N-methylguanosine and $^{2,2}$N,N-dimethylguanosine.

The term "nucleotide analog" or "altered nucleotide" or "modified nucleotide" refers to a non-standard nucleotide, including non-naturally occurring ribonucleotides or deoxyribonucleotides. Preferred nucleotide analogs are modified at any position so as to alter certain chemical properties of the nucleotide yet retain the ability of the nucleotide analog to perform its intended function. Examples of preferred modified nucleotides include, but are not limited to, 2-amino-guanosine, 2-amino-adenosine, 2,6-diamino-guanosine and 2,6-diamino-adenosine. Examples of positions of the nucleotide which may be derivitized include the 5 position, e.g, 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, *Antisense Nucleic Acid Drug Dev.*, 2000 August 10(4):297-310.

Nucleotide analogs may also comprise modifications to the sugar portion of the nucleotides. For example the 2' OH-group may be replaced by a group selected from H, OR, R, F, Cl, Br, I, SH, SR, $NH_2$, NHR, $NR_2$, COOR, or OR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, *Antisense Nucleic Acid Drug Dev.* 2000 April 10(2): 117-21, Rusckowski et al. *Antisense Nucleic Acid Drug Dev.* 2000 October 10(5):333-45, Stein, *Antisense Nucleic Acid Drug Dev.* 2001 October 11(5): 317-25, Vorobjev et al. *Antisense Nucleic Acid Drug Dev.* 2001 April 11(2): 77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vitro.

The term "oligonucleotide" refers to a short polymer of nucleotides and/or nucleotide analogs. The term "RNA analog" refers to an polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, phosphorodiamidate, phophoroamidate, and/or phosphorothioate linkages. Preferred RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference.

As used herein, the term "RNA interference" ("RNAi") (also referred to in the art as "gene silencing" and/or "target silencing", e.g., "target mRNA silencing") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. As used herein, the term "translational repression" refers to a selective inhibition of mRNA translation. Natural translational repression proceeds via miRNAs cleaved from shRNA precursors. Both RNAi and translational repression are mediated by RISC. Both RNAi and translational repression occur naturally or can be initiated by the hand of man, for example, to silence the expression of target genes.

As used herein, the term "antisense strand" of an siRNA or RNAi agent refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific RNA interference (RNAi), e.g., complementarity sufficient to trigger the destruction of the desired target mRNA by the RNAi machinery or process (RNAi interference) or complementarity sufficient to trigger translational repression of the desired target mRNA. The term "sense strand" or "second strand" of an siRNA or RNAi agent refers to a strand that is complementary to the antisense strand or first strand. Antisense and sense strands can also be referred to as first or second strands, the first or second strand having complementarity to the target sequence and the respective second or first strand having complementarity to said first or second strand. miRNA duplex intermediates or siRNA-like duplexes include a miRNA strand having sufficient complementarity to a section of about 10-50 nucleotides of the mRNA of the gene targeted for silencing and a miRNA* strand having sufficient complementarity to form a duplex with the miRNA strand.

As used herein, the term "guide strand" refers to a strand of an RNAi agent, e.g., an antisense strand of an siRNA duplex, that enters into the RISC complex and directs cleavage of the target mRNA.

A "target gene" is a gene whose expression is to be selectively inhibited or "silenced." This silencing can be achieved by cleaving the mRNA of the target gene or via translational repression of the target gene.

The term "engineered," as in an engineered RNA precursor, or an engineered nucleic acid molecule, indicates that the precursor or molecule is not found in nature, in that all or a portion of the nucleic acid sequence of the precursor or molecule is created or selected by man. Once created or selected, the sequence can be replicated, translated, transcribed, or otherwise processed by mechanisms within a cell. Thus, an RNA precursor produced within a cell from a transgene that includes an engineered nucleic acid molecule is an engineered RNA precursor.

As used herein, the term "asymmetry", as in the asymmetry of a RNA duplex (e.g. a siRNA duplex or siRNA-like or miRNA duplex), refers to an inequality of bond strength or base pairing strength between the duplex termini (e.g., between terminal nucleotides on a first strand and terminal nucleotides on an opposing second strand), such that the 5' end of one strand of the duplex is more frequently in a transient unpaired, e.g, single-stranded, state than the 5' end of the complementary strand. This structural difference determines that one strand of the duplex is preferentially incorporated into a RISC complex. The strand whose 5' end is less tightly paired to the complementary strand will preferentially be incorporated into RISC and mediate gene silencing (e.g. RNAi or translational repression).

As used herein, the term "bond strength" or "base pair strength" refers to the strength of the interaction between pairs of nucleotides (or nucleotide analogs) on opposing strands of an oligonucleotide duplex (e.g., an siRNA duplex), due primarily to H-bonding, Van der Waals interactions, and the like between said nucleotides (or nucleotide analogs).

As used herein, the "5' end", as in the 5' end of an antisense strand, refers to the 5' terminal nucleotides, e.g., between one and about 5 nucleotides at the 5' terminus of the antisense strand. As used herein, the "3' end", as in the 3' end of a sense strand, refers to the region, e.g., a region of between one and about 5 nucleotides, that is complementary to the nucleotides of the 5' end of the complementary antisense strand.

As used herein, the term "isolated RNA" (e.g., "isolated shRNA", "isolated siRNA", "isolated siRNA-like duplex", "isolated miRNA", "isolated gene silencing agent", or "isolated RNAi agent") refers to RNA molecules which are substantially free of other cellular material, or culture medium when produced by recombinant techniques, or substantially free of chemical precursors or other chemicals when chemically synthesized.

As used herein, the term "transgene" refers to any nucleic acid molecule, which is inserted by artifice into a cell, and becomes part of the genome of the organism that develops from the cell. Such a transgene may include a gene that is partly or entirely heterologous (i.e., foreign) to the transgenic organism, or may represent a gene homologous to an endogenous gene of the organism. The term "transgene" also means a nucleic acid molecule that includes one or more selected nucleic acid sequences, e.g., DNAs, that encode one or more engineered RNA precursors, to be expressed in a transgenic organism, e.g., animal, which is partly or entirely heterologous, i.e., foreign, to the transgenic animal, or homologous to an endogenous gene of the transgenic animal, but which is designed to be inserted into the animal's genome at a location which differs from that of the natural gene. A transgene includes one or more promoters and any other DNA, such as introns, necessary for expression of the selected micleic acid sequence, all operably linked to the selected sequence, and may include an enhancer sequence.

The term "in vitro" has its art recognized meaning, e.g., involving purified reagents or extracts, e.g., cell extracts. The term "in vivo" also has its art recognized A gene "involved" in a disorder includes a gene, the normal or aberrant expression or function of which effects or causes a disease or disorder or at least one symptom of said disease or disorder.

Various methodologies of the instant invention include step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an RNAi agent of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Various aspects of the invention are described in further detail in the following subsections.

I. RNA Silencing Agents

The present invention features RNA silencing agents (e.g. siRNAs or siRNA-like duplexes), in particular, RNA silencing agents having enhanced efficacy for gene silencing based on an asymmetry which promotes entry of a preferred strand into RISC.

1. Enhancement of RNA Silencing Agents

In certain aspects, the present invention features "small interfering RNA molecules" ("siRNA molecules" or "siRNA"), "miRNA" molecules, methods of making said siRNA and miRNA molecules, and methods (e.g., research and/or therapeutic methods) for using said siRNA and miRNA molecules. An RNA silencing agent (e.g. siRNA or miRNA molecule) of the invention is a duplex consisting of a sense strand and complementary antisense strand, the antisense strand having sufficient complementarity to a target mRNA to mediate RNAi or translational repression. Preferably, the strands are aligned such that there are at least 1, 2, or 3 bases at the end of the strands which do not align (i.e., for which no complementary bases occur in the opposing strand) such that an overhang of 1, 2 or 3 residues occurs at one or both ends of the duplex when strands are annealed. Preferably, the siRNA or miRNA molecule has a length from about 10-50 or more nucleotides, i.e., each strand comprises 10-50 nucleotides (or nucleotide analogs). More preferably, the siRNA or miRNA molecule has a length from about 15-45 or 15-30 nucleotides. Even more preferably, the siRNA or miRNA molecule has a length from about 16-25 or 18-23 nucleotides.

In other aspects, the invention features siRNA-like duplex molecules, as well as methods, for making and using such molecules in RNA silencing. siRNA-like duplexes (like siRNA duplexes) include a first or miRNA strand and a second or miRNA* strand and are structurally similar to siRNA duplexes. Modifications within the duplex are permitted. Modifications that do not significantly affect RNA-silencing activity are particularly tolerated. siRNA-like duplexes mediate translational repression or RNAi depending on the degree of complementarity with target mRNA, as described supra.

RNA silencing agents (e.g. siRNAs or miRNAs) featured in the invention provide enhanced specificity and efficacy for mediating RISC-mediated cleavage or translational repression of a desired target gene. In preferred aspect, the base pair strength between the antisense strand 5' end (AS 5') and the sense strand 3' end (S 3') of the siRNA, or miRNAs molecule is less than the bond strength or base pair strength between the antisense strand 3' end (AS 3') and the sense strand 5' end (S '5), such that the antisense strand preferentially guides cleavage or translational repression of a target mRNA.

In one embodiment, the bond strength or base-pair strength is less due to fewer G:C base pairs between the 5' end of the first or antisense strand and the 3' end of the second or sense strand than between the 3' end of the first or antisense strand and the 5' end of the second or sense strand.

In another embodiment, the bond strength or base pair strength is less due to at least one mismatched base pair between the 5' end of the first or antisense strand and the 3' end of the second or sense strand. Preferably, the mismatched base pair is selected from the group consisting of G:A, C:A, C:U, G:G, A:A, C:C and U:U. In a related embodiment, the bond strength or base pair strength is less due to at least one wobble base pair, e.g., G:U, between the 5' end of the first or antisense strand and the 3' end of the second or sense strand.

In yet another embodiment, the bond strength or base pair strength is less due to at least one base pair comprising a rare nucleotide, e.g, inosine (I). Preferably, the base pair is selected from the group consisting of an I:A, I:U and I:C.

In yet another embodiment, the bond strength or base pair strength is less due to at least one base pair comprising a modified nucleotide. In preferred embodiments, the modified nucleotide is selected from the group consisting of 2-amino-G, 2-amino-A, 2,6-diamino-G, and 2,6-diamino-A.

2. Complementarity of RNA Silencing Agents with Target mRNA

The siRNA molecules of the invention further have a sequence that is "sufficiently complementary" to a target mRNA sequence to direct target-specific RNA interference (RNAi), as defined herein, i.e., the siRNA has a sequence sufficient to trigger the destruction of the target mRNA by the RNAi machinery or process.

In general, siRNA containing nucleotide sequences sufficiently identical to a portion of the target gene to effect RISC-mediated cleavage of the target gene are preferred. 100% sequence identity between the siRNA and the target gene is not required to practice the present invention. The invention has the advantage of being able to tolerate certain sequence variations to enhance efficiency and specificity of RNAi. Moreover, siRNA sequences with insertions, deletions, and single point mutations relative to the target sequence can also be effective for inhibition. Alternatively, siRNA sequences with nucleotide analog substitutions or insertions can be effective for inhibition.

siRNA-like molecules of the invention have a sequence (i.e., have a strand having a sequence) that is "sufficiently complementary" to a target mRNA sequence to direct gene silencing either by RNAi or translational repression. As the degree of sequence identity between a miRNA sequence and the corresponding target gene sequence is decreased, the tendency to mediate post-transcriptional gene silencing by translational repression rather than RNAi is increased. Therefore, in an alternative embodiment, where post-transcriptional gene silencing by translational repression of the target gene is desired, the miRNA sequence has partial complementarity with the target gene sequence. In certain embodiments, the miRNA sequence has partial complementarity with one or more short sequences (complementarity sites) dispersed within the target mRNA (e.g. within the 3'-UTR of the target mRNA) (Hutvagner and Zamore, Science, 2002; Zeng et al., Mol. Cell, 2002; Zeng et al., RNA, 2003; Doench et al., Genes & Dev., 2003). Since the mechanism of translational repression is cooperative, multiple complementarity sites (e.g., 2, 3, 4, 5, or 6) may be targeted in certain embodiments.

Sequence identity may determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the BLAST programs (version 2.0) of Altschul, et al. (1990) *J. Mol. Biol.* 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) *Nucleic Acids Res.* 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, *CABIOS* (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Greater than 80% sequence identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% sequence identity, between the siRNA antisense strand and the portion of the target gene is preferred. Conversely, miRNA sequences with less than 80% identity and the portion of the target gene (i.e. the site of complementarity) are preferred in order to mediate silencing by translational repression. Alternatively, the siRNA may be defined functionally as a nucleotide sequence (or oligonucleotide sequence) that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6(log10[Na+])+0.41(% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, *Molecular Cloning: A Laboratory Manual*, Cold Spring Harbor Laboratory Press, Cold Spring Harbor, N.Y., chapters 9 and 11, and *Current Protocols in Molecular Biology*, 1995, F. M. Ausubel et al., eds., John Wiley & Sons, Inc., sections 2.10 and 6.3-6.4, incorporated herein by reference. The length of the identical nucleotide sequences may be at least about 10, 12, 15, 17, 20, 22, 25, 27, 30, 32, 35, 37, 40, 42, 45, 47 or 50 bases.

The capacity of a siRNA-like duplex to mediate RNAi or translational repression may be predicted by the distribution of non-identical nucleotides between the target gene sequence and the nucleotide sequence of the silencing agent at the site of complementarity. In one embodiment, where gene silencing by translational repression is desired, at least one non-identical nucleotide is present in the central portion of the complementarity site so that duplex formed by the miRNA guide strand and the target mRNA contains a central "bulge" (Doench J G et al., Genes & Dev., 2003). In another embodiment 2, 3, 4, 5, or 6 contiguous or non-contiguous non-identical nucleotides are introduced. The non-identical nucleotide may be selected such that it forms a wobble base pair (e.g., G:U) or a mismatched base pair (G:A, C:A, C:U, G:G, A:A, C:C, U:U). In a further preferred embodiment, the "bulge" is centered at nucleotide positions 12 and 13 from the 5'end of the miRNA molecule.

3. Modification of RNA Silencing Agents

The RNA silencing molecules of the present invention can be modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference.

In a preferred aspect, the invention features RNA silencing agents (e.g. small interfering RNAs (siRNAs) or siRNA-like molecules) that include first and second strands wherein the second strand and/or first strand is modified by the substitution of internal nucleotides with modified nucleotides, such that in vivo stability is enhanced as compared to a corresponding unmodified agent (e.g. siRNA or siRNA-like duplex). As defined herein, an "internal" nucleotide is one occurring at any position other than the 5' end or 3' end of nucleic acid molecule, polynucleotide or oligonucleotide. An internal nucleotide can be within a single-stranded molecule or within a strand of a duplex or double-stranded molecule. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more internal nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the internal nucleotides. In yet another embodiment, the sense strand and/or antisense strand is modified by the substitution of all of the internal nucleotides.

In a preferred embodiment of the present invention the RNA molecule may contain at least one modified nucleotide analogue. The nucleotide analogues may be located at positions where the target-specific silencing activity, e.g., the RNAi mediating activity or translational repression activity is not substantially effected, e.g., in a region at the 5'-end and/or the 3'-end of the RNA molecule. Particularly, the ends may be stabilized by incorporating modified nucleotide analogues.

Preferred nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

Also preferred are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

4. Production of RNA Silencing Agents

RNA may be produced enzymatically or by partial/total organic synthesis, any modified nibonucleotide can be introduced by in vitro enzymatic or organic synthesis. In one embodiment, a silencing agent (e.g. a RNAi agent or translational repression agent) is prepared chemically. Methods of synthesizing RNA molecules are known in the art, in particular, the chemical synthesis methods as described in Verma and Eckstein (1998) *Annul Rev. Biochem.* 67:99-134.

In one embodiment, a RNA silencing agent (e.g. siRNA or siRNA-like duplex) is prepared enzymatically. For example, a short duplex RNA (e.g. siRNA or siRNA-like duplex) can be prepared by enzymatic processing of a long ds RNA having sufficient complementarity to the desired target mRNA. Processing of long ds RNA can be accomplished in vitro, for example, using appropriate cellular lysates and duplex RNA (e.g. siRNA or siRNA-like duplex) can be subsequently purified by gel electrophoresis or gel filtration. Duplex RNA (e.g. siRNA or siRNA-like duplex) can then be denatured according to art-recognized methodologies. In an exemplary embodiment, RNA can be purified from a mixture by extraction with a solvent or resin, precipitation, electrophoresis, chromatography, or a combination thereof. Alternatively, the RNA may be used with no or a minimum of purification to avoid losses due to sample processing. Alternatively, the RNA can also be prepared by enzymatic transcription from synthetic DNA templates or from DNA plasmids isolated from recombinant bacteria. Typically, phage RNA polymerases are used such as T7, T3 or SP6 RNA polymerase (Milligan and Uhlenbeck (1989) *Methods Enzymol.* 180:51-62). The RNA may be dried for storage or dissolved in an aqueous solution. The solution may contain buffers or salts to inhibit annealing, and/or promote stabilization of the single strands.

RNA silencing agents of the invention can also be prepared in vivo by enzymatic processing of a long dsRNA molecule (>30 b.p.) which has sufficient complementarity to the desired target mRNA. Preferably, in vivo processing of the long dsRNA molecule occurs in a non-mammalian cell or a mammalian cell which is deficient in the interferon-mediated inflammatory response to dsRNA. In one embodiment, the cell capable of dsRNA enzymatic processing may be present within an organism such that dsRNA processing can be induced in vivo to trigger gene silencing of a target gene within the organism. Alternatively, the cell (i.e. a host cell) containing endogenous machinery for dsRNA processing (e.g. DICER) or transformed with heterologous genes to enable dsRNA processing) be cultured and induced to process dsRNA in vitro. RNA silencing agents may then be purified from the host cell following dsRNA processing for administration to an organism containing the target gene to be silenced.

In another embodiment, RNA silencing agents (e.g. siRNAs or siRNA-like duplexes) are synthesized directly either in vivo, in situ, or in vitro. An endogenous RNA polymerase in the cell may mediate transcription of the RNA silencing agent in vivo or in situ, or a cloned RNA polymerase can be used for transcription of the RNA silencing agent in vivo or in vitro. For transcription from a transgene in vivo or an expression construct, a regulatory region (e.g., promoter, enhancer, silencer, splice donor and acceptor, polyadenylation) may be used to transcribe the RNA silencing agent (e.g. siRNA or or siRNA-like duplexes). Inhibition may be targeted by specific transcription in an organ, tissue, or cell type; stimulation of an environmental condition (e.g., infection, stress, temperature, chemical inducers); and/or engineering transcription at a developmental stage or age. A transgenic organism that expresses a RNA silencing agent (e.g. siRNA or siRNA-like duplexes) from a recombinant construct may be produced by introducing the construct into a zygote, an embryonic stem cell, or another multipotent cell derived from the appropriate organism.

5. Targeted mRNAs of RNA Silencing Agents

In one embodiment, the target mRNA of the invention specifies the amino acid sequence of a cellular protein (e.g., a nuclear, cytoplasmic, transmembrane, or membrane-associated protein). In another embodiment, the target mRNA of the invention specifies the amino acid sequence of an extracellular protein (e.g., an extracellular matrix protein or secreted protein). As used herein, the phrase "specifies the amino acid sequence" of a protein means that the mRNA sequence is translated into the amino acid sequence according to the rules of the genetic code. The following classes of proteins are listed for illustrative purposes: developmental proteins (e.g., adhesion molecules, cyclin kinase inhibitors, Wnt family members, Pax family members, Winged helix family members, Hox family members, cytokines/lymphokines and their receptors, growth/differentiation factors and their receptors, neurotransmitters and their receptors); oncogene-encoded proteins (e.g., ABLI, BCLI, BCL2, BCL6, CBFA2, CBL, CSFIR, ERBA, ERBB, EBRB2, ETSI, ETSI, ETV6, FGR, FOS, FYN, HCR, HRAS, JUN, KRAS, LCK, LYN, MDM2, MLL, MYB, MYC, MYCLI, MYCN, NRAS, PIM I, PML, RET, SRC, TALI, TCL3, and YES); tumor suppressor proteins (e.g., APC, BRCA1, BRCA2, MADH4, MCC, NF I, NF2, RB I, TP53, and WTI); and enzymes (e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextriinases, DNA and RNA polymerases, galactosidases, glucanases, glucose oxidases, granule-bound starch synthases, GTPases, helicases, hernicellulases, integrases, inulinases, invertases, isomerases, kinases, lactases, lipases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases).

In a preferred aspect of the invention, the target mRNA molecule of the invention specifies the amino acid sequence of a protein associated with a pathological condition. For example, the protein may be a pathogen-associated protein (e.g., a viral protein involved in immunosuppression of the host, replication of the pathogen, transmission of the pathogen, or maintenance of the infection), or a host protein which facilitates entry of the pathogen into the host, drug metabolism by the pathogen or host, replication or integration of the pathogen's genome, establishment or spread of infection in the host, or assembly of the next generation of pathogen.

Alternatively, the protein may be a tumor-associated protein or an autoimmune disease-associated protein.

In one embodiment, the target mRNA molecule of the invention specifies the amino acid sequence of an endogenous protein (i.e., a protein present in the genome of a cell or organism). In another embodiment, the target mRNA molecule of the invention specified the amino acid sequence of a heterologous protein expressed in a recombinant cell or a genetically altered organism. In another embodiment, the target mRNA molecule of the invention specified the amino acid sequence of a protein encoded by a transgene (i.e., a gene construct inserted at an ectopic site in the genome of the cell). In yet another embodiment, the target mRNA molecule of the invention specifies the amino acid sequence of a protein encoded by a pathogen genome which is capable of infecting a cell or an organism from which the cell is derived.

By inhibiting the expression of such proteins, valuable information regarding the function of said proteins and therapeutic benefits which may be obtained from said inhibition may be obtained.

II. Short Hairpin RNAs (shRNAs)

In certain featured embodiments, the instant invention provides shRNAs having enhanced specificity or efficacy in mediating gene silencing (e.g. RNAi or translational repression). In contrast to short RNA silencing duplexes (e.g. siRNA or siRNA-like duplexes), short hairpin RNAs (shRNAs) mimic the natural precursors of miRNAs and enter at the top of the gene silencing pathway. For this reason, shRNAs are believed to mediate gene silencing more efficiently by being fed through the entire natural gene silencing pathway.

A preferred shRNA of the invention is one that has been redesigned for increased specificity or enhancement relative to a previous shRNA. The new shRNA differs from a previous shRNA in that a silencing duplex produced from the new shRNA has less base pair strength between the 5' end of the antisense strand or first strand and the 3' end of the sense strand or second strand than the base pair strength between the 3' end of the antisense strand or first strand and the 5' end of the sense strand or second strand.

1. Engineered RNA Precursors that Generate RNA Silencing Agents

Naturally-occurring miRNA precursors (pre-miRNA) have a single strand that forms a duplex stem including two portions that are generally complementary, and a loop, that connects the two portions of the stem. In typical pre-miRNAs, the stem includes one or more bulges, e.g., extra nucleotides that create a single nucleotide "loop" in one portion of the stem, and/or one or more unpaired nucleotides that create a gap in the hybridization of the two portions of the stem to each other. Short hairpin RNAs, or engineered RNA precursors, of the invention are artificial constructs based on these naturally occurring pre-miRNAs, but which are engineered to deliver desired RNA silencing agents (e.g., siRNAs or siRNA-like duplexes).

In shRNAs, or engineered precursor RNAs, of the instant invention, one portion of the duplex stem is a nucleic acid sequence that is complementary (or anti-sense) to the target mRNA. Thus, engineered RNA precursors include a duplex stem with two portions and a loop connecting the two stem portions. The two stem portions are about 18 or 19 to about 25, 30, 35, 37, 38, 39, or 40 or more nucleotides in length. When used in mammalian cells, the length of the stem portions should be less than about 30 nucleotides to avoid provoking non-specific responses like the interferon pathway. In non-mammalian cells, the stem can be longer than 30 nucleotides. In fact, the stem can include much larger sections complementary to the target mRNA (up to, and including the entire mRNA). The two portions of the duplex stem must be sufficiently complementary to hybridize to form the duplex stem. Thus, the two portions can be, but need not be, fully or perfectly complementary. In addition, the two stem portions can be the same length, or one portion can include an overhang of 1, 2, 3, or 4 micleotides. The overhanging nucleotides can include, for example, uracils (Us), e.g., all Us. The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop in the shRNAs or engineered RNA precursors can be 2, 3, 4, 5, 6, 7, 8, 9, or more, e.g., 15 or 20, or more nucleotides in length.

In certain embodiments, shRNAs of the invention include the sequences of a desired RNA silencing agent (e.g. siRNA or siRNA-like duplex). The desired RNA silencing duplex (e.g. siRNA or siRNA-like duplex), and thus both of the two stem portions in the engineered RNA precursor, are selected by methods known in the art. These include, but are not limited to, selecting an 18, 19, 20, 21 nucleotide, or longer, sequence from the target gene mRNA sequence from a region 100 to 200 or 300 nucleotides on the 3' side of the start of translation. In general, the sequence can be selected from any portion of the mRNA from the target gene, such as the 5' UTR (untranslated region), coding sequence, or 3' UTR. This sequence can optionally follow immediately after a region of the target gene containing two adjacent AA nucleotides. The last two nucleotides of the 21 or so nucleotide sequence can be selected to be UU (so that the anti-sense strand of the siRNA begins with UU). This 21 or so nucleotide sequence is used to create one portion of a duplex stem in the engineered RNA precursor. This sequence can replace a stem portion of a wild-type pre-stRNA sequence, e.g., enzymatically, or is included in a complete sequence that is synthesized. For example, one can synthesize DNA oligonucleotides that encode the entire stem-loop engineered RNA precursor, or that encode just the portion to be inserted into the duplex stem of the precursor, and using restriction enzymes to build the engineered RNA precursor construct, e.g., from a wild-type pre-stRNA.

Engineered RNA precursors include in the duplex stem the 21-22 or so nucleotide sequences of the siRNA or siRNA-like duplex desired to be produced in vivo. Thus, the stem portion of the engineered RNA precursor includes at least 18 or 19 nucleotide pairs corresponding to the sequence of an exonic portion of the gene whose expression is to be reduced or inhibited. The two 3' nucleotides flanking this region of the stem are chosen so as to maximize the production of the siRNA from the engineered RNA precursor, and to maximize the efficacy of the resulting siRNA in targeting the corresponding mRNA for translational repression or destruction by RNAi in vivo and in vitro.

In certain embodiments, shRNAs of the invention include miRNA sequences, optionally end-modified miRNA sequences, to enhance entry into RISC. The miRNA sequence can be similar or identical to that of any naturally occurring miRNA (see e.g. The miRNA Registry; Griffiths-Jones S, *Nuc. Acids Res.*, 2004). Over one thousand natural miRNAs have been identified to date and together they are thought to comprise ~1% of all predicted genes in the genome. Many natural miRNAs are clustered together in the introns of pre-mRNAs and can be identified in silico using homology-based searches (Pasquinelli et al., 2000; Lagos-Quintana et al., 2001; Lau et al., 2001; Lee and Ambros, 2001) or computer algorithms (e.g MiRScan, MiRSeeker) that predict the capability of a candidate miRNA gene to form the stem loop structure of a pri-mRNA (Grad et al., Mol. Cell., 2003; Lim et al., Genes Dev., 2003; Lim et al., Science, 2003; Lai E C et al., Genome Bio., 2003). An online registry provides a searchable database of all published miRNA sequences (The miRNA Registry at the Sanger Institute website; Griffiths-Jones S, *Nuc. Acids Res.*, 2004). Exemplary, natural miRNAs include lin-4, let-7, miR-10, mirR-15, miR-16, miR-168, miR-175, miR-196 and their homologs, as well as other natural miRNAs from humans and certain model organisms including *Drosophila melanogaster, Caenorhabditis elegans,* zebrafish, *Arabidopsis thalania*, mouse, and rat as described in International PCT Publication No. WO 03/029459.

Naturally-occurring miRNAs are expressed by endogenous genes in vivo and are processed from a hairpin or stem-loop precursor (pre-miRNA or pri-miRNAs) by Dicer or other RNAses (Lagos-Quintana et al., Science, 2001; Lau et al., Science, 2001; Lee and Ambros, Science, 2001; Lagos-Quintana et al., Curr. Biol., 2002; Mourelatos et al., Genes Dev., 2002; Reinhart et al., Science, 2002; Ambros et al., Curr. Biol., 2003; Brennecke et al., 2003; Lagos-Quintana et al., RNA, 2003; Lim et al., Genes Dev., 2003; Lim et al., Science, 2003). miRNAs can exist transiently in vivo as a double-stranded duplex but only one strand is taken up by the RISC complex to direct gene silencing. Certain miRNAs, e.g. plant miRNAs, have perfect or near-perfect complementarity to their target mRNAs and, hence, direct cleavage of the target mRNAs. Other miRNAs have less than perfect complementarity to their target mRNAs and, hence, direct translational repression of the target mRNAs. The degree of complementarity between an miRNA and its target mRNA is believed to determine its mechanism of action. For example, perfect or near-perfect complementarity between a miRNA and its target mRNA is predictive of a cleavage mechanism (Yekta et al., *Science,* 2004), whereas less than perfect complementarity is predictive of a translational repression mechanism.

In particular embodiments, the miRNA sequence is that of a naturally-occurring miRNA sequence, the aberrant expression or activity of which is correlated with a miRNA disorder.

Another defining feature of these engineered RNA precursors is that as a consequence of their length, sequence, and/or structure, they do not induce sequence non-specific responses, such as induction of the interferon response or apoptosis, or that they induce a lower level of such sequence non-specific responses than long, double-stranded RNA (>150 bp) that has been used to induce post-transcriptional gene silencing (e.g. RNAi). For example, the interferon response is triggered by dsRNA longer than 30 base pairs.

2. Transgenes Encoding Engineered RNA Precursors

The new engineered RNA precursors can be synthesized by standard methods known in the art, e.g., by use of an automated DNA synthesizer (such as are commercially available from Biosearch, Applied Biosystems, etc.). These synthetic, engineered RNA precursors can be used directly as described below or cloned into expression vectors by methods known in the field. The engineered RNA precursors should be delivered to cells in vitro or in vivo in which it is desired to target a specific mRNA for silencing (e.g. destruction or repression). A number of methods have been developed for delivering DNA or RNA to cells. For example, for in vivo delivery, molecules can be injected directly into a tissue site or administered systemically. In vitro delivery includes methods known in the art such as electroporation and lipofection.

To achieve intracellular concentrations of the nucleic acid molecule sufficient to suppress expression of endogenous mRNAs, one can use, for example, a recombinant DNA construct in which the oligonucleotide is placed under the control of a strong Pol III (e.g., U6 or Pol III H1-RNA promoter) or Pol II promoter. The use of such a construct to transfect target cells in vitro or in vivo will result in the transcription of sufficient amounts of the engineered RNA precursor to lead to the production of a RNA duplex (e.g. siRNA or siRNA-like duplex) that can target a corresponding mRNA sequence for cleavage (i.e. RNAi) or translational repression to decrease the expression of the gene encoding that mRNA. For example, a vector can be introduced in vivo such that it is taken up by a cell and directs the transcription of an engineered RNA precursor. Such a vector can remain episomal or become chromosomally integrated, as long as it can be transcribed to produce the desired stRNA precursor.

Such vectors can be constructed by recombinant DNA technology methods known in the art. Vectors can be plasmid, viral, or other vectors known in the art such as those described herein, used for replication and expression in mammalian cells or other targeted cell types. The nucleic acid sequences encoding the engineered RNA precursors can be prepared using known techniques. For example, two synthetic DNA oligonucleotides can be synthesized to create a novel gene encoding the entire engineered RNA precursor. The DNA oligonucleotides, which will pair, leaving appropriate 'sticky ends' for cloning, can be inserted into a restriction site in a plasmid that contains a promoter sequence (e.g., a Pol II or a Pol III promoter) and appropriate terminator sequences 3' to the engineered RNA precursor sequences (e.g., a cleavage and polyadenylation signal sequence from SV40 or a Pol III terminator sequence).

The invention also encompasses genetically engineered host cells that contain any of the foregoing expression vectors and thereby express the nucleic acid molecules of the invention in the host cell. The host cells can be cultured using known techniques and methods (see, e.g., Culture of Animal Cells (R. I. Freshney, Alan R. Liss, Inc. 1987); Molecular Cloning, Sambrook et al. (Cold Spring Harbor Laboratory Press, 1989)).

Successful introduction of the vectors of the invention into host cells can be monitored using various known methods. For example, transient transfection can be signaled with a reporter, such as a fluorescent marker, such as Green Fluorescent Protein (GFP). Stable transfection can be indicated using markers that provide the transfected cell with resistance to specific environmental factors (e.g., antibiotics and drugs), such as hygromycin B resistance, e.g., in insect cells and in mammalian cells.

3. Regulatory Sequences

The expression of the engineered RNA precursors is driven by regulatory sequences, and the vectors of the invention can include any regulatory sequences known in the art to act in mammalian cells, e.g., human or murine cells; in insect cells; in plant cells; or other cells. The term regulatory sequence includes promoters, enhancers, and other expression control elements. It will be appreciated that the appropriate regulatory sequence depends on such factors as the future use of the cell or transgenic animal into which a sequence encoding an engineered RNA precursor is being introduced, and the level of expression of the desired RNA precursor. A person skilled in the art would be able to choose the appropriate regulatory sequence. For example, the transgenic animals described herein can be used to determine the role of a test polypeptide or the engineered RNA precursors in a particular cell type, e.g., a hematopoietic cell. In this case, a regulatory sequence that drives expression of the transgene ubiquitously, or a hematopoietic-specific regulatory sequence that expresses the transgene only in hematopoietic cells, can be used. Expression of the engineered RNA precursors in a hematopoietic cell means that the cell is now susceptible to specific, targeted silencing (e.g. RNAi) of a particular gene. Examples of various regulatory sequences are described below.

The regulatory sequences can be inducible or constitutive. Suitable constitutive regulatory sequences include the regulatory sequence of a housekeeping gene such as the α-actin regulatory sequence, or may be of viral origin such as regulatory sequences derived from mouse mammary tumor virus (MMTV) or cytomegalovirus (CMV).

Alternatively, the regulatory sequence can direct transgene expression in specific organs or cell types (see, e.g., Lasko et al., 1992, Proc. Natl. Acad. Sci. USA 89:6232). Several tissue-specific regulatory sequences are known in the art including the albumin regulatory sequence for liver (Pinkert et al., 1987, Genes Dev. 1:268276); the endothelin regulatory sequence for endothelial cells (Lee, 1990, J. Biol. Chem. 265:10446-50); the keratin regulatory sequence for epidermis; the myosin light chain-2 regulatory sequence for heart (Lee et al., 1992, J. Biol. Chem. 267:15875-85), and the insulin regulatory sequence for pancreas (Bucchini et al., 1986, Proc. Natl. Acad. Sci. USA 83:2511-2515), or the vav regulatory sequence for hematopoietic cells (Oligvy et al., 1999, Proc. Natl. Acad. Sci. USA 96:14943-14948). Another suitable regulatory sequence, which directs constitutive expression of transgenes in cells of hematopoietic origin, is the murine MHC class I regulatory sequence (Morello et al., 1986, EMBO J. 5:1877-1882). Since NMC expression is induced by cytokines, expression of a test gene operably linked to this regulatory sequence can be upregulated in the presence of cytokines.

In addition, expression of the transgene can be precisely regulated, for example, by using an inducible regulatory sequence and expression systems such as a regulatory sequence that is sensitive to certain physiological regulators, e.g., circulating glucose levels, or hormones (Docherty et al., 1994, FASEB J. 8:20-24). Such inducible expression systems, suitable for the control of transgene expression in cells or in mammals such as mice, include regulation by ecdysone, by estrogen, progesterone, tetracycline, chemical inducers of dimerization, and isopropyl-beta-D1-thiogalactopyranoside (IPTG) (collectively referred to as "the regulatory molecule"). Each of these expression systems is well described in the literature and permits expression of the transgene throughout the animal in a manner controlled by the presence or absence of the regulatory molecule. For a review of inducible expression systems, see, e.g., Mills, 2001, Genes Devel. 15:1461-1467, and references cited therein.

The regulatory elements referred to above include, but are not limited to, the cytomegalovirus hCMV immediate early gene, the early or late promoters of SV40 adenovirus (Bernoist et al., Nature, 290:304, 1981), the tet system, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors. Additional promoters include the promoter contained in the 3' long terminal repeat of Rous sarcoma virus (Yamamoto et al., Cell 22:787-797, 1988); the herpes thymidine kinase promoter (Wagner et al., Proc. Natl. Acad. Sci. USA 78:1441, 1981); or the regulatory sequences of the metallothionein gene (Brinster et al., Nature 296:39, 1988).

4. Assay for Testing Engineered RNA Precursors

Drosophila embryo lysates can be used to determine if an engineered RNA precursor was, in fact, the direct precursor of a mature stRNA or siRNA. This lysate assay is described in Tuschl et al., 1999, supra, Zamore et al., 2000, supra, and Hutvdgner et al. 2001, supra. These lysates recapitulate RNAi in vitro, thus permitting investigation into whether the proposed precursor RNA was cleaved into a mature stRNA or siRNA by an RNAi-like mechanism. Briefly, the precursor RNA is incubated with Drosophila embryo lysate for various times, then assayed for the production of the mature siRNA or stRNA by primer extension or Northern hybridization. As in the in vivo setting, mature RNA accumulates in the cell-free reaction. Thus, an RNA corresponding to the proposed precursor can be shown to be converted into a mature stRNA or siRNA duplex in the Drosophila embryo lysate.

Furthermore, an engineered RNA precursor can be functionally tested in the Drosophila embryo lysates. In this case, the engineered RNA precursor is incubated in the lysate in the presence of a 5' radiolabeled target mRNA in a standard in vitro RNAi reaction for various lengths of time. The target mRNA can be 5' radiolabeled using guanylyl transferase (as described in Tuschl et al., 1999, supra and references therein) or other suitable methods. The products of the in vitro reaction are then isolated and analyzed on a denaturing acrylamide or agarose gel to determine if the target mRNA has been cleaved in response to the presence of the engineered RNA precursor in the reaction. The extent and position of such cleavage of the mRNA target will indicate if the engineering of the precursor created a pre-siRNA capable of mediating sequence-specific RNAi.

IV. Methods of Introducing RNAs, Vectors, and Host Cells

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus the RNA may be introduced along with components that perform one or more of the following activities: enhance RNA uptake by the cell, inhibit annealing of single strands, stabilize the single strands, or other-wise increase inhibition of the target gene.

RNA may be directly introduced into the cell (i.e., intracellularly); or introduced extracellularly into a cavity, interstitial space, into the circulation of an organism, introduced orally, or may be introduced by bathing a cell or organism in a solution containing the RNA. Vascular or extravascular circulation, the blood or lymph system, and the cerebrospinal fluid are sites where the RNA may be introduced.

The cell with the target gene may be derived from or contained in any organism. The organism may a plant, animal, protozoan, bacterium, virus, or fungus. The plant may be a monocot, dicot or gymnosperm; the animal may be a vertebrate or invertebrate. Preferred microbes are those used in agriculture or by industry, and those that are pathogenic for plants or animals. Fungi include organisms in both the mold and yeast morphologies. Plants include arabidopsis; field crops (e.g., alfalfa, barley, bean, corn, cotton, flax, pea, rape, nice, rye, safflower, sorghum, soybean, sunflower, tobacco, and wheat); vegetable crops (e.g., asparagus, beet, broccoli, cabbage, carrot, cauliflower, celery, cucumber, eggplant, lettuce, onion, pepper, potato, pumpkin, radish, spinach, squash, taro, tomato, and zucchini); fruit and nut crops (e.g., almond, apple, apricot, banana, black-berry, blueberry, cacao, cherry, coconut, cranberry, date, faJoa, filbert, grape, grapefruit, guava, kiwi, lemon, lime, mango, melon, nectarine, orange, papaya, passion fruit, peach, peanut, pear, pineapple, pistachio, plum, raspberry, strawberry, tangerine, walnut, and watermelon); and ornamentals (e.g., alder, ash, aspen, azalea, birch, boxwood, camellia, carnation, chrysanthemum, elm, fir, ivy, jasmine, juniper, oak, palm, poplar, pine, redwood, rhododendron, rose, and rubber). Examples of vertebrate animals include fish, mammal, cattle, goat, pig, sheep, rodent, hamster, mouse, rat, primate, and human; invertebrate animals include nematodes, other worms, *drosophila*, and other insects.

The skilled artisan will appreciate that the enumerated organisms are also useful for practicing other aspects of the invention, e.g., making transgenic organisms as described infra.

The cell having the target gene may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Depending on the particular target gene and the dose of double stranded RNA material delivered, this process may provide partial or complete loss of function for the target gene. A reduction or loss of gene expression in at least 50%, 60%, 70%, 80%, 90%, 95% or 99% or more of targeted cells is exemplary. Inhibition of gene expression refers to the absence (or observable decrease) in the level of protein and/or mRNA product from a target gene. Specificity refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS).

For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentarnycin, hygromycin, kanamycin, lincomycin, methotrexate, phosphinothricin, puromycin, and tetracyclin. Depending on the assay, quantitation of the amount of gene expression allows one to determine a degree of inhibition which is greater than 10%, 33%, 50%, 90%, 95% or 99% as compared to a cell not treated according to the present invention. Lower doses of injected material and longer times after administration of a RNA silencing agent (e.g., an RNAi agent) may result in inhibition in a smaller fraction of cells (e.g., at least 10%, 20%, 50%, 75%, 90%, or 95% of targeted cells). Quantitation of gene expression in a cell may show similar amounts of inhibition at the level of accumulation of target mRNA or translation of target protein. As an example, the efficiency of inhibition may be determined by assessing the amount of gene product in the cell; mRNA may be detected with a hybridization probe having a nucleotide sequence outside the region used for the inhibitory double-stranded RNA, or translated polypeptide may be detected with an antibody raised against the polypeptide sequence of that region.

The RNA may be introduced in an amount which allows delivery of at least one copy per cell. Higher doses (e.g., at least 5, 10, 100, 500 or 1000 copies per cell) of material may yield more effective inhibition; lower doses may also be useful for specific applications.

V. Methods of Treatment:

The present invention provides for both prophylactic and therapeutic methods of treating a subject at risk of (or susceptible to) a disease or disorder or having a disease or disorder associated with aberrant or unwanted target gene expression or activity. The invention further provides methods of treating cell or subject having (or susceptible to) an miRNA disorder.

"Treatment", or "treating" as used herein, is defined as the application or administration of a therapeutic agent (e.g., a RNAi agent or agent mediating translational control, or vector or transgene encoding same) to a patient, or application or administration of a therapeutic agent to an isolated tissue or cell line from a patient, who has a disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the target gene molecules of the present invention or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant or unwanted target gene expression or activity, by administering to the subject a therapeutic agent (e.g., a RNAi agent or agent mediating translational control, or vector or transgene encoding same). Subjects at risk for a disease which is caused or contributed to by aberrant or unwanted target gene expression or activity can be identified by, for example, any or a combination of diagnostic or prognostic assays as described herein. Administration of a prophylactic agent can occur prior to the manifestation of symptoms characteristic of the target gene aberrancy, such that a disease or disorder is prevented or, alternatively, delayed in its progression. Depending on the type of target gene aberrancy, for example, a target gene, target gene agonist or target gene antagonist agent can be used for treating the subject. The appropriate agent can be determined based on screening assays described herein.

2. Therapeutic Methods

Another aspect of the invention pertains to methods of modulating target gene expression, protein expression or activity for therapeutic purposes. Accordingly, in an exemplary embodiment, the modulatory method of the invention involves contacting a cell capable of expressing target gene with a therapeutic agent (e.g., a RNAi agent or agent mediating translational control, or vector or transgene encoding same) that is specific for the target gene or protein (e.g., is specific for the mRNA encoded by said gene or specifying the amino acid sequence of said protein) such that expression or one or more of the activities of target protein is modulated. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a target gene polypeptide or nucleic acid molecule. Inhibition of target gene activity is desirable in situations in which target gene is abnormally unregulated and/or in which decreased target gene activity is likely to have a beneficial effect.

3. miRNA Therapy

Another aspect of the invention pertains to methods of treating a cell or subject having or susceptible to an miRNA disorder. MiRNA disorders can result, for example, when a naturally occurring miRNA is not present in a cell or subject in an amount sufficient to regulate cellular processes controlled by the miRNA. In an exemplary embodiment, the method of the invention involves administering to a subject having or susceptible to an miRNA disorder an effective amount of a RNA silencing agent of the invention (e.g., a siRNA-like duplex) or vector or transgene encoding same, the silencing agent delivering at least one strand (e.g., a miRNA strand of the siRNA-like agent) to the subject (e.g., to the RISC complex of said subject). In another exemplary embodiment, the method of the invention involves contacting a cell from a subject having or susceptible to an miRNA disorder with an effective amount of a RNA silencing agent of the invention (e.g., a siRNA-like duplex) or vector or transgene encoding same, the silencing agent delivering at least one strand (e.g., a miRNA strand of the siRNA-like agent) to the cell (e.g., to the RISC complex of said cell). An effective amount of a siRNA-like agent is, for example, an amount suffficient to silence the natural target of the miRNA strand of the siRNA-like duplex.

miRNAs have been shown to regulate a diverse set of biological processes in metazoans (e.g. invertebrates, vertebrates, and plants) including cell proliferation and cell death (McManus M T et al., Semin. Cancer Biol., 2003; Brenneke et al., Cell, 2003; Baehrecke E H. Curr. Biol., 2003), developmental timing (Pasquinelli A E and Ruvkun G, Annu Rev. Cell. Dev., 2002), embryonic and post-embryonic development (Lee R C and Ambros V, Science, 2001; Boutla A et al., Nuc. Acids. Res., 2003; Carrington J C and Ambros V, Science, 2003; Houbaviy H B et al., Dev. Cell, 2003; Aravin A A et al., Dev. Cell, 2003; Yekta et al., Science, 2004; Vaucheret et al., Genes & Dev., 2004), neuronal development (Johnston R J and Hobert O, Nature, 2003; Kawasaki H and Taira K, Nature, 2003; Krichevsky A M et al., RNA, 2003; Kim J et al., PNAS, 2004; Sempere L F et al., Genome Biology, 2004), fat metabolism (Xu et al., Curr. Biol., 2003), haematopoietic cell differentiation (Chen C Z et al, Science, 2004) and flower and leaf development (Aukerman M J and Sakai H, Plant Cell, 2003; Bartel B and Bartel D P, Plant Physiol., 2003; Chen X, Science, 2003; Emery J F et al., Curr. Biol., 2003; Hake et al., Curr. Biol., 2003; Hunter C and Poethig R, Curr. Opin. Genet. Dev., 2003; Kidner C A and Martienssen R A, Trends Genet., 2003; Palatnik J F, Nature, 2003; Achard P et al., Development, 2004; Zhong R et al., Plant Cell Physiol., 2004; Kidner C A et al., Nature, 2004; Mallory A C et al., Curr. Biol., 2004). miRNA disorders can result in severe disruption of these processes. miRNA disorders have been implicated in a wide variety of plant and animal diseases including cancer, neurological disorders (e.g. neurodegeneration), and developmental defects. For example, miRNA disorders have been correlated with nonsmall cell lung cancer (Takamizawa et al., Cancer Research, 2004), colorectal cancer (Michael M Z et al., Mol. Cancer. Res., 2003), chronic lymphocytic leukemia (Calin G A et al., PNAS, 2002; Calin G A et al., PNAS, 2004), Fragile X Syndrome (Caudy A et al, Genes & Dev., 2002), spinal muscular atrophy and Waisman Syndrome (Dostie et al., RNA, 2003). Additional miRNA-silenced target gene linked with a particular miRNA disorder can be identified in silico using computational algorithms described in the art (Rhoades et al. Cell, 2002; Enright et al. Genome Biol., 2003; Lewis et al., Cell, 2003; Stark et al., PLOS Biol., 2003).

The choice of which strand of the siRNA-like duplex is preferentially loaded in the RISC complex may depend on the nature of the miRNA disorder. In one scenario, an miRNA disorders can result from a deficiency in the expression of a particular natural miRNA due to a mutation or chromosomal lesion (e.g. translocation, inversion, or deletion) in the miRNA gene or a regulatory sequence controlling its expression (e.g. an miRNA promoter). In another scenario, an miRNA disorders can result from an acquisition of a mutation in a target mRNA. For example, a mutation in a miRNA-silenced target gene can render the target mRNA resistant to silencing, leading to overexpression of a target mRNA that is normally silenced. Alternatively, a mutation in the miRNA-silenced target gene can render the target mRNA susceptible to miRNA-guided cleavage, leading to underexpression of a target mRNA that is normally constitutively expressed.

In another scenario, an miRNA disorder can result from the acquisition of a mutation in a natural miRNA. A mutation in the 5' end of an in individual strand of an miRNA duplex can result in the loading the wrong strand in RISC. For example, when the miRNA* strand is inappropriately loaded in RISC, the target mRNA may no longer be silenced, leading to overexpression of a target mRNA that is normally silenced and/or underexpression of a new, inappropriate target mRNA that is normally not silenced ("off-target silencing"). In yet another scenario, an miRNA disorder can result from a mutation in a gene encoding a component of the RISC complex such that miRNA-mediated gene silencing is abrogated.

Use of the design rules described supra can abe applied to the RNA silencing agents to correct for an miRNA disorder. In particular, miRNA duplex intermediates or siRNA-like duplexes that include a miRNA strand and/or a miRNA* strand can be altered with the design rules to promote entry of the desired strand of the duplex (e.g., the miRNA strand) into a RISC complex. In one aspect of the invention, entry of the miRNA strand into the RISC complex is desired in order to treat the disorder. In another embodiment of the invention, entry of the miRNA* strand is desired in order to treat the disorder. Entry of the miRNA strand may be promoted by either lessening the base pair strength between the 5' end of the miRNA strand and the 3' end of the miRNA* strand (miRNA* 3') as compared to the base pair strength between the 3' end of the miRNA strand and the 5' end of the miRNA* strand or enhancing the base pair strength between the 3' end of the miRNA strand and the 5' end of the miRNA* strand as compared to the base pair strength between the 5' end of miRNA strand and the 3' end of the miRNA* strand. Alternatively, entry of the sense strand may be promoted by lessening the base pair strength between the 5' end of the miRNA* strand (miRNA* 5') and the 3' end of the miRNA strand (miRNA 3') as compared to the base pair strength between the 3' end of the miRNA* strand (miRNA* 3') and the 5' end of the miRNA strand (miRNA '5) or enhancing the base pair strength between the 3' end of the miRNA* strand (miRNA 3') and the 5' end of the miRNA strand (miRNA '5) as compared to the base pair strength between the 5' end of miRNA* strand (miRNA* 5') and the 3' end of the miRNA strand (miRNA 3').

4. Pharmacogenomics

The therapeutic agents (e.g., a RNAi agent or vector or transgene encoding same) of the invention can be administered to individuals to treat (prophylactically or therapeutically) disorders associated with aberrant or unwanted target gene activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a therapeutic agent as well as tailoring the dosage and/or therapeutic regimen of treatment with a therapeutic agent.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10-11): 983-985 and Linder, M. W. et al. (1997) *Clin. Chem.* 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a target gene polypeptide of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a therapeutic agent of the present invention can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a therapeutic agent, as described herein.

Therapeutic agents can be tested in an appropriate animal model. For example, an RNAi agent (or expression vector or transgene encoding same) as described herein can be used in an animal model to determine the efficacy, toxicity, or side effects of treatment with said agent. Alternatively, a therapeutic agent can be used in an animal model to determine the mechanism of action of such an agent. For example, an agent can be used in an animal model to determine the efficacy, toxicity, or side effects of treatment with such an agent. Alternatively, an agent can be used in an animal model to determine the mechanism of action of such an agent.

VI. Pharmaceutical Compositions

The invention pertains to uses of the above-described agents for therapeutic treatments as described infra. Accordingly, the modulators of the present invention can be incorporated into pharmaceutical compositions suitable for administration. Such compositions typically comprise the nucleic acid molecule, protein, antibody, or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, intraperitoneal, intramuscular, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

VI. Knockout and/or Knockdown Cells or Organisms

A further preferred use for the RNAi agents of the present invention (or vectors or transgenes encoding same) is a functional analysis to be carried out in eukaryotic cells, or eukaryotic non-human organisms, preferably mammalian cells or organisms and most preferably human cells, e.g. cell lines such as HeLa or 293 or rodents, e.g. rats and mice. By administering a suitable RNAi agent which is sufficiently complementary to a target mRNA sequence to direct target-specific RNA interference, a specific knockout or knockdown phenotype can be obtained in a target cell, e.g. in cell culture or in a target organism.

Thus, a further subject matter of the invention is a eukaryotic cell or a eukaryotic non-human organism exhibiting a target gene-specific knockout or knockdown phenotype comprising a fully or at least partially deficient expression of at least one endogeneous target gene wherein said cell or organism is transfected with at least one vector comprising DNA encoding an RNAi agent capable of inhibiting the expression of the target gene. It should be noted that the present invention allows a target-specific knockout or knockdown of several different endogeneous genes due to the specificity of the RNAi agent.

Gene-specific knockout or knockdown phenotypes of cells or non-human organisms, particularly of human cells or non-human mammals may be used in analytic to procedures, e.g. in the functional and/or phenotypical analysis of complex physiological processes such as analysis of gene expression profiles and/or proteomes. Preferably the analysis is carried out by high throughput methods using oligonucleotide based chips.

Using RNAi based knockout or knockdown technologies, the expression of an endogeneous target gene may be inhibited in a target cell or a target organism. The endogeneous gene may be complemented by an exogenous target nucleic acid coding for the target protein or a variant or mutated form of the target protein, e.g. a gene or a DNA, which may optionally be fused to a further nucleic acid sequence encoding a detectable peptide or polypeptide, e.g. an affinity tag, particularly a multiple affinity tag.

Variants or mutated forms of the target gene differ from the endogeneous target gene in that they encode a gene product which differs from the endogeneous gene product on the amino acid level by substitutions, insertions and/or deletions of single or multiple amino acids. The variants or mutated forms may have the same biological activity as the endogeneous target gene. On the other hand, the variant or mutated target gene may also have a biological activity, which differs from the biological activity of the endogeneous target gene, e.g. a partially deleted activity, a completely deleted activity, an enhanced activity etc. The complementation may be accomplished by compressing the polypeptide encoded by the endogeneous nucleic acid, e.g. a fusion protein comprising the target protein and the affinity tag and the double stranded RNA molecule for knocking out the endogeneous gene in the target cell. This compression may be accomplished by using a suitable expression vector expressing both the polypeptide encoded by the endogenous nucleic acid, e.g. the tag-modified target protein and the double stranded RNA molecule or alternatively by using a combination of expression vectors. Proteins and protein complexes which are synthesized de novo in the target cell will contain the exogenous gene product, e.g., the modified fusion protein. In order to avoid suppression of the exogenous gene product by the RNAi agent, the nucleotide sequence encoding the exogenous nucleic acid may be altered at the DNA level (with or without causing mutations on the amino acid level) in the part of the sequence which is homologous to the RNAi agent. Alternatively, the endogeneous target gene may be complemented by corresponding nucleotide sequences from other species, e.g. from mouse.

VII. Transgenic Organisms

Engineered RNA precursors of the invention can be expressed in transgenic animals. These animals represent a model system for the study of disorders that are caused by, or exacerbated by, overexpression or underexpression (as compared to wildtype or normal) of nucleic acids (and their encoded polypeptides) targeted for destruction by the RNAi agents, e.g., siRNAs and shRNAs, and for the development of therapeutic agents that modulate the expression or activity of nucleic acids or polypeptides targeted for destruction.

Transgenic animals can be farm animals (pigs, goats, sheep, cows, horses, rabbits, and the like), rodents (such as rats, guinea pigs, and mice), non-human primates (for example, baboons, monkeys, and chimpanzees), and domestic animals (for example, dogs and cats). Invertebrates such as *Caenorhabditis elegans* or *Drosophila* can be used as well as non-mammalian vertebrates such as fish (e.g., zebrafish) or birds (e.g., chickens).

Engineered RNA precursors with stems of 18 to 30 nucleotides in length are preferred for use in mammals, such as mice. A transgenic founder animal can be identified based upon the presence of a transgene that encodes the new RNA precursors in its genome, and/or expression of the transgene in tissues or cells of the animals, for example, using PCR or Northern analysis. Expression is confirmed by a decrease in the expression (RNA or protein) of the target sequence.

A transgenic founder animal can be used to breed additional animals carrying the transgene. Moreover, transgenic animals carrying a transgene encoding the RNA precursors can further be bred to other transgenic animals carrying other transgenes. In addition, cells obtained from the transgenic founder animal or its offspring can be cultured to establish primary, secondary, or immortal cell lines containing the transgene.

1. Procedures for Making Transgenic, Non-Human Animals

A number of methods have been used to obtain transgenic, non-human animals, which are animals that have gained an additional gene by the introduction of a transgene into their cells (e.g., both the somatic and genn cells), or into an ancestor's genn line. In some cases, transgenic animals can be generated by commercial facilities (e.g., The Transgenic *Drosophila* Facility at Michigan State University, The Transgenic Zebrafish Core Facility at the Medical College of Georgia (Augusta, Ga.), and Xenogen Biosciences (St. Louis, Mo.). In general, the construct containing the transgene is supplied to the facility for generating a transgenic animal.

Methods for generating transgenic animals include introducing the transgene into the germ line of the animal. One method is by microinjection of a gene construct into the pronucleus of an early stage embryo (e.g., before the four-cell stage; Wagner et al., 1981, Proc. Natl. Acad. Sci. USA 78:5016; Brinster et al., 1985, Proc. Natl. Acad. Sci. USA 82:4438). Alternatively, the transgene can be introduced into the pronucleus by retroviral infection. A detailed procedure for producing such transgenic mice has been described (see e.g., Hogan et al., MP1 ulating the Mouse EmbnLo. Cold Spring Harbour Laboratory, Cold Spring Harbour, N.Y. (1986); U.S. Pat. No. 5,175,383 (1992)). This procedure has also been adapted for other animal species (e.g., Hammer et al., 1985, Nature 315:680; Murray et al., 1989, Reprod. Fert. Devl. 1:147; Pursel et al., 1987, Vet. hnmunol. Histopath. 17:303; Rexroad et al., 1990, J. Reprod. Fert. 41 (suppl): 119; Rexroad et al., 1989, Molec. Reprod. Devl. 1:164; Simons et al., 1988, BioTechnology 6:179; Vize et al., 1988, J. Cell. Sci. 90:295; and Wagner, 1989, J. Cell. Biochem. 13B (suppl): 164).

In brief, the procedure involves introducing the transgene into an animal by microinjecting the construct into the pronuclei of the fertilized mammalian egg(s) to cause one or more copies of the transgene to be retained in the cells of the developing marmnal(s). Following introduction of the transgene construct into the fertilized egg, the egg may be incubated in vitro for varying amounts of time, or reimplanted a in surrogate host, or both. One common method is to incubate the embryos in vitro for about 1-7 days, depending on the species, and then reimplant them into the surrogate host. The presence of the transgene in the progeny of the transgenically manipulated embryos can be tested by Southern blot analysis of a segment of tissue.

Another method for producing germ-line transgenic animals is through the use of embryonic stem (ES) cells. The gene construct can be introduced into embryonic stem cells by homologous recombination (Thomas et al., 1987, Cell 51:503; Capecchi, Science 1989, 244:1288; Joyner et al., 1989, Nature 338:153) in a transcriptionally active region of the genome. A suitable construct can also be introduced into embryonic stem cells by DNA-mediated transfection, such as by 17 electroporation (Ausubel et al., Current Protocols in Molecular Biology, John Wiley & Sons, 1987). Detailed procedures for culturing embryonic stem cells (e.g., ES-D3@ ATCC# CCL-1934, ES-E14TG2a, ATCC# CCL-1821, American Type Culture Collection, Rockville, AM) and methods of making transgenic animals from embryonic stem cells can be found in Teratocarcinomas and Embryonic Stem Cells, A Practical Approach, ed. E. J. Robertson (IRL Press, 1987). In brief, the ES cells are obtained from pre-implantation embryos cultured in vitro (Evans et al., 1981, Nature 292:154-156). Transgenes can be efficiently introduced into ES cells by DNA transfection or by retrovirus-mediated transduction. The resulting transformed ES cells can thereafter be combined with blastocysts from a non-human animal. The ES cells colonize the embryo and contribute to the genn line of the resulting chimeric animal.

In the above methods, the transgene can be introduced as a linear construct, a circular plasmid, or a viral vector, which can be incorporated and inherited as a transgene integrated into the host genome. The transgene can also be constructed to permit it to be inherited as an extrachromosomal plasmid (Gassmann et al., 1995, Proc. Natl. Acad. Sci. USA 92:1292). A plasmid is a DNA molecule that can replicate autonomously in a host.

The transgenic, non-human animals can also be obtained by infecting or transfecting cells either in vivo (e.g., direct injection), ex vivo (e.g., infecting the cells outside the host and later reimplanting), or in vitro (e.g., infecting the cells outside host), for example, with a recombinant viral vector carrying a gene encoding the engineered RNA precursors. Examples of suitable viral vectors include recombinant retroviral vectors (Valerio et al., 1989, Gene 84:419; Scharfinan et al., 1991, Proc. Natl. Acad. Sci. USA 88:462; Miller and Buttimore, 1986, Mol. Cell. Biol. 6:2895), recombinant adenoviral vectors (Freidman et al., 1986, Mol. Cell. Biol. 6:3791; Levrero et al., 1991, Gene 101: 195), and recombinant Herpes simplex viral vectors (Fink et al., 1992, Human Gene Therapy 3:11). Such methods are also useful for introducing constructs into cells for uses other than generation of transgenic animals.

Other approaches include insertion of transgenes encoding the new engineered RNA precursors into viral vectors including recombinant adenovirus, adenoassociated virus, and herpes simplex virus-1, or recombinant bacterial or eukaryotic plasmids. Viral vectors transfect cells directly. Other approaches include delivering the transgenes, in the form of plasmid DNA, with the help of, for example, cationic liposornes (lipofectin) or derivatized (e.g. antibody conjugated) polylysine conjugates, gramacidin S, artificial viral envelopes, or other such intracellular carriers, as well as direct injection of the transgene construct or $CaPO_4$ precipitation carried out in vivo. Such methods can also be used in vitro to introduce constructs into cells for uses other than generation of transgenic animals.

Retrovirus vectors and adeno-associated virus vectors can be used as a recombinant gone delivery system for the transfer of exogenous genes in vivo or in vitro. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, 1990, Blood 76:271). A replication defective retrovirus can be packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al., (eds.) Greene Publishing Associates, (1989), Sections 9 9.14 and other standard laboratory manuals.

Examples of suitable retroviruses include pLJ, pZIP, pWE and pEM which are known to those skilled in the art. Examples of suitable packaging virus lines for preparing both ecotropic and amphotropic retroviral systems include Psi-Crip, PsiCre, Psi-2 and Psi-Am. Retroviruses have been used to introduce a variety of genes into many different cell types, including epithelial cells, in vitro and/or in vivo (see for example Eglitis, et al., 1985, Science 230:1395-1398; Danos and Mulligan, 1988, Proc. Natl. Acad. Sci. USA 85:6460-6464; Wilson et al., 1988, Proc. Natl. Acad. Sci. USA 85:3014-3018; Armentano et al., 1990, Proc. Natl. Acad. Sci. USA 87:61416145; Huber et al., 1991, Proc. Natl. Acad. Sci. USA 88:8039-8043; Ferry et al., 1991, Proc. Natl. Acad. Sci. USA 88:8377-8381; Chowdhury et al., 1991, Science 254:1802-1805; van Beusechem. et al., 1992, Proc. Nad. Acad. Sci. USA 89:7640-19; Kay et al., 1992, Human Gene Therapy 3:641-647; Dai et al., 1992, Proc. Natl. Acad. Sci. USA 89:10892-10895; Hwu et al., 1993, J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

In another example, recombinant retroviral vectors capable of transducing and expressing genes inserted into the genome of a cell can be produced by transfecting the recombinant retroviral genome into suitable packaging cell lines such as PA317 and Psi-CRIP (Comette et al., 1991, Human Gene Therapy 2:5-10; Cone et al., 1984, Proc. Natl. Acad. Sci. USA 81:6349). Recombinant adenoviral vectors can be used to infect a wide variety of cells and tissues in susceptible hosts (e.g., rat, hamster, dog, and chimpanzee) (Hsu et al., 1992, J. Infectious Disease, 166:769), and also have the advantage of not requiring mitotically active cells for infection. Another viral gene delivery system useful in the present invention also utilizes adenovirus-derived vectors. The genome of an adenovirus can be manipulated such that it encodes and expresses a gene product of interest but is inactivated in terms of its ability to replicate in a normal lytic viral life cycle. See, for example, Berkner et al. (1988, BioTechniques 6:616), Rosenfeld et al. (1991, Science 252:431-434), and Rosenfeld et al. (1992, Cell 68:143-155). Suitable adenoviral vectors derived from the adenovirus strain Ad type 5 d1324 or other strains of adenovirus (e.g., Ad2, AO, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al., 1992, cited supra). Furthermore, the virus particle is relatively stable and amenable to purification and concentration, and as above, can be modified to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis hz situ where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham, 1986, J. Virol. 57:267).

Yet another viral vector system useful for delivery of the subject transgenes is the adeno-associated virus (AAV). Adeno-associated virus is a naturally occurring defective virus that requires another virus, such as an adenovirus or a herpes virus, as a helper virus for efficient replication and a productive life cycle. For a review, see Muzyczka et al. (1992, Curr. Topics in Micro. and Immunol. 158:97-129). It is also one of the few viruses that may integrate its DNA into non-dividing cells, and exhibits a high frequency of stable integration (see for example Flotte et al. (1992, Am. J. Respir. Cell. Mol. Biol. 7:349-356; Samulski et al., 1989, J. Virol. 63:3822-3828; and McLaughlin et al. (1989, J. Virol. 62:1963-1973). Vectors containing as little as 300 base pairs of AAV can be packaged and can integrate. Space for exogenous DNA is limited to about 4.5 kb. An AAV vector such as that described in Tratschin et al. (1985) MoL Cell. Biol. 5:3251-3260 can be used to introduce DNA into cells. A variety of nucleic acids have been introduced into different cell types using AAV vectors (see for example Hennonat et al. (1984) Proc. Nad. Acad. Sci. USA 81:64666470; Tratschin et al. (1985) Mol. Cell. BioL 4:2072-2081; Wondisford et al. (1988) MoL EndocrinoL 2:32-39; Tratschin et al. (1984) J ViroL 51:611-619; and Flotte et al. (1993) J BioL Chem. 268:3781-3790).

In addition to viral transfer methods, such as those illustrated above, non-viral methods can also be employed to cause expression of an shRNA or engineered RNA precursor of the invention in the tissue of an animal. Most non-viral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject gene of the invention by the targeted cell. Exemplary gene delivery systems of this type include liposomal derived systems, poly-lysine conjugates, and artificial viral envelopes. Other embodiments include plasmid injection systems such as are described in Meuli et al., (2001) J Invest. DerinatoL, 116(1):131-135; Cohen et al., (2000) Gene Ther., 7(22):1896-905; and Tam et al., (2000) Gene Ther., 7(21):186774.

In a representative embodiment, a gene encoding an shRNA or engineered RNA precursor of the invention can be entrapped in liposomes bearing positive charges on their surface (e.g., lipofectins) and (optionally) which are tagged with antibodies against cell surface antigens of the target tissue (Mizuno et al., (1992) No Shinkei Geka, 20:547-551; PCT publication WO91/06309; Japanese patent application 10473 8 1; and European patent publication EP-A-43 075).

Animals harboring the transgene can be identified by detecting the presence of the transgene in genomic DNA (e.g., using Southern analysis). In addition, expression of the shRNA or engineered RNA precursor can be detected directly (e.g., by Northern analysis). Expression of the transgene can also be confirmed by detecting a decrease in the amount of protein corresponding to the targeted sequence. When the transgene is under the control of an inducible or developmentally regulated promoter, expression of the target protein is decreased when the transgene is induced or at the developmental stage when the transgene is expressed, respectively.

2. Clones of Transgenic Animals

Clones of the non-human transgenic animals described herein can be produced according to the methods described in Wilmut et al. ((1997) Nature, 385:810-813) and PCT publication Nos. WO 97/07668 and WO 97/07669. In brief, a cell, e.g., a somatic cell from the transgenic animal, can be isolated and induced to exit the growth cycle and enter the G0 phase to become quiescent. The quiescent cell can then be fused, e.g., through the use of electrical pulses, to an enucleated oocyte from an animal of the same species from which the quiescent cell is isolated. The reconstructed oocyte is then cultured such that it develops into a morula or blastocyte and is then transferred to a pseudopregnant female foster animal. Offspring borne of this female foster animal will be clones of the animal from which the cell, e.g., the somatic cell, was isolated.

Once the transgenic animal is produced, cells of the transgenic animal and cells from a control animal are screened to determine the presence of an RNA precursor nucleic acid sequence, e.g., using polymerase chain reaction (PCR). Alternatively, the cells can be screened to determine if the RNA precursor is expressed (e.g., by standard procedures such as Northern blot analysis or reverse transcriptase-polymerase chain reaction (RT-PCR); Sambrook et al., Molecular Cloning—A Laboratory Manual, (Cold Spring Harbor Laboratory, 1989)).

The transgenic animals of the present invention can be homozygous or heterozygous, and one of the benefits of the invention is that the target mRNA is effectively degraded even in heterozygotes. The present invention provides for transgenic animals that carry a transgene of the invention in all their cells, as well as animals that carry a transgene in some, but not all of their cells. That is, the invention provides for mosaic animals. The transgene can be integrated as a single transgene or in concatatners, e.g., head-to-head tandems or head-to-tail tandems.

For a review of techniques that can be used to generate and assess transgenic animals, skilled artisans can consult Gordon (IwL Rev. CytoL 115:171-229, 1989), and may obtain additional guidance from, for example: Hogan et al. "Manipulating the Mouse Embryo" (Cold Spring Harbor Press, Cold Spring Harbor, N.Y., 1986; Krimpenfort et al., BiolTechnology 9:86, 1991; Palmiter et al., Cell 41:343, 1985; Kraemer et al., "Genetic Manipulation of the Early Mammalian Embryo," Cold Spring Harbor Press, Cold Spring Harbor, N.Y., 1985; Hammer et al., Nature 315:680, 1985; Purcel et al., Scieizce, 244:1281, 1986; Wagner et al., U.S. Pat. No. 5,175,385; and Krimpenfort et al., U.S. Pat. No. 5,175,384.

3. Transgenic Plants

Among the eukaryotic organisms featured in the invention are plants containing an exogenous nucleic acid that encodes an engineered RNA precursor of the invention.

Accordingly, a method according to the invention comprises making a plant having a nucleic acid molecule or construct, e.g., a transgene, described herein. Techniques for introducing exogenous micleic acids into monocotyledonous and dicotyledonous plants are known in the art, and include, without limitation, *Agrobacterium*-mediated transformation, viral vector-mediated transformation, electroporation and particle gun transformation, see, e.g., U.S. Pat. Nos. 5,204,253 and 6,013,863. If a cell or tissue culture is used as the recipient tissue for transformation, plants can be regenerated from transformed cultures by techniques known to those skilled in the art. Transgenic plants can be entered into a breeding program, e.g., to introduce a nucleic acid encoding a polypeptide into other lines, to transfer the nucleic acid to other species or for further selection of other desirable traits.

Alternatively, transgenic plants can be propagated vegetatively for those species amenable to such techniques. Progeny includes descendants of a particular plant or plant line. Progeny of a plant include seeds formed on F1, F2, F3, and subsequent generation plants, or seeds formed on BQ, BC2, BC3, and subsequent generation plants. Seeds produced by a transgenic plant can be grown and then selfed (or outcrossed and selfed) to obtain seeds homozygous for the nucleic acid encoding a novel polypeptide.

A suitable group of plants with which to practice the invention include dicots, such as safflower, alfalfa, soybean, rapeseed (high erucic acid and canola), or sunflower. Also suitable are monocots such as corn, wheat, rye, barley, oat, rice, millet, amaranth or sorghum. Also suitable are vegetable crops or root crops such as potato, broccoli, peas, sweet corn, popcorn, tomato, beans (including kidney beans, lima beans, dry beans, green beans) and the like. Also suitable are fruit crops such as peach, pear, apple, cherry, orange, lemon, grapefruit, plum, mango and palm. Thus, the invention has use over a broad range of plants, including species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyalnus, Lactuca, Linum, Lolium, Lupinus, Lycopersicon, Malus, Manihot, Majorana, Medicago, Nicotiana, Olea, Oryza, Panicum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna* and *Zea*.

The skilled artisan will appreciate that the enumerated organisms are also useful for practicing other aspects of the invention, e.g., as host cells, as described supra.

The nucleic acid molecules of the invention can be expressed in plants in a cell- or tissue-specific manner according to the regulatory elements chosen to include in a particular nucleic acid construct present in the plant. Suitable cells, tissues, and organs in which to express a chimeric polypeptide of the invention include, without limitation, egg cell, central cell, synergid cell, zygote, ovule primordia, nucellus, integuments, endothelium, female gametophyte cells, embryo, axis, cotyledons, suspensor, endosperm, seed coat, ground meristem, vascular bundle, cambium, phloem, cortex, shoot or root apical meristems, lateral shoot or root meristems, floral meristem, leaf primordia, leaf mesophyll cells, and leaf epidermal cells, e.g., epidermal cells involved in fortning the cuticular layer. Also suitable are cells and tissues grown in liquid media or on semi-solid media.

4. Transgenic Fungi

Other eukaryotic organisms featured in the invention are fungi containing an exogenous nucleic acid molecule that encodes an engineered RNA precursor of the invention. Accordingly, a method according to the invention comprises introducing a nucleic acid molecule or construct as described herein into a fungus. Techniques for introducing exogenous nucleic acids into many fungi are known in the art, see, e.g., U.S. Pat. Nos. 5,252,726 and 5,070,020. Transformed fungi can be cultured by techniques known to those skilled in the art. Such fungi can be used to introduce a nucleic acid encoding a polypeptide into other fungal strains, to transfer the nucleic acid to other species or for further selection of other desirable traits.

A suitable group of fungi with which to practice the invention include fission yeast and budding yeast, such as *Saccharoinyces cereviseae, S. pombe, S. carlsbergeris* and *Candida albicans*. Filamentous fungi such as *Aspergillus* spp. and *Penicillium* spp. are also useful.

VIII. Functional Genomics and/or Proteomics

Preferred applications for the cell or organism of the invention is the analysis of gene expression profiles and/or proteomes. In an especially preferred embodiment an analysis of a variant or mutant form of one or several target proteins is carried out, wherein said variant or mutant forms are reintroduced into the cell or organism by an exogenous target nucleic acid as described above. The combination of knockout of an endogeneous gene by application of a RNA silencing agent of the invention and rescue of the knockout by using mutated, e.g. partially deleted exogenous target has advantages compared to the use of a knockout cell. Further, this method is particularly suitable for identifying functional domains of the targeted protein. In a further preferred embodiment a comparison, e.g. of gene expression profiles and/or proteomes and/or phenotypic characteristics of at least two cells or organisms is carried out. These organisms are selected from: (i) a control cell or control organism without target gene inhibition, (ii) a cell or organism with target gene inhibition and (iii) a cell or organism with target gene inhibition plus target gene complementation by an exogenous target nucleic acid.

Furthermore, the RNA knockout complementation method may be used for is preparative purposes, e.g. for the affinity purification of proteins or protein complexes from eukaryotic cells, particularly mammalian cells and more particularly human cells. In this embodiment of the invention, the exogenous target nucleic acid preferably codes for a target protein which is fused to art affinity tag. This method is suitable for functional proteome analysis in mammalian cells, particularly human cells.

Another utility of the present invention could be a method of identifying gene function in a cell or organism comprising the use of an RNA silencing agent of the invention (e.g. RNAi agent or agent causing translational repression) to inhibit the activity of a target gene of previously unknown function. Instead of the time consuming and laborious isolation of mutants by traditional genetic screening, functional genomics would envision determining the function of uncharacterized genes by employing the RNA silencing agents of the invention to reduce the amount and/or alter the timing of target gene activity.

The invention could be used in determining potential pharmaceutics, potential targets for pharmaceutics, understanding normal and pathological events associated with development, determining signaling pathways responsible for postnatal development/aging, and the like. The increasing speed of acquiring nucleotide sequence information from genomic and expressed gene sources, including total genome sequences for model organisms (e.g. rat, mouse, zebrafish, yeast, *Arabidopsis thalania, D. melanogaster*, and *C. elegans*), can be coupled with the invention to determine gene function in that organisms, a related organism (e.g., a parasitic fly or nematode), or an organism containing a homolog of the gene of interest (e.g. human). The preference of different organisms to use particular codons, searching sequence databases for related gene products, correlating the linkage map of genetic traits with the physical map from which the nucleotide sequences are derived, and artificial intelligence methods may be used to define putative open reading frames from the nucleotide sequences acquired in such sequencing projects. A simple assay would be to inhibit gene expression according to the partial sequence available from an expressed sequence tag (EST). Functional alterations in growth, development, metabolism, disease resistance, or other biological processes would be indicative of the normal role of the EST's gene product.

The ease with which RNA can be introduced into an intact cell or model organism containing the target gene allows the RNA silencing agents of the present invention to be used in high throughput screening (HTS). Solutions containing RNA silencing agents (e.g. RNAi agents or translational repression agents) that are capable of inhibiting the different expressed genes can be placed into individual wells positioned on a microtiter plate as an ordered array, and intact cells organisms in each well can be assayed for any changes or modifications in behavior or development due to inhibition of target gene activity. The amplified RNA can be fed directly to, injected into, the cell/organism containing the target gene. Alternatively, the RNA silencing agent (e.g. RNAi agent or translational repression agent) can be produced from a vector, as described herein. Vectors can be injected into the cell/organism containing the target gene. The function of the target gene can be assayed from the effects it has on the cell/organism when gene activity is inhibited. This screening could be amenable to small subjects that can be processed in large number, for example: *arabidopsis*, bacteria, *drosophila*, fungi, nematodes, viruses, zebrafish, and tissue culture cells derived from mammals. A nematode or other organism that produces a calorimetric, fluorogenic, or luminescent signal in response to a regulated promoter (e.g, transfected with a reporter gene construct) can be assayed in an HTS format.

The present invention may be useful in allowing the inhibition of essential genes. Such genes may be required for cell or organism viability at only particular stages of development or cellular compartments. The functional equivalent of conditional mutations may be produced by inhibiting activity of the target gene when or where it is not required for viability. The invention allows addition of the RNA silencing agent (e.g. RNAi or translational repression agent) at specific times of development and locations in the organism without introducing permanent mutations into the target genome.

siRNA-like silencing agents of the present invention can be used in method for identifying the natural target (e.g., the natural mRNA target) of a miRNA in a cell or organism. An exemplary method comprises contacting a plurality or panel of candidate target genes (e.g., target mRNA sequences), for example, several hundred natural mRNAs represented on a microwell plate). mRNAs can be separated into individual wells positioned on a microtiter plate as an ordered array. The miRNA can then be assessed for its ability to bind to, direct cleavage of, recruit RISC components, or any other indicator of RNA silencing (e.g., by RNAi or translational repression) using methods described herein or routine in the art. In other embodiments, siRNA-like duplexes or miRNAs can be arrayed on plates for testing with a specific target gene or mRNA. In preferred embodiments, the miRNAs are used at low concentrations (e.g. picomolar concentration) to prevent non-specific silencing of the target.

When used to analyse gene expression profiles and/or proteomes, to identify or inhibit gene function, or to validate pharmaceutic targets, the RNA silencing agents of the invention offer improvements over existing RNA silencing agents. The RNA silencing agents of the invention have several-fold improvement in potency (e.g., can be used at picomolar concentrations vs. the nanomolar or micromolar concentrations required when using unmodified, e.g., symmetrical silencing agents) so that lower and more economical amounts of these reagents can be used for the methods described supra. Alternatively, the use of the RNA silencing agents of the invention may obviate the need for costly chemical modifications.

IX. Screening Assays

The methods of the invention are also suitable for use in methods to identify and/or characterize potential pharmacological agents, e.g. identifying new pharmacological agents from a collection of test substances and/or characterizing mechanisms of action and/or side effects of known pharmacological agents. In one exemplary embodiment, a library of pharmaceutical agents can be screened to identify a pharmaceutical agent which suppresses or "rescues" the gene silencing phenotype in a cell or organism caused by previous administration of the RNA silencing agent.

Thus, the present invention also relates to a system for identifying and/or characterizing pharmacological agents acting on at least one target protein comprising: (a) a eukaryotic cell or a eukaryotic non-human organism capable of expressing at least one endogenous target gene coding for said so target protein, (b) at least one silencing agent (e.g. RNAi agent) molecule capable of inhibiting the expression of said at least one endogenous target gene, and (c) a test substance or a collection of test substances wherein pharmacological properties of said test substance or said collection are to be identified and/or characterized. Further, the system as described above preferably comprises: (d) at least one exogenous target nucleic acid coding for the target protein or a variant or mutated form of the target protein wherein said exogenous target nucleic acid differs from the endogenous target gene on the nucleic acid level such that the expression of the exogenous target nucleic acid is substantially less inhibited by the silencing agent (e.g. RNAi agent) than the expression of the endogenous target gene.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) Nature 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.)).

In a preferred embodiment, the library is a natural product library, e.g., a library produced by a bacterial, fungal, or yeast culture. In another preferred embodiment, the library is a synthetic compound library.

When used in the screening assays described herein, the RNA silencing agents of the invention offer improvements in potency over existing RNA silencing agents. For example, the RNA silencing agents of the invention have several-fold improvement in potency (picomolar vs. micromolar) such that lower and more economical amounts of these reagents can be used for the methods described supra. Alternatively, the use of the RNA silencing agents of the invention may obviate the need for costly chemical modifications.

This invention is further illustrated by the following examples which should not be construed as limiting. The contents of all references, patents and published patent applications cited throughout this application are incorporated herein by reference.

EXAMPLES

Example I

Functionally Asymmetric siRNA Duplexes

To assess quantitatively if the two strands of an siRNA duplex are equally competent to direct RNAi, the individual rates of sense and anti-sense target cleavage for an siRNA duplex directed against the firefly luciferase mRNA were examined (FIG. 1A). The relevant portions of the sense and anti-sense target RNA sequences are shown in FIG. 1A and the siRNA sequence in FIG. 1B. This siRNA duplex effectively silences firefly luciferase expression in culture human HeLa cells. Using a *Drosophila* embryo-derived in vitro RNAi reaction, a significant difference in the rate of target cleavage for the two siRNA strands was found; the anti-sense siRNA strand directed more efficient RNAi against a sense RNA target than the sense siRNA strand for an anti-sense target (FIG. 1B). (Anti-sense siRNA strands and sense target RNAs are always shown in black, and sense siRNAs and anti-sense targets, in grey). Control experiments showed that using siRNA duplexes with 5' phosphates did not alter this result (data not shown), indicating that different rates of phosphorylation for the two strands is not the cause for the observed asymmetry. Surprisingly, the two stands of the luciferase duplex siRNA duplex, used individually as 5' phosphorylated single stands, had identical rates of target cleavage (FIG. 1C). RNAi directed by single-stranded siRNA is roughly 10-fold less efficient than that triggered by siRNA duplexes, reflecting the ~100-fold lower stability of single-stranded siRNAs in vitro and in vivo (Schwarz et al., 2002). The difference in the rate of cleavage directed by the sense and anti-sense strands when the reaction was programmed with an siRNA duplex is unlikely to reflect a difference in the inherent susceptibility of the two targets to RNAi. Instead, the observation that the same two siRNA strands are equally effective as single-strands, but show dramatically different activities when paired with each other, indicates that the asymmetry in their function is established at a step in the RNAi pathway prior to the encounter of the programmed RISC with its corresponding RNA target.

Example II

Differential RISC Assembly Accounts for siRNA Strand Functional Asymmetry

To identify the source of asymmetry in the function of this siRNA duplex, the unwinding of the two siRNA strands when the duplex was incubated in a standard in vitro RNAi reaction was measured. This assay was shown previously to determine accurately the fraction of siRNA that is unwound in an ATP-dependent step in the RNAi pathway; no functional RISC is assembled in the absence of ATP (Nykänen et al., 2001). Previous studies show that siRNA unwinding correlates with capacity of an siRNA to function in target cleavage (Nykänen et al., 2001; Martinez et al., 2002), demonstrating that siRNA duplex unwinding is required to assemble a RISC competent to base pair with its target RNA. Here, the accumulation of single standed siRNA from the luciferase siRNA duplex after 1 hour incubation in an in vitro RNAi reaction in the absence of target RNA was measured. After one hour of incubation with *Drosophila* embryo lysate in a standard RNAi reaction, 22% of the anti-sense strand of the luciferase siRNA was converted to single-strand (FIG. 1D; 'siRNA B' solid black bar). Remarkably, a corresponding amount of single-stranded sense siRNA was not detected. Instead, only 3% of the sense strand accumulated as single-stranded siRNA (FIG. 1D; 'siRNA B' solid grey bar). In control experiments, no single-stranded RNA was detected without incubation in lysate (not shown), demonstrating that the siRNA was entirely double-stranded at the beginning of the reaction. Since the production of single-stranded anti-sense siRNA must be accompanied by an equal amount of single-stranded sense siRNA, the missing sense-strand must have been destroyed after unwinding.

To establish that the observed asymmetry in the accumulation of the two single-strands was not an artifact of our unwinding assay, an independent method for measuring the fraction of siRNA present as single-strands in protein-RNA complexes was. In this assay, double-stranded siRNA was incubated with *Drosophila* embryo lysate in a standard RNAi reaction for 1 h, then a 31 nt 2'-O-methyl RNA oligonucleotide containing a 21 nt sequence complementary to the radiolabeled siRNA strand was added. 2'-O-methyl oligonucleotides are not cleaved by the RNAi machinery, but can bind stably to complementary siRNA within the RISC (Martin Simard, G H, Craig Mello, and PDZ, manuscript in preparation). To allow recovery of RISC, the 2'-O-methyl oligonucleotide was tethered to a magnetic bead via a biotin-streptavidin linkage. After washing away unbound RNA and protein, the amount of radioactive siRNA bound to the bead was measured. The assay was performed with separate siRNA duplexes in which either the sense or the anti-sense strand was 5'-$^{32}$P-radiolabeled. Capture of $^{32}$P-siRNA was observed when the 2'-O-methyl oligonucleotide contained a 21-nt region complementary to the radiolabeled siRNA strand, but not when an unrelated oligonucleotide was used. The assay captures all RISC activity directed by the siRNA strand complementary to the tethered oligonucleotide, demonstrating that it measures siRNA present in the lysate as single-strand complexed with RISC proteins. This assay recapitulates the results of the unwinding assay described above: for the siRNA in FIG. 1D; 'si RNA B' open bars, nearly ten-fold more anti-sense siRNA was detected than sense strand. An explanation for these results is that the two strands of this siRNA duplex are differentially loaded into the RISC, and that single-stranded siRNA not assembled into RISC is degraded. Functional asymmetry occurred only when the trigger siRNA was double-stranded, not when the two siRNA strands were tested individually (FIGS. 1B and 1C). Thus, asymmetric assembly of RISC was a feature of the siRNA duplex, rather than of either the sequences of the individual siRNA strands or the accessibility of the targeted sites to cleavage.

Example III

Base-Pairing at the 5' End of the siRNA Strand Gates RISC Assembly

The finding that the two siRNA strands can have different capacities to form RISC when paired in a duplex indicates that some feature of the 19 base-pairs of the duplex determines functional asymmetry. These base-pairs must be disrupted to produce RISC (Nykänen et al., 2001), which contains single-stranded siRNA (Martinez et al., 2002). The siRNAs used in FIG. 1B were examined for base-pairing features that might distinguish the two siRNA strands. For the siRNA in FIG. 1B, the 5' end of the anti-sense siRNA strand begins with U and is thus paired to the sense siRNA strand by an A:U base pair (2 hydrogen bonds). In contrast, the 5' nucleotide of the sense siRNA strand is linked to the anti-sense strand by a C:G base pair (3 hydrogen bonds). The sense siRNA strand forms 8-10-fold less RISC and guides cleavage of its RNA target at a correspondingly slower rate than the anti-sense strand. A working hypothesis to explain the observed functional asymmetry is that the siRNA strand whose 5' end is more weakly bound to the complementary strand more readily incorporates into RISC. In this view, the relative base-pairing strengths of the 5' ends of the two siRNA strands would determine their relative extents of RISC formation.

As an initial test of this idea, the 5' nucleotide of the siRNA sense strand was changed from C to U (FIG. 1E). This changed the base pair formed between the 5' most nucleotide of the sense strand and position 19 of the anti-sense strand from the Watson-Crick base pair C:G to the weaker, less stable wobble pair U:G, while leaving the anti-sense strand of the siRNA unaltered. Remarkably, the change of this single nucleotide not only enhanced the rate of cleavage directed by the sense strand, but virtually eliminated the ability of the anti-sense strand to direct RNAi (FIG. 1E).

To determine the basis for the reversed functional asymmetry for the siRNA in FIG. 1E, the amount of each strand that was single stranded after incubation of the siRNA duplex in *Drosphilia* embryo lystae was determined. After 1 h, nearly 30% of the sense siRNA strand was converted to single stranded, but no single-stranded anti-sense strand was detected (FIG. 1D; 'siRNA E'). Therefore, the simplest explanation for the asymmetric function of this siRNA is that the sense strand, but not the anti-sense, of this siRNa duplex was incorporated into RISC. Thus, a single nucleotide mutation in the sense siRNA strand of the siRNA in FIG. 1B completely reversed the relative abilites of the two strands to assemble in the enzyme complex that directs RNAi.

The stability of the initial five base pairs of the siRNA strands was claculated in FIG. 1 using the nearest-neighbor method and the mfold algorithm (D. H. Mathews, 1999; Zuker, 2003). The 5' end of the sense siRNA strand in FIG. 1E, but not that in 1B, is predicted to exist as an equilibrium of two conformers of nearly equal energy (FIG. 10). In one conformer, the 5' nucleotide of the sense strand is bound to the anti-sense strand by a U:G wobble pair, whereas in the other conformer the 5' end of this siRNA strand is unpaired. The analysis suggests that RISC assembly favors the siRNA strand whose 5' end has a greater propensity to fray.

To test this hypothesis further, the strand-specific rates of cleavage of sense and anti-sense human Cu, Zn superoxide dismutase-1 (sod1) RNA targets (FIG. 3A) triggered by the siRNA duplex shown in FIG. 3B were examined. Given that the 5' ends of both siRNA strands of this duplex are in G:C base pairs, it was anticipated that this duplex would not display pronounced target cleavage asymmetry. As shown in FIG. 3B, the two strands are similar in their rates of target cleavage, although the rate of anti-sense cleavage directed by the sense-strand is clearly faster than the rate of sense-target cleavage guided by the anti-sense strand. This small difference in rate is likely explained by the sense-strand forming 20 base pairs with its target RNA, whereas the anti-sense strand can form only 19, consistent with previous reports that the penultimate position of an siRNA makes a small contribution to its efficacy (Elbashir et al., 2001b). Next, the C at position 19 of the sense strand was changed to A, causing the anti-sense strand to begin with an unpaired nucleotide. This change, which was made to the sense-strand of the siRNA, caused the rate of target cleavage guided by the anti-sense siRNA strand to be dramatically enhanced and the sense strand rate to be suppressed (FIG. 3C). Because the enhancement of sense target cleavage was caused by a mutation in the sense siRNA strand, which does not participate in the recognition of the sense target, the effect of the mutation must be on a step in the RNAi pathway that is spatially or temporally coupled to siRNA unwinding. However, the suppression of anti-sense target cleavage clearly might have resulted from the single-nucleotie mismatch between the sense strand and its target RNA generated by the C-to-U substitution.

To test if the suppression of the rate of anti-sense target cleavage was a consequence of the position 19 mismatch, a different strategy was used to unpair the 5' end of the anti-sense strand. FIG. 3D shows an siRNA in which the sense-strand is identical to that in FIG. 3B, but the first nucleotide of the anti-sense strand has been changed from G to U, creating a U-C mismatch at its 5' end, in place of the G-A of FIG. 3C. Nonetheless, this siRNA duplex showed pronounced asymmetry, with the anti-sense strand guiding target cleavage to the nearly complete exclusion of the sense strand (FIG. 3D). Thus, the suppression of the cleavage rate of the sense-strand in FIG. 3C was not a consequence of the position 19 mismatch. This finding is consistent with previous studies that suggest that mismatches with the target RNA are well tolerated if they occur near the 3' end of the siRNA guide strand (Amarzguioui et al., 2003). The finding that the siRNAs in FIGS. 3C and 3D display profound asymmetry demonstrates that both the enhancement of the target cleavage rate of the anti-sense strand and the suppression of the function of the sense strand is a consequence of their relative abilities to enter the RNAi pathway, not their intrinsic capacity to direct target cleavage.

Finally, the sense strand of FIG. 3C was paired with the anti-sense strand of FIG. 3D to create the siRNA duplex shown in FIG. 3E. The sense strand of this siRNA, like that in FIG. 3C, contains a mismatch with the anti-sense target at position 19. Like the anti-sense siRNA strand in FIG. 3D, the anti-sense strand contains a mismatch with the sense target at position 1. This siRNA duplex directs target anti-sense cleavage significantly better than the siRNA in FIG. 3C, despite the fact that the two siRNAs contain the same sense strand (FIG. 3E).

FIGS. 3F, G, and H show a similar analysis in which the 5' end of the sense strand or position 19 of the anti-sense strand of the siRNA in FIG. 3B was altered to produce siRNA duplexes in which the 5' end of the sense strand was either fully unpaired (FIGS. 3F and G) or paired in an A:U base pair (FIG. 3H). Again, unpairing the 5' end of an siRNA strand—the sense strand, in this case—caused that strand to function to the exclusion of the other strand. When the sense strand 5' end was present in an A:U base pair and the anti-sense strand 5' end was in a G:C pair, the sense strand dominated the reaction (FIG. 3H), although now the anti-sense strand showed activity similar to that seen for the original siRNA (FIG. 3B) in which both strands were in G:C pairs at their 5' ends. Converting the unpaired 5' end of the siRNAs in FIG. 3 to an A:U pair reduced the functional asymmetry of the two strands by enhancing the efficacy of the sense strand (FIG. 3E) or the anti-sense strand (FIG. 3H). The relative ease with which the 5' ends of the two siRNAs can be liberated from the duplex determines the degree of asymmetry. Additional data supporting this idea is shown in FIG. 8, using a different siRNA. FIG. 8B shows an siRNA that cleaved the two sod1 target RNAs (FIG. 8A). with modest functional asymmetry that reflects the collective base pairing strength of the first four or five nucleotides of each siRNA strand (FIG. 8E; see below). Asymmetry was dramatically increased when a G:U wobble was introduced at the 5' end of the anti-sense strand of the siRNA (FIG. 8C), but no asymmetry was seen when the individual single-strands strands were used to trigger RNAi (FIG. 8D), demonstrating that differential RISC assembly, not target accessibility, explains the functional asymmetry of the siRNA duplex.

Together, the data in FIGS. 1, 2, and 8 indicates that the symmetry of RISC assembly is determined by a competition between the fraying of the 5' ends of the two siRNAs in the duplex. Such fraying may initiate a directional process of unwinding in which the strand at which unwinding is initiated preferentially enters RISC. Such a model requires that either that RISC assembly factors or RISC components themselves are loaded onto one of the two siRNA strands before unwinding is completed, or that information about the siRNA strands prior state of pairing is retained, perhaps by a protein such as the helicase remaining bound to a strand.

Example IV

A Single Hydrogen Bond can Determine which Strand of an siRNA Duplex Directs RNAi To explore this hypothesis further, additional changes were made to the sod1-specific siRNA in FIG. 3. These modifications alter the function of the two strands of the siRNA, but do not change the site cleaved on the two target RNA's. In FIG. 3A, the anti-sense strand of FIG. 3B was paired with a sense strand identical to that in FIG. 3B except the 5' G was replace with inosine (I). Like G, I pairs with C, but makes two instead of three hydrogen bonds. In this respect, an I:C pair is similar in energy to an A:U pair. The resulting siRNA was functionally asymmetric, when the sense-strand began with an I, it directed teargest cleavage more efficiently than antisense-strand (FIG. 4A). The asymmetry reflects an enhancement in efficacy of the sense siRNA strand, with little loss in the function of the anti-sense strand. An inosine at the 5' end of the anti-sense strand had the opposite effect. When the G at position 1 of the anti-sense strand was substituted with inosine and the sense strand is that of FIG. 3B, the anti-sense strand was enhanced relative to the sense strand (FIG. 4B). Thus, the strand whose 5' end is in the weaker base pair was more effective at target cleavage. Remarkably, when the 5' nucleotides of both siRNA strands engage in I:C base pairs (FIG. 4C), the relative efficacy of the two siRNA strands is restored to that reported in FIG. 3B. The slightly faster rate for anti-sense target cleavage than for sense target cleavage is also seen for RNAi triggered with the individual, inosine-containing single strands, indicating that it reflects a difference in the intrinsic capacity of the two strands to guide cleavage, rather than a difference in RISC assembly. Although the relative rates of cleavage of the two strands are comparable for the siRNAs in FIGS. 3B and 4C, the absolute rates are faster for the siRNA in FIG. 4C. These data indicate that production of RISC from an individual strand is governed both by the relative propensity of the siRNA 5' end to fray compared to that of its complementary strand and by the absolute propensity of the siRNA 5' end to fray. This latter finding is particularly unexpected, in that it shows that a difference of a single hydrogen bond has a marked effect on the rate of RISC assembly. siRNA end fraying provides an entry site for an ATP-dependent RNA helicase that unwinds siRNA duplexes (FIG. 4). The helicase makes many abortive attempts to dissociate the two siRNA strands before succeeding to load one strand into RISC. The involvement of a helicase in RISC assembly is supported by previous observations:

(1) both siRNA unwinding and production of functional RISC require ATP in vitro (Nykänen et al., 2001) and (2) several proteins with sequence homology to ATP-dependent RNA helicases have been implicated in RNA silencing (Wu-Scharf et al., 2000; Dalmay et al., 2001; Hutvágner and Zamore, 2002; Ishizuka et al., 2002; Kennerdell et al., 2002; Tabara et al., 2002; Tijsterman et al., 2002).

The effect of single-nucleotide mismatches in this region of the siRNA, using a series of siRNAs containing a mismatch at the second, third, or fourth position of each siRNA strand was further tested. The siRNAs bearing G:U wobble pairs at the second, third, or both second and third positions (FIG. 11) was also analyzed. The results of this series demonstrate that mismatches, but not G:U wobbles, at positions 2-4 of an siRNA strand alter the relative loading of the two siRNA strands into RISC. Mismatches at position five, have very modest effects on the relative loading of the siRNA strands into RISC (data not shown). In contrast, the effects of internal mismatches at positions 6-15 cannot be explained by their influencing the symmetry of RISC assembly (data not shown). In sum, these data are consistent with the action of a non-processive helicase that can bind about four nucleotides of RNA.

Example V

Implications of siRNA Asymmetry in miRNA Biogenesis

One implication of the findings presented herein is that although siRNAs are predominantly present as duplexes at steady state in vitro (Nykänen et al., 2001) and perhaps in vivo (Hamilton and Baulcombe, 1999; Djikeng et al., 2001), both strands of an siRNA are unlikely to be present equally in RISC. That is, the strength of the base pairs at the 5' ends of the two siRNA strands can influence their accumulation as single-strands. When the 5' end of one strand is unpaired, this asymmetry can be nearly absolute. This observation suggested that asymmetric incorporation into RISC, as a consequence of directional unwinding from a frayed end of an siRNA duplex, might also explain why miRNAs accumulate as single strands. Animal miRNAs are derived from the double-stranded stem of ~70 nt stem-loop precursor RNAs (Lee et al., 1993; Pasquinelli et al., 2000; Reinhart et al., 2000; Lagos-Quintana et al., 2001; Lau et al., 2001; Lee and Ambros, 2001; Lagos-Quintana et al., 2002). pre-miRNAs stems are only partially double-stranded; the typical pre-miRNA contains mismatches, internal loops, and G•U base pairs predicted to distort an A-form RNA helix. miRNAs are generated from pre-miRNAs by the double-stranded RNA-specific endonuclease Dicer (Hutvágner et al., 2001; Grishok et al., 2001; Ketting et al., 2001). It was previously proposed by the instant inventors that miRNAs are single-stranded because helical discontinuities constrain Dicer to break only two, rather than four, phosphodiester bonds, yielding a single-stranded miRNA, rather than an siRNA-like duplex (Hutvágner et al., 2001). Such a mechanism has precedent, because E. coli RNase III can be constrained by helical distortions to make only one or two breaks in an RNA chain (Chelladurai et al., 1993).

An alternative hypothesis is that the Dicer cleaves four phosphodiester bonds in all of its subtrates, both long dsRNA and pre-miRNAs, and always generates a product with the essential siRNA duplex (Hutvágner and Zamore, 2002; Reinhart et al., 2002; Lim et al., 2003b). This mechanism for miRNA production was originally suggested by Bartel and colleagues. Using a small RNA cloning strategy to identify mature miRNAs in C. elegans, they recovered small RNAs corresponding to the non-miRNA side of the precursor's stem (Lim et al., 2003b). Although these 'miRNA*' sequences were recovered at about 100 times lower frequency than the miRNAs themselves, they could always be paired with the corresponding miRNA to give 'miRNA duplexes' with 2 nt overhanging 3' ends (Lim et al., 2003b). Their data suggest that miRNAs are born as duplexes, but accumulate as single-strands because some subsequent process stabilizes the miRNA, destabilizes the miRNA*, or both.

The incorporation of miRNA into RISC is this process. Our results with siRNA suggest that preferential assembly of a miRNA into the RISC would be accompanied by destruction of the miRNA. If the rate asymmetric RISC assembly was faster than the production of the miRNA duplexes, only single-stranded miRNAs would be observed at steady-state (FIG. 4). The accumulation of single-strands and not duplexes for miRNAs would simply be a consequence of Dicer being significantly less efficient in cleaving pre-miRNAs compared to long dsRNA (Hutvágner et al., 2001). The rate of asymmetric RISC assembly might be faster than the production of miRNA duplexes, so only single-stranded miRNAs would be observed at steady-state. Two key predictions of this hypothesis are that (1) purified Dicer should cleave pre-miRNAs into equal amounts of miRNA and miRNA* products and (2) pre-miRNA structures should be processed by Dicer into duplexes with the 5' end of the miRNA strand frayed or weakly hydrogen bonded and the 5' end of the miRNA* strand more securely base paired.

A. Dicer Cleaves Pre-let-7 Symmetrically

To begin to test the idea that pre-miRNA are cleaved by Dicer to generate a product with an essential structure of an siRNA a duplex, we incubated the Drosophila pre-miRNA, pre-let-7, with purified, recombinant Dicer and analyzed the products by Northern hybridization using probes specific for either the 5' side of the precursor stem that encodes mature let-7 or for products derived from the 3' side of the precursor stem (let-7* products). As a control, the let-7 precursor RNA was incubated in Drosophila embryo lysate, which recapitulates both pre-let-7 maturation and RNAi in vitro. As previously reported, incubation of pre-let-7 RNA in the lysate produced a single band corresponding to authentic let-7, but no let-7* products (Hutvágner et al., 2001; FIGS. 5A and 5B). In contrast, incubation of pre-let-7 with Dicer yielded approximately equal amounts of let-7 and let-7* products. At least three distinct RNAs were generated from each side of the stem, rather than the single band corresponding to mature let-7 observed in the embryo lysate. Thus, the absence of let-7* in vivo and in the embryo lysate reaction cannot be explained by the influence of pre-let-7 structure on Dicer.

B. Asymmetric RISC Assembly Explains why miRNAs are Single-Stranded

If Dicer cleaves both sides of the pre-let-7 stem, then some step downstream from Dicer action selects mature let-7 from an siRNA-like duplex in which let-7 is paired with let-7*. A good candidate for such a step would be the asymmetric incorporation of let-7 into RISC, accompanied by the degradation of let-7*. To test this idea, the siRNA that might be formed if pre-let-7 were cleaved by Dicer into an siRNA duplex-like structure was deduced. The sequence of this 'pre-let-7 siRNA,' generated by 'conceptual dicing,' is shown in FIG. 6A (see below). Notably, the 5' end of let-7 is unpaired in this duplex, whereas the 5' end of the let-7* strand is in an A:U base pair. The results presented in FIGS. 2, 3, and 4 suggest that this structure should cause the let-7 strand to enter the RISC to the near exclusion of the let-7* strand, which would consequently be degraded.

C. miRNA Versus miRNA* Selection in *Drosophila*

This analysis was next extended to the other published *Drosophila* miRNA genes (Lagos-Quintana et al., 2001). For each precursor structure, the double-strand predicted to be produced by Dicer. These conceptually diced duplexes are shown in FIG. 6A. For 23 of the 27 duplexes generated by this analysis (including pre-let-7), the difference in the base pairing of first five nucleotides of the miRNA versus miRNA* strands accurately predicted the miRNA, and not the miRNA, * accumulates in vivo. The analysis succeeded irrespective of which side of the pre-miRNA stem encoded the mature miRNA. This analysis, previous observations that single mismatches in the first four nucleotides of an siRNA strand, an initial G:U wobble pair, but not internal G:U wobbles, directed the asymmetric incorporation of an siRNA strand into RISC (FIGS. 1, 2, 3, 8, 9, and 11). However, no difference was discerned in the propensity to fray of the 5' ends of the miRNA and * strands for miR-4, miR-5, the three miR-6-2 paralogs, and miR-10. Therefore, it could not be explained why a particular strand would accumulate as the mature miRNA for these three miRNA precursors. miR-5 and miR-10, like other *Drosophila* miRNAs, were identified by the cloning and sequencing of small RNAs from embryos (Lagos-Quintana et al., 2001). Determinants other than end fraying appear to function in the selection of miR-4 and miR-6; these unknown determinants may also play a role in the assembly of an siRNA atrand into RISC. However, miR-5 and miR-10 were cloned only once, raising the possibility that miR-5* or miR-10* is present in embryos, but not represented among the library of small RNA's from which the miRNAs were cloned. Similarly, miR-6 is encoded by three paralogous genes, only one of which we predict to produce detectable amounts of the miR*, so this * strand might have also gone undetected. To test if both the miRNA and * strands might accumulate for some or all of these three genes, Northern hybridization was used to examined the relative abundance of miR-10 and miR-10* in adult *Drosophila* males and females, and in syncitial blastoderm embryos. The results detected both miR-10* and mi-R10 in vivo (FIG. 6C). In fact, the results indicated that more miR-10* was detected that miR-10 in adult males. This finding strengthens the proposal that miRNA genes (i.e., premiRNA's) uniquely specify on which side of the stem the miRNA residues by generating siRNA-like duplexes from which only one of the two strands of the duplex is assembled into RISC. When these double-stranded intermediates do not contain structural features enforcing asymmetric RISC assembly, both strands accumulate in vivo. It is possible that pre-miRNAs such as pre-miR-10, which generates roughly equal amounts of small RNA products from both sides of the precursor stem, simultaneously regulate target RNAs with partial complementary to both small RNA products.

Example VI

Increased Rate of siRNA Efficency Through the Use of dTdT Tails

Figure 12:
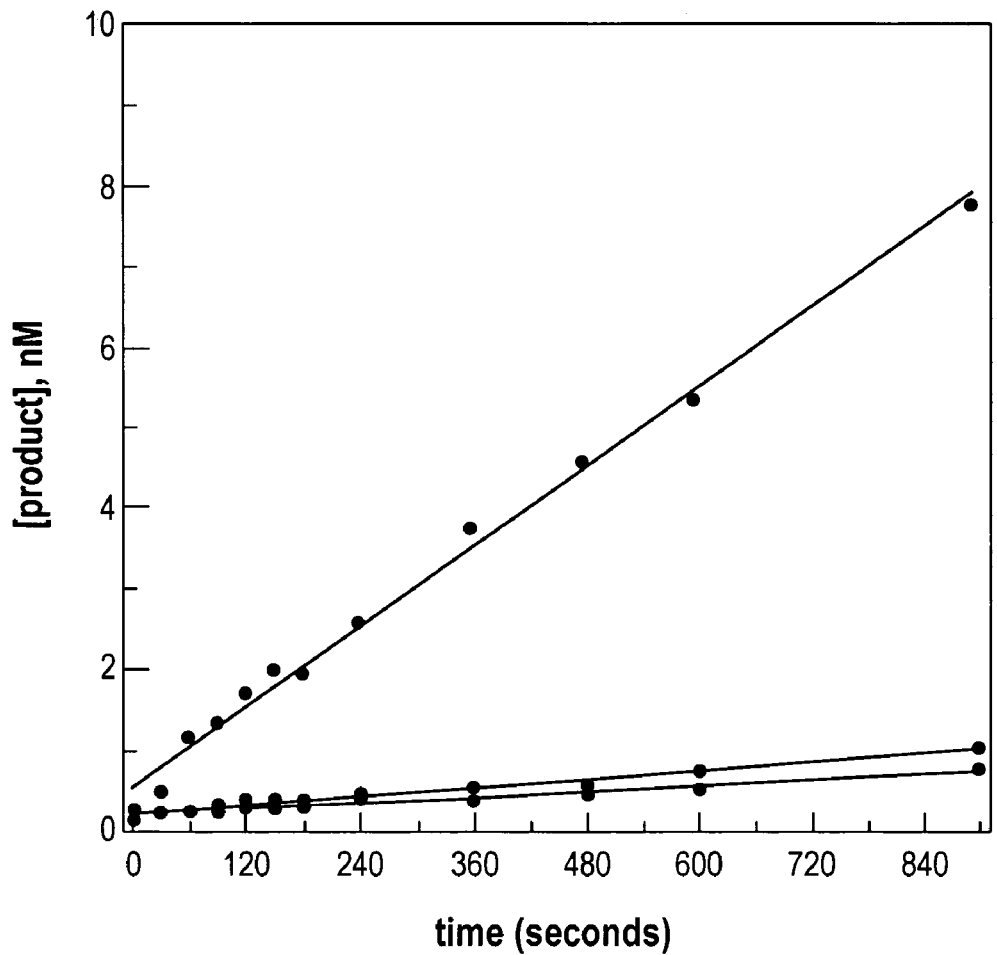
FIG. 12. Increased rate of siRNA efficiency when duplexes have dTdT mismatched tails.

Art-recognized protocols for designing siRNA duplexes teach the inclusion of dTdT tails (i.e., 2-nucleotide overhangs consisting of dTs). Two duplexes were created to test whether the addition of 3' overhanging dTdT tails increases the rate of siRNA taegeting efficiency of the Cu, Zn superoxide-dismutase-1 (Sod1) mRNA. The first duplex contained sense and antisense stands, each including 21 nucleotides with 19 complementary bases plus 2-nucleotide overhangs (the overhangs onsisting of bases in common with the target sequence). The second duplex contained sense and antisense strands, each including 19 complementary nucleotides (in common with the Sod1 target), plus 2-nucleotide dTdT tails at the 5' end of the strand (not matching the Sod1 target). Results demonstrate that the rate of siRNA efficiency improved~8 fold~when using the duplex having mismatched dTdT tails (FIG. 12).

Discussion of Examples I-VI

Implications for RNA Silencing

The observations described herein provide rules for siRNA design. Clearly, siRNA structure can profoundly influence the entry of the anti-sense siRNA strand into the RNAi pathway. Thus, the sequence of the siRNA, rather than that of the target site, may explain at least some previous reports of ineffective siRNAs duplexes. Such inactive duplexes may be coaxed back to life by modifying the sense strand of the siRNA to reduce the strength of the base pair at the 5' end of the anti-sense strand. An example of this in vitro is shown in FIG. 9, for an ineffective siRNA directed against the huntingtin (htt) mRNA (FIG. 9A). Changing the G:C (FIG. 9B) to an A:U pair (FIG. 9C) or a G-A mismatch (FIG. 9D) dramatically improved its target cleavage rate in vitro and its efficacy in vivo (Eftim Milkani, NA, and PDZ, unpublished observations). In fact, Khvorova and colleagues have found that a low base-pairing stability at the 5' end of the antisense strand, but not the sense strand, is a prerequisite for siRNA function in cultured mammalian cells (Anastasia Khvorova, Angela Reynolds, and Sumedha D. Jayasena, manuscript submitted).

siRNAs designed to function asymmetrically may also be uses to enhance RNAi specificity. Recently, expression profiling studies have shown that the sense-strand of an siRNA can direct off-target gene silencing (A. L. Jackson, et al. (2003) *Nature Biotechnology*, May 18; Smizarov et al., PNAS, 2003; Chi et al., PNAS, 2003). The data presented herein provide a strategy for eliminating such sequence-specific but undesirable effects: redesigning the siRNA so that only the anti-sense strand enters the RNAi pathway.

The observations described herein provide new design rules for the construction of short hairpin RNAs (shRNAs), which produce siRNAs transcriptionally in cultured cells or in vivo (Brummelkamp et al., 2002; McManus et al., 2002; Paddison et al., 2002; Paul et al., 2002; Sui et al., 2002; Yu et al., 2002). shRNA strategies typically employ a Pol III promoter to drive transcription, so the shRNA must begin with several G residues. As a consequence, the 5' end of the siRNA may be sequestered in a G:C base pair, significantly reducing entry of the anti-sense strand into the RNAi pathway. To avoid this problem, the anti-sense strand of the desired siRNA can be placed on the 3' side of the loop, so as to ensure that its 5' end is in an A:U, rather than the G:C pair typically encoded. Alternatively, the hairpin can be designed to place the 5' end of the anti-sense siRNA strand in a mismatch or G•U base pair, in which case it can be placed on either side of the stem. Moreover, a recent report suggests that some shRNAs may induce the interferon response (Bridge et al., 2003). The data suggest that mismatches and G:U pairs could be designed into these shRNAs simultaneously to promote entry of the correct siRNA strand into the RNAi pathway and to diminish the capacity of the shRNA stem to trigger non-sequence specific responses to double-stranded RNA.

Finally, the data identify an unanticipated step in the RNAi pathway: the direct coupling of siRNA unwinding to RISC assembly. This finding suggests that the helicase responsible for unwinding siRNA duplexes will be intimately linked to other components of the RNAi machinery. Identifying the helicase and the proteins with which it functions to assemble the RISC is clearly an important challenge for the future.

Example VII

The siRNA-Programmed RISC is an Enzyme

RISC programmed with small RNA in vivo catalyzes the destruction of target RNA in vitro without consuming its small RNA guide (Tang et al., 2003) (Hutvàgner et al., 2002). To begin a kinetic analysis of RISC, the RISC programmed in vitro with siRNA is likewise a multiple-turnover enzyme was first confirmed. To engineer an RNAi reaction that contained a high substrate concentration relative to RISC, an siRNA was used in which the guide strand is identical to the let-7 miRNA, but unlike the miRNA, the let-7 siRNA is paired to an RNA strand anti-sense to let-7(Hutvàgner et al., 2002). The let-7 strand of this siRNA has a high intrinsic cleaving activity, but a reduced efficiency of incorporation into RISC (FIG. 19A).

After incubating the let-7 siRNA with *Drosophila* embryo lysate in the presence of ATP, RISC assembly was inactivated by treatment with N-ethyl maleimide (NEM), and the amount of RISC generated was measured using the previously described tethered 2'-O-methyl oligonucleotide assay (Hutvagner et al., 2004; Schwartz et al., 2003) (FIG. 19B,C). The amount of let-7 programmed RISC increased with increasing siRNA concentration, until the assembly reaction began to saturate at ~50 nM, reaching an asymptote between 3 and 4 nM RISC. Using 0.6 nM RISC, >50 cycles of target recognition and cleavage per enzyme complex (data not shown) was observed, confirming that siRNA-programmed RISC is a multiple-turnover enzyme.

Example VIII

Multiple-Turnover is Limited by Product Release

Figure 13A:
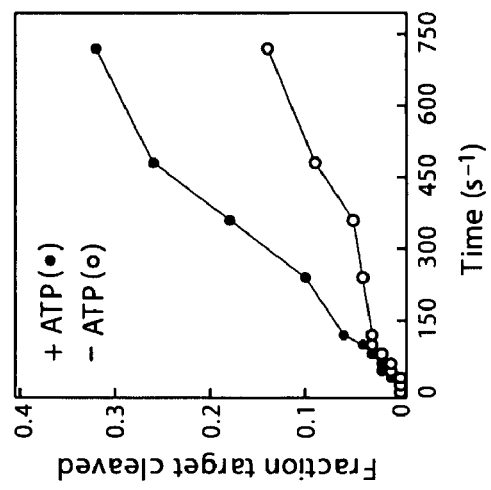
FIG. 13. Product release limits the rate of catalysis by RISC. (a) ATP stimulates multiple rounds of RISC cleavage of the RNA target. siRNA was incubated with ATP in *Drosophila* embryo lysate, then NEM was added to quench RISC assembly and to disable the ATP-regenerating system. The energy regenerating system was either restored by adding additional creatine kinase (+ATP) or the reaction was ATP-depleted by adding hexokinase and glucose (–ATP). The target RNA concentration was 49 nM and the concentration of RISC was ~4 nM. The siRNA sequence and its target RNA is given in FIG. 21A. (b) In the absence of ATP, cleavage by RISC produces a pre-steady state burst equal, within error, to the concentration of active RISC. The target concentration was 110 nM and the RISC concentration was ~4 nM. (c) Catalysis by RISC is not enhanced by ATP under single-turnover conditions. RISC was present in ~8-fold excess over target. Each data point represents the average of two trials.
Figure 13B:
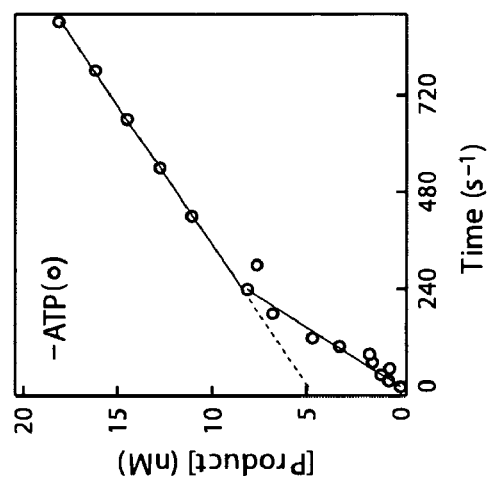

The evaluation of the kinetics of siRNA-directed target cleavage in the presence or absence of ATP was further performed (FIG. 13). RISC was assembled in the presence of ATP, then the energy regenerating enzyme, creatine kinase, was inactivated with NEM, and ATP depleted by adding hexokinase and glucose (−ATP conditions). For +ATP measurements creatine kinase was added to the reaction after NEM-treatment, and the hexokinase treatment was omitted. A faster rate of cleavage in the presence than in the absence of ATP was observed. This difference was only apparent late in the reaction time course, indiciating that the ATP-dependent rate of cleavage was faster than the ATP-independent rate only at steady state (FIG. 13A). The analysis was repeated in more detail (FIG. 13B). In the absence of ATP, a burst of cleaved product early in the reaction, followed by a ~4-fold slower rate of target cleavage was observed. No burst was observed in the presence of ATP (FIG. 13A). If the burst corresponds to a single-turnover of enzyme, then extrapolation of the slower steady state rate back to the y-axis should give the amount of active enzyme in the reaction. The y-intercept at the start of the reaction for the steady-state rate was 4.9 nM, in good agreement with the amount of RISC estimated using the tethered 2'-O-methyl oligonucleotide assay (~4 nM; FIG. 13 B).

Figure 13C:
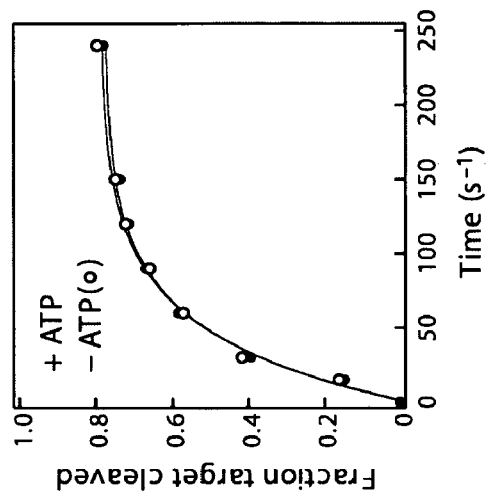

In principle, ATP could enhance target recognition by RISC, promote a rearrangement of the RISC/target complex to an active form, facilitate cleavage itself, promote the release of the cleavage products from the siRNA guide strand, or help restore RISC to a catalytically competent state after product release. All of these steps, except product release and restoration to catalytic competence, should affect the rate of both multiple and single-turnover reactions. Therefore, the rate of reaction in the presence and in the absence of ATP under conditions in which RISC was in excess over the RNA target was analyzed. At early times under these conditions, the reaction rate should reflect only single-turnover cleavage events, in which events after cleavage do not determine the rate of reaction. Using single-turnover reaction conditions, identical rates of RISC-mediated cleavage in the presence or absence of ATP was observed (FIG. 13C). Thus, ATP must enhance a step that occurs only when each RISC catalyzes multiple cycles of target cleavage.

If product release is rate-determining for multiple-turnover catalysis by RISC in the absence, but not the presence, of ATP, then modifications that weaken the strength of pairing to the target RNA might enhance product release, but would not be expected to accelerate the return of the RISC to a catalytically competent state. Mismatches between the siRNA and its RNA target at the 3' end of the siRNA guide strand was incorporated and designed the siRNAs to be functionally asymmetric, ensuring efficient and predictable incorporation of the let-7 strand into RISC (FIG. 14A). The reaction velocity under conditions of substrate excess in the presence and in the absence of ATP for siRNAs with zero to four mismatches between the guide strand 3' end and the RNA target were compared. Cleavage was measured from 100 and 540 s, when >90% of the target remained uncleaved, ensuring that the multiple-turnover reaction was at steady state. Even a single 3' mismatch between the siRNA and its target increased the −ATP rate, relative to the +ATP rate, and siRNAs with two or more mismatches showed no significant difference in rate between the presence and absence of ATP (FIG. 14B). The results indicated that in the absence of ATP, product release is the rate-determining step for siRNAs fully matched to their RNA targets.

Example IX siRNA:Target Complementarity and RISC Function

Figure 14C:
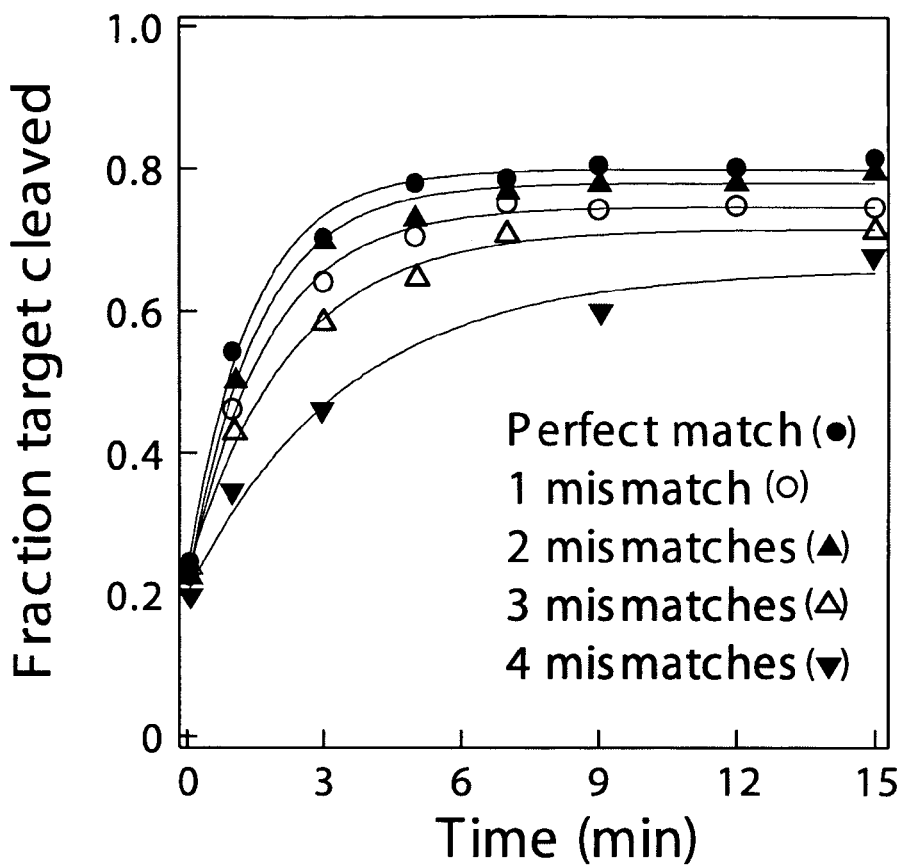
FIG. 14. In the absence of ATP, mismatches between the 3' end of the siRNA guide strand and the target RNA facilitate product release, but reduce the rate of target cleavage. (a) Representative siRNA sequences are shown aligned with the target sequence (SEQ ID NOS 92-101). The siRNA guide strand is in color (5' to 3') and the mismatch with the target site is highlighted in yellow. A complete list of siRNA sequences appears in FIG. 21. (b) The steady-state rate of cleavage in the presence and absence of ATP was determined for siRNAs with zero to four 3' mismatches with the target site. The target RNA concentration was 49 nM and the concentration of RISC was either ~4 nM (no mismatches) or ~6 nM (1 to 4 mismatches). The steady-state velocity with ATP, relative to the velocity without ATP is shown for each siRNA. (c) Time course of cleavage for perfectly matched (~16-fold excess of RISC relative to target) and mismatched (~80-fold excess of RISC) siRNA. (d) Data representative of those used in the analysis in (c) for target cleavage directed by siRNAs with zero, four, and five 3' mismatches.
Figure 14D:
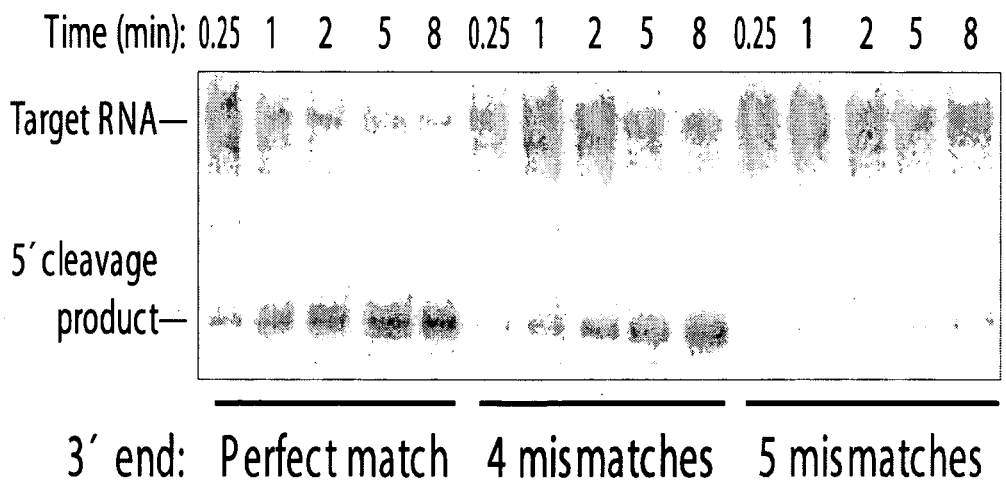

Mismatches between the siRNA and its target facilitate product release, but not without cost: the rate of reaction, irrespective of ATP concentration, decreases with each additional 3' mismatch. When the concentration of RISC was ~16-80-fold greater than the target RNA concentration, each additional mismatch between the 3' end of the siRNA guide strand and the RNA target further slowed the reaction (FIG. 14C,D). Under conditions of substrate excess, the effect of mismatches between the 3' end of the siRNA guide strand and its RNA target was more striking (FIG. 15A): the rate of cleavage slowed ~20% for each additional mismatch. To test the limits of the tolerance of RISC for 3' mismatches, cleavage under modest (8-fold, FIG. 15B) and vast (~80-fold, FIGS. 15C and 16C) enzyme excess over target RNA was analyzed. Remarkably, cleavage was detected for siRNAs with as many as nine 3' mismatches to the RNA target (FIGS. 15C and 16C), but only after 24 hour incubation. No cleavage was detected for an siRNA with ten 3' mismatches to the RNA target (FIG. 15C).

Figure 16A:
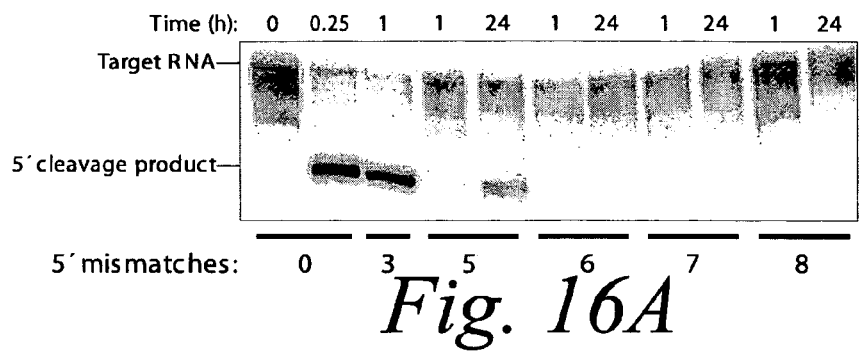
FIG. 16. Limited tolerance of RISC for 5' mismatches. (a) RISC cleavage was analyzed as in FIG. 21C using 5' mismatched siRNAs, whose sequences are given in FIG. 21. The target RNA was the same for all siRNAs. siRNA sequences and the corresponding target RNA sequence are shown in FIG. 21E. (b) RISC cleavage was analyzed using a single siRNA sequence. Mismatches were created by altering the sequence of the target RNA. For the target containing compensatory mutations, the target concentration was 0.25 nM and the siRNA concentration was ~20 nM; RISC concentration was not determined. The asterisk denotes a 15 second time-point. siRNA sequences and corresponding target RNA sequence are shown in FIG. 21F. (c) RISC cleavage was analyzed by incubating 50 nM siRNA with 0.5 nM target RNA. 3' mismatches were created by modifying the target sequence, and 5' mismatches by changing the siRNA. Target and siRNA sequences are given in FIG. 21C. (d) Perfectly base-paired and 5' mismatched siRNAs direct cleavage at the same phosphodiester bond. Cleavage reactions were performed with ~20 nM RISC generated from 50 nM siRNA and 0.5 nM target RNA and analyzed on an 8% denaturing polyacrylamide sequencing gel. The target mRNA was 182 nt and 5' cleavage product was 148 nt. After RISC was assembled, the extract was treated with NEM to inactivate nucleases (Schwartz et al., 2004). After NEM treatment, the ATP regenerating system was restored by adding additional creatine kinase, then target RNA was added and the incubation continued for the indicated time. OH— denotes a base hydrolysis ladder. The siRNA and corresponding target RNA sequences used in this experiment are shown in FIG. 21E.
Figure 16B:
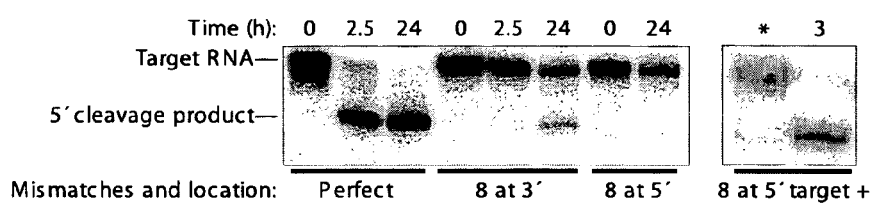

Linsley and colleagues have proposed siRNA-directed down-regulation of an mRNA with as few as eleven contiguous bases complementary to the siRNA guide strand (Jackson et al., 2003). In that study, the mRNA target paired with both nts 2-5 and nts 7-17 of the siRNA guide strand, but mismatched at nts 1 and 6 of the siRNA. Results indicated that up to five mismatched bases are tolerated between the 5' end of the siRNA and its RNA target (FIG. 16A,B). No cleavage was detected for siRNAs with six, seven, or eight 5' mismatches to the target, even after 24 hour incubation. The siRNA bearing eight mismatches between its 5' end and the let-7 complementary target was fully active when eight compensatory mutations were introduced into the let-7 binding site (FIGS. 15C and 16B), demonstrating that mutation of the siRNA was not the cause for its inactivity against the mismatched target. Similarly, when eight mismatches with the 3' or 5' end of the siRNA were created by changing the sequence of the RNA target, target RNA cleavage when the target contained eight mismatches with the siRNA 3' end, but not with the 5' end was detected (FIG. 16B,C).

Figure 16C:
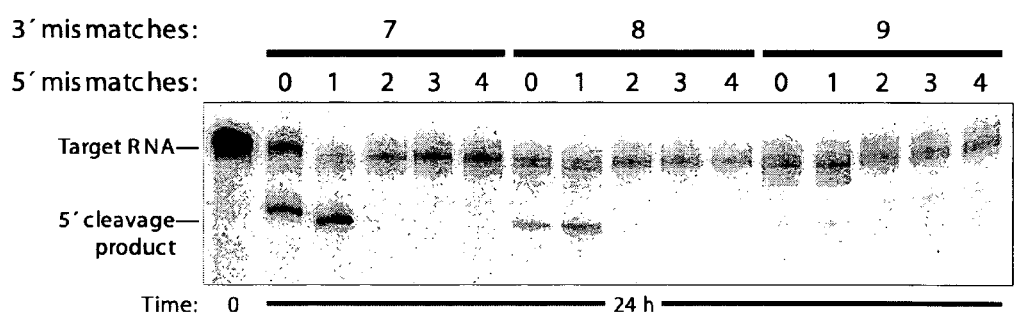

To begin to estimate the minimal number of base pairs between the siRNA and its target that permit detectable cleavage by RISC at 24 hour incubation, seven, eight, or nine 3' mismatches with increasing numbers of 5' mismatches were combined (FIG. 16C). Cleavage was detected for as many as nine 3' mismatches. However, no detectable cleavage occurred when seven, eight, or nine 3' mismatches were combined with two or more 5' mismatches. In contrast, a single 5' mismatch (p1) enhanced target cleavage directed by all three 3' mismatched siRNAs. Only 6% of the target RNA was cleaved after 24 hours when the siRNA contained nine contiguous 3' mismatches with the target RNA, but 10% was cleaved when the siRNA contained both nine 3' mismatches and a single (p1) 5' mismatch. Cleavage was similarly enhanced by the addition of a p1 mismatch to seven 3' mismatches (49% cleavage versus 75% cleavage at 24 hours) or to eight 3' mismatches (21% versus 42% cleavage at 24 hours). The finding that unpairing of the first base of the siRNA guide strand potentiated cleavage under single-turnover conditions inducated that a conformational change occurs in RISC during which the paired p1 base becomes unpaired prior to cleavage. Intriguingly, p1 is often predicted to be unpaired for miRNAs bound to their targets (Lewis et al., 2003; Rhoades et al., 2002; Stark et al., 2003).

Figure 16D:
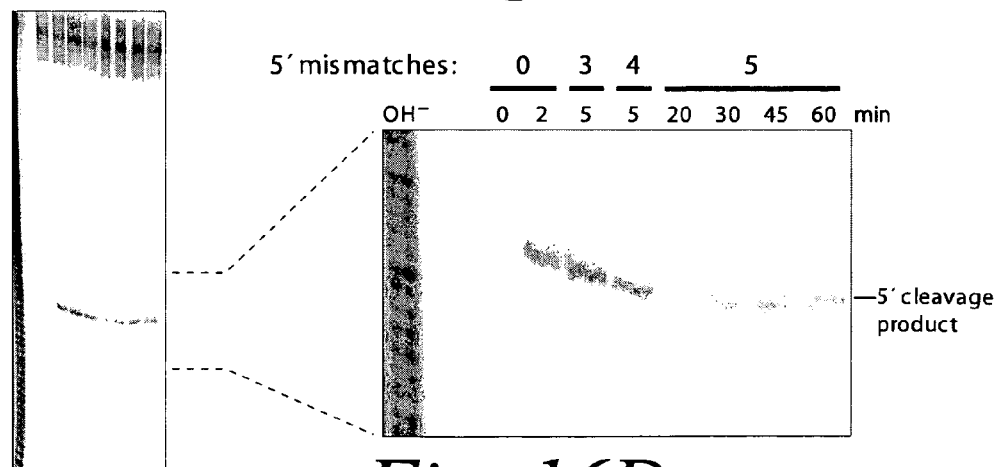

For siRNAs that pair fully with their RNA targets, the scissile phosphate always lies between the target nucleotides that pair with siRNA bases 10 and 11 (Elbashir et al., 2001; Elbashir et al., 2001). Analysis at single nucleotide resolution of the 5' cleavage products generated by siRNAs with three, four, or five 5' mismatches (FIG. 16D) or six 3' terminal mismatches (data not shown) revealed that the scissile phosphate on the target RNA remained the same, even when five 5' nts of the siRNA guide strand were mismatched with the target RNA (FIG. 16D). As discussed below, this result indicates that the identity of the scissile phosphate is a consequence of the structure of RISC, rather than being measured from the 5' end of the helix formed between the siRNA and its RNA target.

Example X

Kinetic Analysis of RISC Catalysis

Figures 17A, 17B:
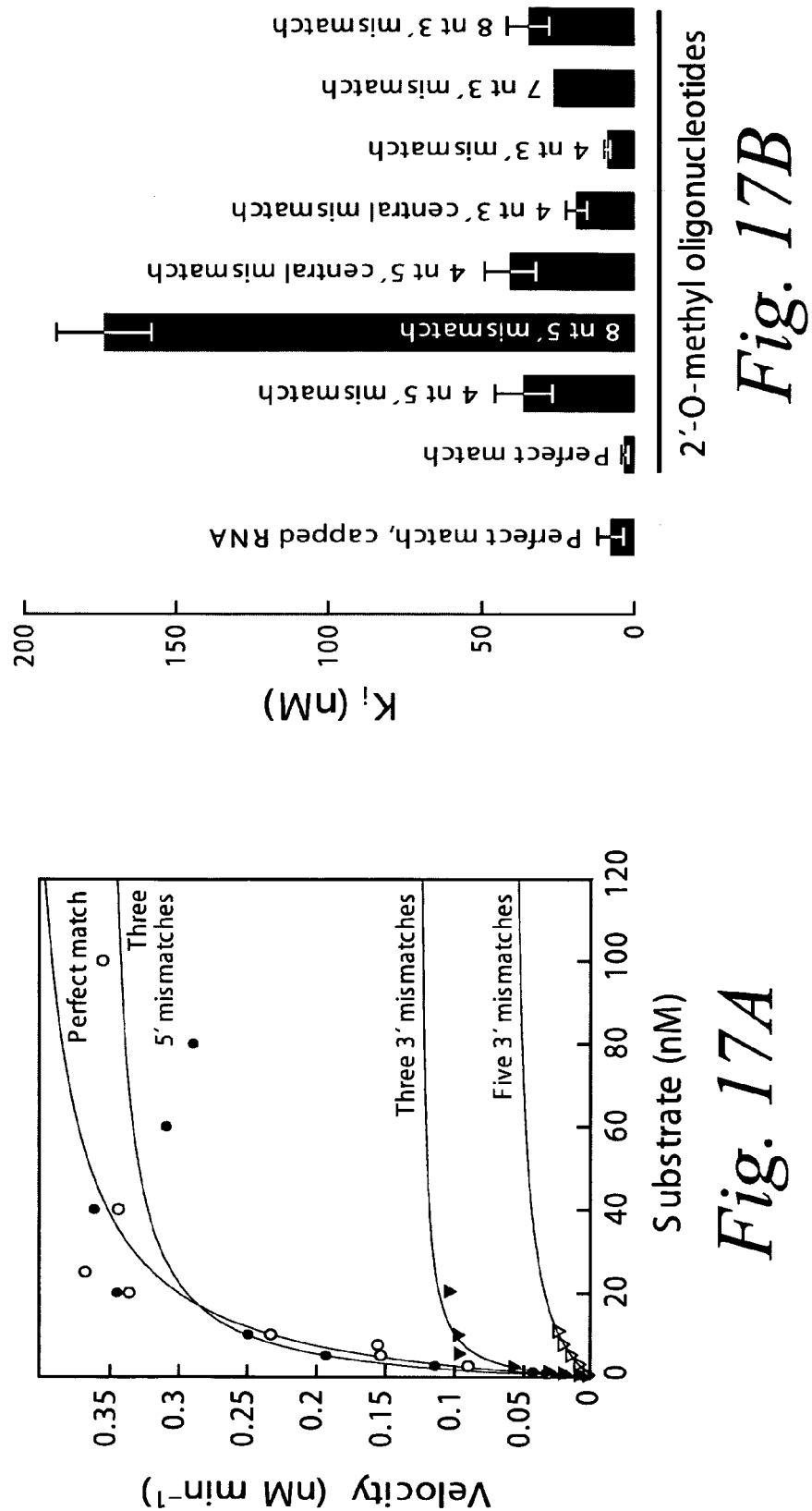
FIG. 17. Michaelis-Menten and Ki analysis for matched and mismatched siRNAs reveal distinct contributions to binding and catalysis for the 5', central, and 3' regions of the siRNA. (a) siRNA was assembled into RISC under standard in vitro RNAi conditions, then diluted to achieve the desired RISC concentration. The initial rates of cleavage were determined for increasing concentrations of 5' 32P-cap-radiolabled target mRNA. Plot of initial velocity versus substrate concentration. KM and Vmax were determined by fitting the data to the Michaelis-Menten equation. See Table 1 for analysis. Representative initial rate determinations appear in FIG. 20A, and the siRNA sequences used in this experiment are shown in FIGS. 21A and 21E. (b) Ki values were determined in competition assays using 2'-O-methyl oligonucleotides bearing 5', central, and 3' mismatches to the siRNA guide strand. Representative data are presented in FIG. 20B, and a complete list of the 2'-O-methyl oligonucleotides used appears in FIG. 21D.

The role of nucleotides in the terminal regions of the siRNA guide strand in directing RISC activity was next studied. Reduced pairing between an siRNA and its target might disrupt the binding of RISC to its target. Alternatively, mismatches might disrupt the structure, but not the affinity, of the siRNA/target interaction. Fully matched siRNAs are thought to form a 21 base-pair, A-form helix with the target RNA (Chiu et al., 2003; Shiu et al., 2002), but do all parts of this helix contribute equally to target binding or do some regions provide only a catalytically permissive geometry? To distinguish between these possibilities, the Michaelis-Menten kinetics of siRNA-directed target-RNA cleavage for a perfectly matched siRNA and for three siRNAs mismatched at their termini was analyzed. siRNAs were assembled into RISC, then diluted with reaction buffer to the desired RISC concentration and mixed with target RNA. For each siRNA, the initial velocity of reaction was determined at multiple substrate concentrations (FIG. 21A), and KM and kcat determined from a non-linear least squares fit of substrate concentration versus initial velocity (FIG. 17A). By this assay, the KM of the let-7 siRNA with complete complementarity to its target was ~8.4 nM was estimated (Table 1). A significant difference in KM, within error, between the fully paired siRNA and siRNA variants bearing three to five mismatches at their 3' end or three mismatches at their 5' end was not detected (FIG. 17A and Table 1). For the mismatched siRNAs a higher than optimal enzyme concentration in order to detect cleavage was used. Therefore, the KM measurements for the mismatched siRNAs represent an upper bound for the actual KM values.

While the KM was unaltered for the let-7 siRNA containing several terminal mismatches, the turnover number, kcat, was decreased by terminal mismatches (Table 1). Three mismatches at either the 3' or the 5' end of the siRNA halved the kcat. The introduction of five, 3' mismatches also had no significant effect on KM, yet decreased kcat nearly 17-fold (Table 1).

Table 1 Summarizes the kinetic data from the analysis in FIG. 17A. For comparison, the KM and kcat values of four well studied protein enzymes are provided. KM and kcat±error of fit are reported.

Example XI

KM Reflects the Binding Strength of RISC

To estimate the contribution of binding to KM, a competition assay that measures the ability of 2'-O-methyl oligonucleotides to inhibit target cleavage by RISC was used (FIG. 17B,C). Such a strategy was used previously to analyze the mechanism of target destruction by antisense oligonucleotides that recruit RNase H (Lima et al., 1997). The anticipation was that 2'-O-methyl oligonucleotides would act as competitive inhibitors of RISC, because they bind to RISC containing complementary siRNA but not to RISC containing unrelated siRNA (Hutvàgner et al., 2004; Meister et al., 2004). Thirty-one nt long, 2'-O-methyl oligonucleotides were designed as described previously (Hutvàgner et al., 2004), taking care to exclude sequences predicted to form stable internal structures. 2'-O-methyl oligonucleotides were chosen because of their marked stability in *Drosophila* lysate and because they can be added to the reaction at high μM concentration.

Competition by 2'-O-methyl oligonucleotides and bona fide RNA targets was quantitatively similar. The reaction velocities of siRNA-directed cleavage of a 32P-radiolabeled target in the presence of increasing concentrations of unlabeled capped RNA target or a 31-nt 2'-O-methyl oligonucleotide corresponding to the region of the target containing the siRNA binding site was analyzed (FIG. 17B). Lineweaver-Burk analysis of the data confirm that 2'-O-methyl oligonucleotides act as competitive inhibitors of RISC (data not shown). These data were used to calculate Ki values for the perfectly matched RNA and 2′-O-methyl competitors. For the capped RNA competitor, the Ki was ~7.7±4 nM (FIG. 17B), nearly identical to the KM for this siRNA, 8.4 nM (Table 1). The Ki for the perfectly matched 2′-O-methyl competitor oligonucleotide was 3.2±1 nM (FIG. 17B), essentially the same, within error, as that of the all-RNA competitor. The results indicated that 2′-O-methyl oligonucleotides are good models for 5′-capped RNA targets and that the KM for target cleavage by RISC is largely determined by the affinity (KD) of RISC for its target RNA.

Although targets with more than five contiguous mismatches to either end of the siRNA are poor substrates for cleavage, they might nonetheless bind RISC and compete with the 32P-radiolabeled target RNA. The 2′-O-methyl oligonucleotide competition assay to determine the Ki values for oligonucleotides containing as many as eight mismatches to the siRNA guide strand was used (FIG. 17B). 2′-O-methyl oligonucleotides with 3′ terminal mismatches to the siRNA were good competitors: a four nucleotide mismatch with the 3′ end of the siRNA increased the Ki by only ~3-fold (9.0±0.9 nM) and an eight nucleotide mismatch with the 3′ end of the siRNA increased the Ki by ~10-fold (34.8±7 nM). In contrast, mismatches with the 5′ end of the siRNA had a dramatic effect on binding. A four nucleotide mismatch to the 5′ end of the siRNA increased the Ki ~12-fold (36.4±9.2 nM) and an eight nucleotide mismatch to the 5′ end of the siRNA increased the Ki 53-fold (173±16 nM). The differential effect on binding between 5′ and 3′ mismatches was maintained even at the center of the siRNA: a 2′-O-methyl oligonucleotide bearing four mismatches with siRNA nucleotides 11, 12, 13, and 14 (4 nt 3′ central mismatch, FIG. 17B) bound more tightly to RISC (i.e., had a lower Ki) than an oligonucleotide with four mismatches to siRNA positions 7, 8, 9, and 10 (4 nt 5′ central mismatch, FIG. 17B).

Discussion of Examples VII-XI

RISC programmed with exogenous siRNA is an enzyme, capable of multiple rounds of target cleavage. Prevoius studies showed that cleavage of a target RNA by RISC does not require ATP (Nykänen et al., 2001; Tomari et al., 2004). The more detailed kinetic analysis presented herein indicates that there are no ATP-assisted steps in either target recognition or cleavage by *Drosophila* RISC; no difference in rate in the presence or absence of ATP for RNAi reactions analyzed under conditions of substrate excess at early time points (pre-steady state) or under conditions of enzyme excess where the reaction was essentially single-turnover was detected. In contrast, the steady-state rate of cleavage under multiple turnover conditions was enhanced four-fold by ATP. The results indicates that release of the products of the RISC endonuclease is rate determining under these conditions in the absence of ATP, but not in the presence of ATP. The most straightforward explanation for this finding is that an ATP-dependent RNA helicase facilitates the dissociation of the products of target cleavage from the RISC-bound siRNA. The involvement of such an ATP-dependent helicase in RNAi in vivo may explain why siRNAs can be active within a broad range of GC content (Reynolds et al., 2004).

In the presence of ATP, siRNA-programmed *Drosophila* RISC is a classical Michaelis-Menten enzyme. The guide strand of the siRNA studied here has the sequence of let-7, an endogenous miRNA. In vivo, let-7 is not thought to direct mRNA cleavage, but rather is believed to repress productive translation of its mRNA targets. Nonetheless, the let-7 siRNA is among the most potent of the siRNAs we have studied in vitro and provides a good model for effective siRNA in general. With a kcat of ~7×10−3 s−1, the let-7 siRNA-programmed RISC was slow compared to enzymes with small molecule substrates (Table 1). The KM for this RISC was ~8 nM. Enzymes typically have KM values between 1- and 100-fold greater than the physiological concentrations of their substrates (Stryer et al., 1981). The results indicate that RISC is no exception: individual abundant mRNA species are present in eukaryotic cells at high pM or low nM concentration. The KM of RISC is likely determined primarily by the strength of its interaction with the target RNA, because the KM is nearly identical to the Ki of a non-cleavable 2′-O-methyl oligonucleotide inhibitor.

Recently, a study of the kinetic parameters of target RNA cleavage by human RISC was described (Martinez et al., 2004). In that study, the minimal active human RISC was highly purified; in this study, *Drosophila* RISC activity was measured for the unpurified, intact holo-RISC, believed to be an 80S multi-protein complex (Pham et al., 2004). Different siRNAs were used in the two studies. Nonetheless, the KM and kcat values reported here and for the minimal human RISC are remarkably similar: the KM was 2.7-8.4 nM and the kcat was 7.1×10−3 sec−1 for the let-7 siRNA-programmed *Drosophila* holo-RISC versus a KM of 1.1-2.3 nM and a kcat of 1.7×10−2 sec−1 for a different siRNA in minimal human RISC. As in this study, a pre-steady-state burst was observed in the absence of ATP, consistent with the idea that product release is ATP-assisted in vivo.

The ratio of kcat to KM is a classical measure of enzyme efficiency and corresponds to the second order rate constant for the reaction when the concentration of substrate is much less than the KM. For the let-7 programmed RISC, kcat KM−1 equals ~8.4×105 M−1−1 (~8.4×10−4 nM−1 s−1), a value far slower than the expected rate of collision of RISC−1 with mRNA, =107 M−1 s. It is possible that the rate of catalysis by RISC is constrained by the rate of conformational changes required for formation of the enzyme-substrate complex or by subsequent conformational rearrangements required for catalysis. It is possible that siRNAs can be designed that significantly improve either the kcat or KM of RISC without compromising specificity.

Figure 18:
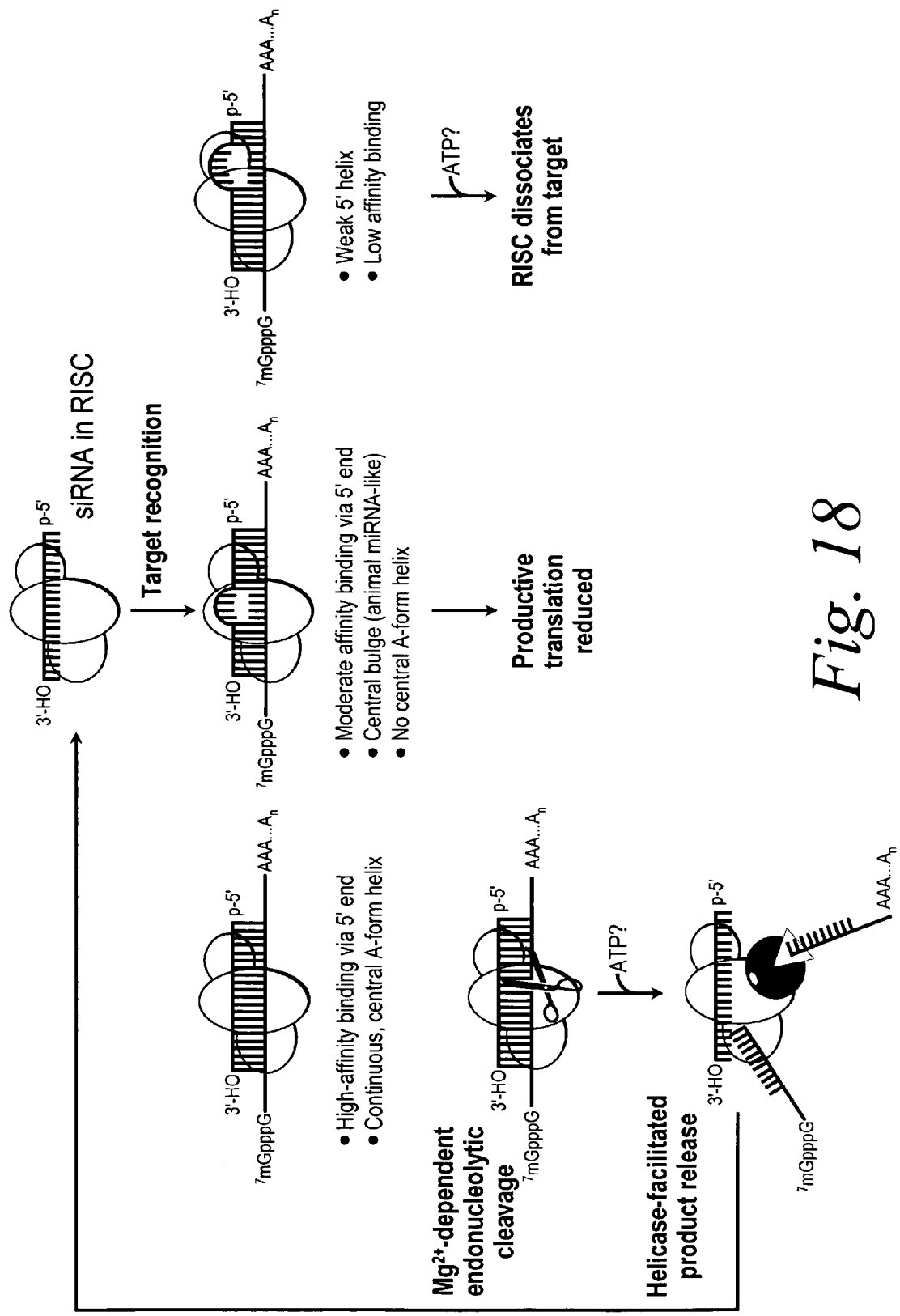
FIG. 18. A model for the cycle of RISC assembly, target recognition, catalysis, and recycling.
Figure 20A:
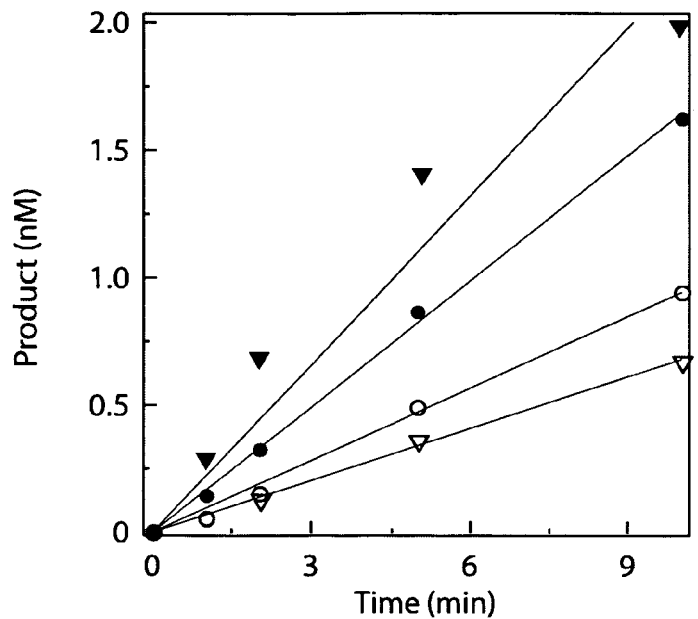
FIG. 20. Michaelis-Menton and Competitor Analysis of RISC (a) Representative data for the determination of initial velocities for the perfectly matched siRNA. Black, 1 nM target; red, 5 nM; blue, 20 nM; and green, 60 nM. (b) Three independent experiments for inhibition by a fully complementary 2'-O-methyl oligonucleotide competitor. ~1 nM RISC and 5 nM 32P-cap-radiolabeled target mRNA were incubated with increasing concentration of competitor, and the initial velocities were calculated and plotted versus competitor concentration.
Figure 20B:
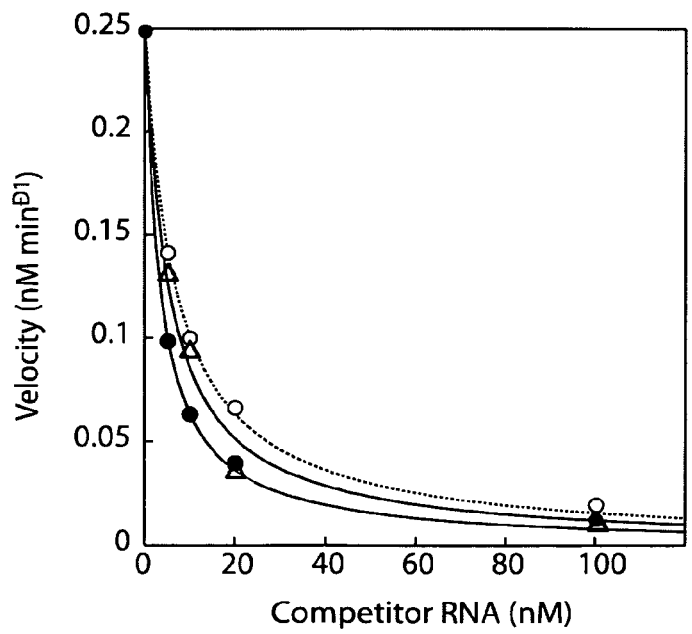

Although siRNAs are typically envisioned to bind their target RNAs through 19 to 21 complementary base pairs, we find that the 5′, central, and 3′ regions of the siRNA make distinct contributions to binding and catalysis (FIG. 18). Measurements of KM and Ki suggest that the 5′ nucleotides of the siRNA contribute more to target binding than do the 3′ nucleotides. At least for the siRNA examined here, the first three and the last five nucleotides of a 21 nt siRNA contribute little to binding. If the KD of RISC bound to its target RNA is essentially its KM, ~8 nM, then the free energy (.G°=−RT lin KD) of the let-7-programmed RISC:target interaction is approximately −11 kcal mol−1, considerably less than the −35 kcal mol−1 (KD~10-29) predicted 32 for the let-7 RNA bound to a fully complementary RNA in 100 mM K+ and 1.2 mM Mg2+ at 25° C. It is possible that RISC discards potential binding energy by binding less tightly to its target, an siRNA in RISC gains the ability to discriminate between well matched and poorly match targets, but only for bases in the 5′ region of the siRNA guide strand.

Mismatches between the central and 3′ regions of an siRNA and its target RNA reduce kcat far more than mismatches at the 5′ end of the siRNA. These results fit well with recent findings by Doench and Sharp that translational repression by siRNA, designed to act like animal miRNA, is dramatically disrupted by mismatches with the 5′ end of the siRNA, but not with similar mismatches at the 3' end 18. These authors propose that miRNA binding is mediated primarily by nucleotides at the 5' end of the small RNA. In fact, complementarity between the 5' end of miRNAs and their targets has been required by all computational approaches for predicting animal miRNA targets (Rajewsky et al., 2004; Lewis et al., 2003; Stark et al., 2003; Enright et al., 2003). The instant discovery that central and 3' siRNA sequences must pair with the target sequence for effective target cleavage but not for target binding reinforces this view; both central and 3' miRNA sequences are usually mismatched with their binding sites in their natural targets (Lee et al., 1993; Reinhart et al., 2000; Brennecke et al., 2003; Abrahante et al., 2003; Vella et al., 2004; Xu et al., 2003; Johnston et al., 2003).

Formation of a contiguous A-form helix surrounding the scissile phosphate of the target mRNA has been proposed to be a quality control step for RISC-mediated target cleavage (Chiu et al., 2003). The instant invention discovers that RISC can direct cleavage when the siRNA is paired with the target RNA only at nts 2-12 of the guide strand, corresponding to one complete turn of an RNA:RNA helix. This region of the siRNA includes nts 2-8, which appear to be critical for miRNA recognition of mRNAs targeted for translational repression, plus two nts flanking either side of the scissile phosphate. The instant invention further discovers unpairing the first nt of the guide strand enhances the activity of siRNAs with seven, eight or nine 3' mismatches to the RNA target is striking, since many miRNAs do not pair with their targets at this position. Furthermore, such pairing resembles that reported by Linsley and colleagues for siRNA-directed off-target effects in cultured mammalian cells (Jackson et al., 2003).

The requirement for a full turn of a helix may reflect a mechanism of 'quality control' by RISC. Since RISC can apparently assemble on any siRNA sequence, it must use the structure of the siRNA paired to its target to determine whether or not to cleave. Despite the apparent surveillance of the structure of the siRNA/target pair, the identity of the scissile phosphate is unaltered by extensive mismatch between the 5' end of the siRNA and its target. Yet the scissile phosphate is determined by its distance from the 5' end of the siRNA guide strand (Elbashir et al., 2001; Elbashir et al., 2001). The simplest explanation for the instant discovery is that the scissile phosphate is identified by a protein loaded onto the siRNA during RISC assembly, i.e., before the encounter of the RISC with its target RNA.

The remarkable tolerance of RISC for mismatches between the siRNA and its targets—up to nine contiguous 3' nucleotides—implies that a large number off-target genes should be expected for many siRNA sequences when RISC is present in excess over its RNA targets. However, RISC with extensive mismatches between the siRNA and target are quite slow to cleave, so off-target effects may be minimized by keeping the amount of RISC as low as possible. These understandings of the molecular basis of siRNA-directed gene silencing assist the skilled artisan in creating siRNAs designed to balance the competing demands of siRNA efficacy and specificity.

Experimental Procedures

A. General Methods

*Drosophila* embryo lysate preparation, in vitro RNAi reactions, and cap-labeling of target RNAs using Guanylyl transferase were carried out as previously described (Tuschl et al., 1999; Zamore et al., 2000). Target RNAs were used at ~5 nM concentration to ensure that reactions occurred under single-turnover conditions. Target cleavage under these conditions was proportionate to siRNA concentrations. Cleavage products of RNAi reactions were analyzed by electrophoresis on 5% or 8% denaturing acrylamide gels. 5' end labeling and determination of siRNA unwinding status were according to Nykänen et al. (Nykänen et al., 2001) except that unlabeled competitor RNA was used at 100-fold molar excess. Gels were dried, then exposed to image plates (Fuji), which were scanned with a Fuji FLA-5000 phosphorimager. Images were analyzed using Image Reader FLA-5000 version 1.0 (Fuji) and Image Gauge version 3.45 or 4.1 (Fuji). Data analysis was performed using Excel (Microsoft) and Igor Pro 5.0 (Wavemetrics).

B. *Drosophila* embryo lysate, siRNA labeling with polynucleotide kinase (New England Biolabs), target RNA preparation and labeling with guanylyl transferase were carried out as described (Hutvàgner et al., 2002, Haley et al., 2003) and the forward primer sequence for 379 nt target mRNA was 5'-CGC TAA TAC GAC TCA CTA TAG CAG TTG GCG CCG CGA ACG A-3' (SEQ ID NO: 144), and 5'-GCG TAA TAC GAC TCA CTA TAG TCA CAT CTC ATC TAC CTC C-3 (SEQ ID NO: 145) for the 182 nt target. Reverse primers used to generate fully matched and mismatched target RNAs were: 5'-CCC ATT TAG GTG ACA CTA TAG ATT TAC ATC GCG TTG AGT GTA GAA CGG TTG TAT AAA AGG TTG AGG TAG TAG GTT GTA TAG TGA AGA GAG GAG TTC ATG ATC AGT G-3' (SEQ ID NO: 146) (perfect match to let-7); 5'-CCC ATT TAG GTG ACA CTA TAG ATT TAC ATC GCG TTG AGT GTA GAA CGG TTG TAT AAA AGG TTG AGG TAG TAG GTT CAT GCA GGA AGA GAG GAG TTC ATG ATC AGT G-3' (SEQ ID NO: 147) (7 nt 3' mismatch); 5'-CCC ATT TAG GTG ACA CTA TAG ATT TAC ATC GCG TTG AGT GTA GAA CGG TTG TAT AAA AGG TTG AGG TAG TAG GTA CAU GCA GGA AGA GAG GAG TTC ATG ATC AGT G-3' (SEQ ID NO: 148) (8 nt 3' mismatch); 5'-CCC ATT TAG GTG ACA CTA TAG ATT TAC ATC GCG TTG AGT GTA GAA CGG TTG TAT AAA AGG TTG AGG TAG TAG GAA CAT GCA GGA AGA GAG GAG TTC ATG ATC AGT G-3' (SEQ ID NO: 149) (9 nt 3' mismatch); 5'-CCC ATT TAG GTG ACA CTA TAG ATT TAC ATC GCG TTG AGT GTA GAA CGG TTG TAT AAA AGG TAC TCC ATC TAG GTT GTA TAG TGA AGA GAG GAG TTC ATG ATC AGT G-3' (SEQ ID NO: 150) (8 nt 5' mismatch); 5'-CCC ATT TAG GTG ACA CTA TAG ATT TAC ATC GCG TTG AGT GTA GAA CGG TTG TAT AAA AGG TAC TCG TAG TAG GTT GTA TAG TGA AGA GAG GAG TTC ATG ATC AGT G-3' (SEQ ID NO: 151) (4 nt 5'mismatch). In FIGS. 13, 14, 15, 17A, 19 and 20A, the target sequence was 613 nt long; 379 nt in FIGS. 16A-C, 17B and 20B; and 182 nt in FIG. 16D. All siRNAs were deprotected according to the manufacturer's protocol (Dharmacon), 5'-radiolabeled where appropriate, then gel purified on a 15% denaturing polyacrylamide gel. 2'-O-methyl oligonucleotides were from Dhammacon. siRNA strands were annealed at high concentrations and serially diluted into lysis buffer (30 nM HEPES pH 7.4, 100 mM KOAc, and 2 mM MgCl2). Gels were dried and imaged as described (Schwartz et al., 2003). Images were analyzed using Image Gauge 4.1 (Fuji). Initial rates were determined by linear regression using Excel X (Microsoft) or Igor Pro 5.01 (Wavemetrics). Kaleidagraph 3.6.2 (Synergy Software) was used to determine KM and Ki by global fitting to the equations: $V=(Vmax \times S)(KM+S)-1$ and $V=(Vmax \times Ki(app))(Ki(app)+I)-1$, where V is velocity, S is target RNA concentration, and I is the concentration of 2'-O-methyl oligonucleotide competitor. Ki was calculated by correcting Ki(app) by the KM and substrate concentration, $Ki=Ki(app)(1+(S\ KM-1))-1$.

C. siRNA Preparation

Synthetic RNAs (Dharmacon) were deprotected according to the manufacturer's protocol. siRNA strands were annealed (Elbashir et al., 2001a) and used at 50 nM final concentration unless otherwise noted. siRNA single strands were phosphorylated with polynucleotide kinase (New England Biolabs) and 1 mM ATP according to the manufacturer's directions and used at 500 nM final concentration.

D. Target RNA Preparation

Target RNAs were transcribed with recombinant, histidine-tagged, T7 RNA Polymerase from PCR products as described (Nykänen et al., 2001; Hutvágner and Zamore, 2002), except for sense sod1 mRNA, which was transcribed from a plasmid template (Crow et al., 1997) linearized with Bam HI. PCR templates for htt sense and anti-sense and sod1 anti-sense target RNAs were generated by amplifying 0.1 ng/ml (final concentration) plasmid template encoding htt or sod1 cDNA using the following primer pairs: htt sense target, 5'-GCG TAA TAC GAC TCA CTA TAG GAA CAG TAT GTC TCA GAC ATC-3' (SEQ ID NO: 152) and 5'-UUCG AAG UAU UCC GCG UAC GU-3' (SEQ ID NO: 153); htt anti-sense target, 5'-GCG TAA TAC GAC TCA CTA TAG GAC AAG CCT AAT TAG TGATGC-3' (SEQ ID NO: 154) and 5'-GAA CAG TAT GTC TCA GAC ATC-3' (SEQ ID NO: 155); sod1 anti-sense target, 5'-GCG TAA TAC GAC TCA CTA TAG GGC TTT GTT AGC AGC CGG AT-3' (SEQ ID NO: 156) and 5'-GGG AGA CCA CAA CGG TTT CCC-3' (SEQ ID NO: 157).

Immobilized 2'-O-Methyl Oligonucleotide Capture of RISC

The 5' end of the siRNA strand to be measured was 32P-radiolabeled with PNK. 10 pmol biotinylated 2'-O-Methyl RNA was immobilized on Dynabeads M280 (Dynal) by incubation in 10 ml lysis buffer containing 2 mM DTT for 1 h on ice with the equivalent of 50 ml of the suspension of beads provided by the manufacturer. The beads were then washed to remove unbound oligonucleotide. 50 nM siRNA was pre-incubated in a standard 50 ml in vitro RNAi reaction for 15 min at 25° C. Then, all of the immobilized 2'-O-Methyl oligonucleotide was added to the reaction and the incubation continued for 1 h at 25° C. After incubation, the beads were rapidly washed three times with lysis buffer containing 0.1% (w/v) NP-40 and 2 mM DTT followed by a wash with the same buffer without NP-40. Input and bound radioactivity were determined by scintillation counting (Beckman). The 5'-biotin moiety was linked via a six-carbon spacer arm. 2'-O-methyl oligonucleotides (IDT) were: 5'-biotin-ACA UUU CGA AGU AUU CCG CGU ACG UGA UGU U-3' (SEQ ID NO: 158) (to capture the siRNA sense strand) 5'-biotin-CAU CAC GUA CGC GGA AUA CUU CGA AAU GUC C-3' (SEQ ID NO: 159) (to capture the anti-sense strand).

mfold Analysis

To model the end of an siRNA, the following 16 nt RNA sequence were submitted to mfold 3.1: (37° C., 1 M NaCl): CGU ACU UUU GUA CGU G (SEQ ID NO: 160), UGU ACU UUU GUA CGU G (SEQ ID NO: 161), and UCG AAU UU UUC GAA A (SEQ ID NO: 162).

Pre-let-7 Processing

Pre-let-7 RNA was incubated with N-terminal histadine-tagged, human Dicer according to the manufacterer's directions (Gene theraphy Systems) or in a standard Drosophilia embryo in vitro RNAi reaction as described previously (Hutvagner et al., 2001; Hutvagner and Zamore, 2002).

Northern Hybridization

Northern hybridization was essentially as described (Hutvágner et al., 2001).50 mg total RNA was loaded per lane. 5' 32P-radiolabeled synthetic RNA probes (Dharmacon) were: 5'-ACA AAU UCG GAU CUA CAG GGU-3' (SEQ ID NO: 163) (to detect miR-10) and 5'-AAA CCU CUC UAG AAC CGA AUU U-3' (SEQ ID NO: 164) (to detect miR-10*). The amount of miR-10 or miR-10* detected was normalized to the non-specific hybridization of the probe to 5S rRNA. Normalizing to hybridization of the probe to a known amount of a miR-10 or miR-10* synthetic RNA control yielded essentially the same result.

ATP-Depletion and N-Ethyl Maleimide (NEM) Inhibition

RNAi reactions using Drosophila embryo lysate were as described (Haley et al., 2003). To compare 'minus' and 'plus' ATP conditions, samples were treated with 10 mM NEM (Pierce) for 10 min at 4° C., then the NEM was quenched with 11 mM dithiothreitol (DTT). For ATP depletion (–ATP), 1 unit of hexokinase and 20 mM (final concentration) glucose were added and the incubation continued for 30 min at 25° C. For 'plus' ATP reactions, 0.05 mg ml–1 (final concentration) creatine kinase and one-tenth volume $H_2O$ substituted for hexokinase and glucose. The addition of fresh creatine kinase after NEM treatment did not rescue the defect in RISC assembly, but did restore ATP to high levels (Nykänen et al., 2001). ATP levels were measured using an ATP assay kit (Sigma) and a PhL luminometer (Mediators Diagnostika).

REFERENCES

Abrahante, J. E., Daul, A. L., Li, M., Volk, M. L., Tennessen, J. M., Miller, E. A., and Rougvie, A. E. (2003). The *Caenorhabditis elegans* hunchback-like Gene lin-57/hbl-1 Controls Developmental Time and Is Regulated by MicroRNAs. Dev Cell 4, 625-637.

Achard, P., Herr, A., Baulcombe, D. C., and Harberd, N. P. (2004). Modulation of floral development by a gibberellin-regulated microRNA. Development. 131(14): 3357-65.

Amarzguioui, M., Holen, T., Babaie, E., and Prydz, H. (2003). Tolerance for mutations and chemical modifications in a siRNA. Nucleic Acids Res 31, 589-595.

Ambros, V. (2003). MicroRNA pathways in flies and worms: growth, death, fat, stress, and timing. Cell. 113(6): 673-6.

Ambros, V., Bartel, B., Bartel, D. P., Burge, C. B., Carrington, J. C., Chen, X., Dreyfuss, G., Eddy, S. R., Griffiths-Jones, S., Marshall, M., et al. (2003). A uniform system for microRNA annotation. RNA 9, 277-279.

Amarzguioui, M., Holen, T., Babaie, E., and Prydz, H. (2003). Tolerance for mutations and chemical modifications in a siRNA. Nucleic Acids Res 31, 589-595.

Ambros, V., Lee, R. C., Lavanway, A., Williams, P. T., and Jewell, D. (2003). MicroRNAs and other tiny endogenous RNAs in *C. elegans*. Current Biology. 13: 807-818.

Aravin, A. A., Lagos-Quintana, M., Yalcin, A., Zavolan, M., Marks, D., Snyder, B., Gassterland, T., Meyer, J., and Tuschl, T. (2003). The small RNA profile during *Drososphila melanogaster* development. Developmental Cell. 5(2): 337-50.

Aukerman, M. J., and Sakai, H. (2003). Regulation of flowering time and floral organ identity by a MicroRNA and APETALA2-like target genes. Plant Cell. 10: 10.

Baehrecke, E. H. (2003). miRNAs: micromanagers of programmed cell death. Current Biology. 13(12): R473-5.

Bartel, D. P. MicroRNAs: Genomics, biogenesis, mechanism, and function. Cell 116, 281-297 (2004).

Bartel, D. P., and Chen, C. Z. (2004). Micromanagers of gene expression: the potentially widespread influence of metazoan microRNAs. Nature Reviews Genetics. 396-400.

Bartel, B. and Bartel, D. P. (2003). MicroRNAs: at the root of plant development? Plant Physiology. 132(2): 709-17.

Bernstein, E., Caudy, A. A., Hammond, S. M., and Hannon, G. J. (2001). Role for a bidentate ribonuclease in the initiation step of RNA interference. Nature 409, 363-366.

Billy, E., Brondani, V., Zhang, H., Muller, U., and Filipowicz, W. (2001). Specific interference with gene expression induced by long, double-stranded RNA in mouse embryonal teratocarcinoma cell lines. Proc Natl Acad Sci USA 98, 14428-14433.

Boutla, A., Delidakis, C., and Tabler, M. (2003). Developmental defects by antisense-mediated inactivation of micro-RNAs 2 and 13 in Drosophila and the identification of putative target genes. Nucleic Acids Research. 31(17): 4973-4980.

Boutla, A., Delidakis, C., Livadaras, I., Tsagris, M., and Tabler, M. (2001). Short 5'-phosphorylated double-stranded RNAs induce RNA interference in Drosophila. Curr Biol 11, 1776-1780.

Brennecke, J., Hipfner, D. R., Stark, A., Russell, R. B., and Cohen, S. M. (2003). bantam Encodes a Developmentally Regulated microRNA that Controls Cell Proliferation and Regulates the Proapoptotic Gene hid in Drosophila. Cell 113, 25-36.

Bridge, A. J., Pebernard, S., Ducraux, A., Nicoulaz, A. L., and Iggo, R. (2003). Induction of an interferon response by RNAi vectors in mammalian cells. Nat Genet.

Brummelkamp, T. R., Bernards, R., and Agami, R. (2002). A system for stable expression of short interfering RNAs in mammalian cells. Science 296, 550-553.

Calin, G. A., Sevignani, C., Dumitru, C. D., Hyslop, T., Noch, E., Yendamuri, S., Shimizu, M., Rattan, S., Bullrich, R., Negrini, M., and Croce, C. M. (2004). Human microRNA genes are frequently located at fragile sites and genomic regions involved in cancer. Proceedings of the National Academy of Sciences USA. 101(9): 2999-3004.

Calin, G. A., Dumitru, C. D., Shimizu, M., Bichi, R., Zupo, S., Noch, E., Aldler, H., Rattan, S., Keating, M., Rai, K., Rassenti, L., Kipps, T., Negrini, M., Bullrich, F., and Croce, C. M. (2002). Frequent deletions and down-regulation of micro-RNA genes miR15 and miR16 at 13q14 in chronic lymphocytic leukemia. Proceedings of the National Academy of Sciences USA. 99(24): 15524-9.

Carrington, J. C., and Ambros, V. (2003). Role of microRNAs in plant and animal development. Science. 301(5631): 336-8.

Caudy, A. A., Myers, M., Hannon, G. J., and Hammond, S. M. (2002). Fragile X-related protein and VIG associate with the RNA interference machinery. Genes Dev 16, 2491-2496.

Chelladurai, B., Li, H., Zhang, K., and Nicholson, A. W. (1993). Mutational analysis of a ribonuclease III processing signal. Biochemistry 32, 7549-7558.

Chen, C. Z., Li, L., Lodish, H. F., and Bartel, D. P. (2004). MicroRNAs modulate hematopoietic lineage differentiation. Science. 303: 63-86.

Chen, X. (2003). A MicroRNA as a Translational Repressor of APETALA2 in Arabidopsis Flower Development. Science (Science Express 10.1126/science. 1088060).

Chi, J. T., Chang, H. Y., Wang, N. N., Chang, D. S., Dunphy, N., and Brown, P. O. (2003). Genomewide view of gene silencing by small interfering RNAs. Proceedings of the National Academy of Sciences USA. 100(11): 6343-6346.

Chiu, Y.-L., and Rana, T. M. (2002). RNAi in Human Cells: Basic Structural and Functional Features of Small Interfering RNA. Molecular Cell 10, 549-561.

Chiu, Y. L. & Rana, T. M. siRNA function in RNAi: a chemical modification analysis. RNA 9, 1034-1048 (2003).

Crow, J. P., Sampson, J. B., Zhuang, Y., Thompson, J. A., and Beckman, J. S. (1997). Decreased zinc affinity of amyotrophic lateral sclerosis-associated superoxide dismutase mutants leads to enhanced catalysis of tyrosine nitration by peroxynitrite. J Neurochem 69, 1936-1944.

Djikeng, A., Shi, H., Tschudi, C., and Ullu, E. (2001). RNA interference in Trypanosoma brucei: cloning of small interfering RNAs provides evidence for retroposon-derived 24-26-nucleotide RNAs. RNA 7, 1522-1530.

D. H. Mathews, J. S., M. Zuker & D. H. Turner (1999). Expanded Sequence Dependence of Thermodynamic Parameters Improves Prediction of RNA Secondary Structure. J Mol Biol 288, 911-940.

Dalmay, T., Horsefield, R., Braunstein, T. H., and Baulcombe, D. C. (2001). SDE3 encodes an RNA helicase required for post-transcriptional gene silencing in Arabidopsis. EMBO J 20, 2069-2078.

Ding, H. et al. Selective silencing by RNAi of a dominant allele that causes amyotrophic lateral sclerosis. Aging Cell 2, 209-217 (2003).

Doench, J. G., Petersen, C. P., and Sharp, P. A. (2003). siRNAs can function as miRNAs. Genes Dev 17, 438-442.

Doench, J. G. & Sharp, P. A. Specificity of microRNA target selection in translational repression. Genes Dev. 18, 504-511 (2004).

Doi, N., Zenno, S., Ueda, R., Ohki-Hamazaki, H., Ui-Tei, K., and Saigo, K. (2003). Short-Interfering-RNA-Mediated Gene Silencing in Mammalian Cells Requires Dicer and eIF2C Translation Initiation Factors. Curr Biol 13, 41-46.

Dostie, J., Mourelatos, Z., Yang, M., Sharma, A., and Dreyfuss, G. (2003). Numerous microRNPs in neuronal cells containing novel microRNAs. RNA. 9: 180-6.

Elbashir, S. M., Lendeckel, W., and Tuschl, T. (2001a). RNA interference is mediated by 21- and 22-nucleotide RNAs. Genes Dev 15, 188-200.

Elbashir, S. M., Martinez, J., Patkaniowska, A., Lendeckel, W., and Tuschl, T. (2001b). Functional anatomy of siRNAs for mediating efficient RNAi in Drosophila melanogaster embryo lysate. EMBO J 20, 6877-6888.

Elbashir, S. M. et al. Duplexes of 21-nucleotide RNAs mediate RNA interference in cultured mammalian cells. Nature 411, 494-498 (2001).

Emery, J. F., Floyd, S. K., Alvarez, J., Eshed, Y., Hawker, N. P., Izhaki, A., Baum, S. F., and Bowman, J. L. (2003). Radial patterning of Arabidopsis shoots by class III HD-ZIP and KANADI genes. Cuurent Biology. 13: 1768-1774.

Enright, A. et al. MicroRNA targets in Drosophila. Genome Biol. 5, R1 (2003).

Fire, A., Xu, S., Montgomery, M. K., Kostas, S. A., Driver, S. E., and Mello, C. C. (1998). Potent and specific genetic interference by double-stranded RNA in Caenorhabditis elegans. Nature 391, 806-811.

Grad, Y., Aach, J., Hayes, G. D., Reinhart, B. J., Church, G. M., Ruvkun, G., et. al., (2003). Computational and experimental identification of C. elegans microRNAs. Molecular Cell. 11(5): 1253-63.

Griffiths-Jones, S. (2004). The microRNA registry. Nucleic Acids Research. 32: D109-111.

Grishok, A., Pasquinelli, A. E., Conte, D., Li, N., Parrish, S., Ha, I., Baillie, D. L., Fire, A., Ruvkun, G., and Mello, C. C. (2001). Genes and Mechanisms Related to RNA Interference Regulate Expression of the Small Temporal RNAs that Control *C. elegans* Developmental Timing. Cell 106, 23-34.

Hake, S. (2003). MicroRNAs: a role in plant development. Current Biology. 13(21): R851-2.

Haley, B., Tang, G. & Zamore, P. D. In vitro analysis of RNA interference in *Drosophila melanogaster*. Methods 30, 330-336 (2003).

Hamilton, A. J., and Baulcombe, D. C. (1999). A species of small antisense RNA in posttranscriptional gene silencing in plants. Science 286, 950-952.

Hammond, S. M., Bernstein, E., Beach, D., and Hannon, G. J. (2000). An RNA-directed nuclease mediates post-transcriptional gene silencing in *Drosophila* cells. Nature 404, 293-296.

Hammond, S. M., Caudy, A. A., and Hannon, G. J. (2001). Post-transcriptional gene silencing by double-stranded RNA. Nat Rev Genet 2, 110-119.

Hannon, G. J. & Zamore, P. D. Small RNAs, Big Biology: and Biochemical Studies of RNA Interference. In RNAi: A Guide To Gene Silencing (ed. Hannon, G. J.) 87-108 (Cold Spring Harbor Laboratory Press, Cold Spring Harbor, N.Y.; 2003).

Holen, T., Amarzguioui, M., Babaie, E. & Prydz, H. Similar behaviour of single-strand and double-strand siRNAs suggests they act through a common RNAi pathway. Nucleic Acids Res 31, 2401-2407 (2003).

Houbaviy, H. B., Murray, M. F., and Sharp, P. A. (2003). Embryonic stem cell-specific MicroRNAs. Developmental Cell. 5(2): 351-8.

Hunter, C., and Poethig, R. S. (2003). miSSING LINKS: miRNAs and plant development. Current Opinion in Genetics and Development. 13(4): 372-8.

Hutvágner, G., McLachlan, J., Pasquinelli, A. E., Balint, É., Tuschl, T., and Zamore, P. D. (2001). A cellular function for the RNA-interference enzyme Dicer in the maturation of the let-7 small temporal RNA. Science 293, 834-838.

Hutvágner, G., and Zamore, P. D. (2002). A MicroRNA in a Multiple-Turnover RNAi Enzyme Complex. Science 297, 2056-2060.

Hutvágner, G., Simard, M. J., Mello, C. C. & Zamore, P. D. Sequence-specific inhibition of small RNA function. PLoS Biology 2, 1-11 (2004).

Ishizuka, A., Siomi, M. C., and Siomi, H. (2002). A *Drosophila* fragile X protein interacts with components of RNAi and ribosomal proteins. Genes Dev 16, 2497-2508.

Jackson, A. L., Bartz, S. R., Schelter, J., Kobayashi, S. V., Burchard, J., Mao, M., Li, B., Cavet, G., and Linsley, P. S. (2003). Expression profiling reveals off-target gene regulation by RNAi. Nat Biotechnol 21, 635-637.

Johnston, R. J. & Hobert, O. A microRNA controlling left/right neuronal asymmetry in *Caenorhabditis elegans*. Nature 426, 845-849 (2003).

Kasschau, K. D., Xie, Z., Allen, E., Llave, C., Chapman, E. J., Krizan, K. A., and Carrington, J. C. (2003). P1/HC-Pro, a Viral Suppressor of RNA Silencing, Interferes with *Arabidopsis* Development and miRNA Function. Dev Cell 4, 205-217.

Kawasaki, H., and Taira, K. (2003). Hes1 is a target of microRNA-23 during retinoic-acid-induced neuronal differentiation of NT2 cells. Nature. 423(6942): 838-42.

Kennerdell, J. R., Yamaguchi, S., and Carthew, R. W. (2002). RNAi is activated during *Drosophila* oocyte maturation in a manner dependent on aubergine and spindle-E. Genes Dev 16, 1884-1889.

Ketting, R. F., Fischer, S. E., Bernstein, E., Sijen, T., Hannon, G. J., and Plasterk, R. H. (2001). Dicer functions in RNA interference and in synthesis of small RNA involved in developmental timing in *C. elegans*. Genes Dev 15, 2654-2659.

Khvorova, A., Reynolds, A. & Jayasena, S. D. Functional siRNAs and miRNAs exhibit strand bias. Cell 115, 209-216 (2003).

Kidner, C. A., and Martienssen, R. A. (2004). Spatially restricted microRNA directs leaf polarity through ARGONAUTE1. Nature. 428(6978): 81-4.

Kidner, C. A., and Martienssen, R. A. (2003). Macro effects of microRNAs in plants. Trends in Genetics. 19(1): 13-6.

Kim, J., Krichevsky, A., Grad, Y., Hayes, G. D., Kosik, K. S., Church, G. M., and Ruvkun, G. (2004). Identification of many microRNAs that copurify with polyribosomes in mammalian neurons. Proceedings of the National Academy of Sciences. 101(1): 360-365.

Knight, S. W., and Bass, B. L. (2001). A role for the RNase III enzyme DCR-1 in RNA interference and germ line development in *Caenorhabditis elegans*. Science 293, 2269-2271.

Krichevsky, A. M, King, K. S., Donahue, C. P., Khrapko, K., and Kosik, K. S. (2003). A microRNA array reveals extensive regulation of microRNAs during brain development. RNA. 9(10): 1274-81.

Lagos-Quintana, M., Rauhut, R., Lendeckel, W., and Tuschl, T. (2001). Identification of Novel Genes Coding for Small Expressed RNAs. Science 294, 853-858.

Lagos-Quintana, M., Rauhut, R., Yalcin, A., Meyer, J., Lendeckel, W., and Tuschl, T. (2002). Identification of Tissue-Specific MicroRNAs from Mouse. Curr Biol 12, 735-739.

Lagos-Quintana, M., Rauhut, R., Meyer, J., Borkhardt, A., and Tuschl, T. (2003). New microRNAs from mouse and human. RNA 9, 175-179.

Lai, E. C., Tomancak, P., Williams, R. W., and Rubin, G. M. (2003). Computational identification of *Drosophila* microRNA genes. Genome Biology. 4: R42, 1-20.

Lai, E. C. Micro RNAs are complementary to 3' UTR sequence motifs that mediate negative post-transcriptional regulation. Nat Genet 30, 363-364 (2002).

Lau, N. C., Lim, L. P., Weinstein, E. G., and Bartel, D. P. (2001). An Abundant Class of Tiny RNAs with Probable Regulatory Roles in *Caenorhabditis elegans*. Science 294, 858-862.

Lee, R. C., and Ambros, V. (2001). An Extensive Class of Small RNAs in *Caenorhabditis elegans*. Science 294, 862-864.

Lee, R. C., Feinbaum, R. L., and Ambros, V. (1993). The *C. elegans* heterochronic gene lin-4 encodes small RNAs with antisense complementarity to lin-14. Cell 75, 843-854.

Lewis, B., Shih, I., Jones-Rhoades, M., Bartel, D. & Burge, C. Prediction of mammalian microRNA targets. Cell 115, 787-798 (2003).

Lim, L. P., Glasner, M. E., Yekta, S., Burge, C. B., and Bartel, D. P. (2003a). Vertebrate microRNA genes. Science 299, 1540.

Lim, L. P., Lau, N. C., Weinstein, E. G., Abdelhakim, A., Yekta, S., Rhoades, M. W., Burge, C. B., and Bartel, D. P. (2003b). The microRNAs of *Caenorhabditis elegans*. Genes Dev 17, 991-1008.

Lin, S. Y., Johnson, S. M., Abraham, M., Vella, M. C., Pasquinelli, A., Gamberi, C., Gottlieb, E., and Slack, F. J. (2003). The *C. elegans* hunchback Homolog, hbl-1, Controls Temporal Lima, W. F. & Crooke, S. T. Binding affinity and specificity of *Escherichia coli* RNase H1: impact on the kinetics of catalysis of antisense oligonucleotide-RNA hybrids. Biochemistry 36, 390-398 (1997).

Llave, C., Kasschau, K. D., Rector, M. A., and Carrington, J. C. (2002a). Endogenous and Silencing-Associated Small RNAs in Plants. Plant Cell 14, 1605-1619.

Llave, C., Xie, Z., Kasschau, K. D., and Carrington, J. C. (2002b). Cleavage of Scarecrow-Like mRNA Targets Directed by a Class of *Arabidopsis* miRNA. Science 297, 2053-2056.

Mallory, A. C., Dugas, D. V., Bartel, D. P., and Bartel, B. (2004). MicroRNA regulation of NAC-domain targets is required for proper formation and separation of adjacent embryonic, vegetative, and floral organs. Current Biology. 14(12): 1035-46.

Mallory, A. C., Reinhart, B. J., Bartel, D., Vance, V. B., and Bowman, L. H. (2002). A viral suppressor of RNA silencing differentially regulates the accumulation of short interfering RNAs and micro-RNAs in tobacco. Proc Natl Acad Sci USA 99, 15228-15233.

Martinez, J., Patkaniowska, A., H, H. U., Lührmann, R., and Tuschl, T. (2002). Single stranded antisense siRNA guide target RNA cleavage in RNAi. Cell 110, 563-574.

Martinez, J. & Tuschl, T. RISC is a 5' phosphomonoester-producing RNA endonuclease. Genes Dev. Published online, Apr. 22, 2004, 10.1101/gad.1187904 (2004).

McManus, M. T., Petersen, C. P., Haines, B. B., Chen, J., and Sharp, P. A. (2002). Gene silencing using micro-RNA designed hairpins. RNA 8, 842-850.

McManus, M. T. (2003). MicroRNAs and cancer. Seminars in Cancer Biology. 13(4): 253-8.

Meister, G., Landthaler, M., Dorsett, Y. & Tuschl, T. Sequence-specific inhibition of microRNA- and siRNA-induced RNA silencing. RNA 10, 544-550 (2004).

Michael, M. Z., O'Connor, S. M., van Holst Pellekaan, N. G., Young, G. P., and James, R. J. (2003). Reduced accumulation of specific microRNAs in colorectal neoplasia. Molecular Cancer Research. 1(12): 882-91.

Myers, J. W., Jones, J. T., Meyer, T., and Ferrell, J. E. (2003). Recombinant Dicer efficiently converts large dsRNAs into siRNAs suitable for gene silencing. Nat Biotechnol.

Mourelatos, Z., Dostie, J., Paushkin, S., Sharma, A. K., Charroux, B., Abel, L., Rappsilber, J., Mann, M., and Dreyfuss, G. (2002). miRNPs: a novel class of Ribonucleoproteins containing numerous microRNAs. Genes Dev 16, 720-728.

Nykänen, A., Haley, B., and Zamore, P. D. (2001). ATP Requirements and Small Interfering RNA Structure in the RNA Interference Pathway. Cell 107, 309-321.

Olsen, P. H., and Ambros, V. (1999). The lin-4 regulatory RNA controls developmental timing in *Caenorhabditis elegans* by blocking LIN-14 protein synthesis after the initiation of translation. Dev Biol 216, 671-680.

Paddison, P. J., Caudy, A. A., Bernstein, E., Hannon, G. J., and Conklin, D. S. (2002). Short hairpin RNAs (shRNAs) induce sequence-specific silencing in mammalian cells. Genes Dev 16, 948-958.

Palatnik, J. F., Allen, E., Wu, X., Schommer, C., Scwab, R., Carrington, J. C., and Weigel, D. (2003). Control of leaf morphogenesis by microRNAs. Nature. 425: 257-263.

Park, W., Li, J., Song, R., Messing, J., and Chen, X. (2002). CARPEL FACTORY, a Dicer Homolog, and HEN1, a Novel Protein, Act in microRNA Metabolism in *Arabidopsis thaliana*. Curr Biol 12, 1484-1495.

Pasquinelli, A. E., and Ruvkun, G. (2002). Control of developmental timing by microRNAs and their targets. Annual Reviews in Cellular and Developmental Biology. 18: 495-513.

Pasquinelli, A. E., Reinhart, B. J., Slack, F., Martindale, M. Q., Kuroda, M. I., Maller, B., Hayward, D. C., Ball, E. E., Degnan, B., Muller, P., et al. (2000). Conservation of the sequence and temporal expression of let-7 heterochronic regulatory RNA. Nature 408, 86-89.

Paul, C. P., Good, P. D., Winer, I., and Engelke, D. R. (2002). Effective expression of small interfering RNA in human cells. Nat Biotechnol 20, 505-508.

Pham, J. W., Pellino, J. L., Lee, Y. S., Carthew, R. W. & Sontheimer, E. J. A Dicer-2-dependent 80S complex cleaves targeted mRNAs during RNAi in *Drosophila*. Cell 117, 83-94 (2004).

Phipps, K. M., Martinez, A., Lu, J., Heinz, B. A. & Zhao, G. Small interfering RNA molecules as potential anti-human rhinovirus agents: in vitro potency, specificity, and mechanism. Antiviral Res 61, 49-55 (2004).

Provost, P., Dishart, D., Doucet, J., Frendewey, D., Samuelsson, B., and Radmark, O. (2002). Ribonuclease activity and RNA binding of recombinant human Dicer. EMBO J 21, 5864-5874.

Pusch, O., Boden, D., Silbermann, R., Lee, F., Tucker, L., and Ramratnam, B. (2003). Nucleotide sequence homology requirements of HV-1-specific short hairpin RNA. Nucleic Acids Research. 31: 6444-9.

Rajewsky, N. & Socci, N. D. Computational identification of microRNA targets. Dev. Biol. 267, 529-535 (2004).

Reinhart, B. J., and Bartel, D. P. (2002). Small RNAs correspond to centromere heterochromatic repeats. Science. 297: 1831.

Reinhart, B. J., Slack, F. J., Basson, M., Pasquinelli, A. E., Bettinger, J. C., Rougvie, A. E., Horvitz, H. R., and Ruvkun, G. (2000). The 21-nucleotide let-7 RNA regulates developmental timing in *Caenorhabditis elegans*. Nature 403, 901-906.

Reinhart, B. J., Weinstein, E. G., Rhoades, M. W., Bartel, B., and Bartel, D. P. (2002). MicroRNAs in plants. Genes Dev 16, 1616-1626.

Reynolds, A. et al. Rational siRNA design for RNA interference. Nature Biotechnology 22, 326-330 (2004).

Rhoades, M. W., Reinhart, B. J., Lim, L. P., Burge, C. B., Bartel, B., and Bartel, D. P. (2002). Prediction of Plant MicroRNA Targets. Cell 110, 513-520.

Ruvkun, G. (2001). Molecular biology. Glimpses of a tiny RNA world. Science 294, 797-799.

Schwarz, D. S. and Zamore, P. D. (2002). Why do miRNAs live in the miRNP? Genes & Development. 16: 1025-1031.

Schwarz, D. S., Hutvágner, G., Haley, B., and Zamore, P. D. (2002). Evidence that siRNAs function as guides, not primers, in the *Drosophila* and human RNAi pathways. Molecular Cell 10, 537-548.

Schwarz, D. S. et al. Asymmetry in the assembly of the RNAi enzyme complex. Cell 115, 199-208 (2003).

Schwarz, D. S., Tomari, Y. & Zamore, P. D. The RNA-induced silencing complex is a Mg2+-dependent endonuclease. Curr. Biol. 14, 787-791 (2004).

Semizarov, D., Frost, L., Sarthy, A., Kroeger, P., Halbert, D. N., and Fesik, S. W. (2003). Specificity of short interfering RNA determined through gene expression signatures. Proceedings of the National Academy of Sciences USA. 100 (11): 6347-6342.

Sempere, L. F., Freemantle, S., Pitha-Rowe, I., Moss, E., Dmitrovasky, E., and Ambros, V. (2004). Expression profiling of mammalian microRNAs uncovers a subset of brain-expressed microRNAs with possible roles in murine and human neuronal differentiation. Genome Biology. 5: R13

Sijen, T., Fleenor, J., Simmer, F., Thijssen, K. L., Parrish, S., Timmons, L., Plasterk, R. H., and Fire, A. (2001). On the Role of RNA Amplification in dsRNA-Triggered Gene Silencing. Cell 107, 465-476.

Silhavy, D., Molnar, A., Lucioli, A., Szittya, G., Hornyik, C., Tavazza, M., and Burgyan, J. (2002). A viral protein suppresses RNA silencing and binds silencing-generated, 21- to 25-nucleotide double-stranded RNAs. EMBO J 21, 3070-3080.

Slack, F. J., Basson, M., Liu, Z., Ambros, V., Horvitz, H. R., and Ruvkun, G. (2000). The lin-41 RBCC gene acts in the C. elegans heterochronic pathway between the let-7 regulatory RNA and the LIN-29 transcription factor. Mol Cell 5, 659-669.

Stark, A., Brennecke, J., Russel, R. & Cohen, S. Identification of Drosophila microRNA targets. PLoS Biology 1, 1-13 (2003).

Stryer, L. Biochemistry. (W. H. Freeman and Company, San Francisco; 1981).

Tabara, H., Yigit, E., Siomi, H., and Mello, C. C. (2002). The dsRNA Binding Protein RDE-4 Interacts with RDE-1, DCR-1, and a DexH-Box Helicase to Direct RNAi in C. elegans. Cell 109, 861-871.

Takamizawa, J., Konishi, H., Yanagisawa, K., Tomida, S., Osada, H., Endoh, H., Harano, T., Yatabe, Y., Nagino, M., Nimura, Y., Mitsudomi, T., and Takahashi, T. (2004). Reduced expression of the let-7 MicroRNAs in Human Lung Cancers in Association with Shortened Postoperative Survival. Cancer Research. 64: 3753-6.

Tang, G., Reinhart, B. J., Bartel, D. P., and Zamore, P. D. (2003). A biochemical framework for RNA silencing in plants. Genes Dev 17, 49-63.

Tijsterman, M., Ketting, R. F., Okihara, K. L., Sijen, T., and Plasterk, R. H. (2002). RNA helicase MUT-14-dependent gene silencing triggered in C. elegans by short antisense RNAs. Science 295, 694-697.

Tomari, Y. et al. RISC assembly defects in the Drosophila RNAi mutant armitage. Cell 116, 831-841 (2004).

Tuschl, T., Zamore, P. D., Lehmann, R., Bartel, D. P., and Sharp, P. A. (1999). Targeted mRNA degradation by double-stranded RNA in vitro. Genes Dev 13, 3191-3197.

Vaucheret, H., Vazques, F., Crata, P., and Bartel, D. P. (2004). The action of ARGONAUTE1 in the miRNA pathway and its regulation by the miRNA pathway are crucial for plant development. Genes & Development. 18(10):1187-97.

Vella, M., Choi, E., Lin, S., Reinert, K. & Slack, F. The C. elegans microRNA let-7 binds to imperfect let-7 complementary sites from the lin-41 3'UTR. Genes Dev. 18, 132-137 (2004).

Voet, D. & Voet, J. G. Biochemistry. (John Wiley & Sons, Hoboken, N.J.; 2004).

Wightman, B., Ha, I., and Ruvkun, G. (1993). Posttranscriptional regulation of the heterochronic gene lin-14 by lin-4 mediates temporal pattern formation in C. elegans. Cell 75, 855-862.

Wu, H., Lima, W. F. & Crooke, S. T. Investigating the structure of human RNase H1 by site-directed mutagenesis. J. Biol. Chem. 276, 23547-23553. (2001).

Wu-Scharf, D., Jeong, B., Zhang, C., and Cerutti, H. (2000). Transgene and transposon silencing in chlamydomonas reinhardtii by a DEAH-Box RNA helicase. Science 290, 1159-1163.

Xie, Z., Kasschau, K. D., and Carrington, J. C. (2003). Negative Feedback Regulation of Dicer-Like1 in Arabidopsis by microRNA-Guided mRNA Degradation. Curr Biol 13, 784-789.

Xu, P., Vernooy, S. Y., Guo, M., and Hay, B. A. (2003). The Drosophila MicroRNA Mir-14 Suppresses Cell Death and Is Required for Normal Fat Metabolism. Curr Biol 13, 790-795.

Yekta, S., Shih, I., and Bartel, D. P. (2004). MicroRNA-Directed Cleavage of HOXB8 mRNA. Science 304: 594-6.

Yu, J. Y., DeRuiter, S. L., and Turner, D. L. (2002). RNA interference by expression of short-interfering RNAs and hairpin RNAs in mammalian cells. Proc Natl Acad Sci USA 99, 6047-6052.

Zamore, P. D., Tuschl, T., Sharp, P. A., and Bartel, D. P. (2000). RNAi: double-stranded RNA directs the ATP-dependent cleavage of mRNA at 21 to 23 nucleotide intervals. Cell 101, 25-33.

Zeng, Y, and Cullen, B. R. (2003). Sequence requirements for micro RNA processing and function in human cells. RNA. 9: 112-123.

Zeng, Y., Yi, R., and Cullen, B. R. (2003). MicroRNAs and small interfering RNAs can inhibit mRNA expression by similar mechanisms. Proceedings of the National Academy of Sciences. 100(17): 9779-9784.

Zeng, Y., Wagner, E. J., and Cullen, B. R. (2002). Both natural and designed microRNAs can inhibit the expression of cognate mRNAs when expressed in human cells. Molecular Cell. 9: 1327-33.

Zhang, H., Kolb, F. A., Brondani, V., Billy, E., and Filipowicz, W. (2002). Human Dicer preferentially cleaves dsRNAs at their termini without a requirement for ATP. EMBO J 21, 5875-5885.

Zhong, R., and Ye, Z. H. (2004). Amphivasal vascular bundle 1, a gain-of-function mutation of the IFL1/REV gene, is associated with alterations in the polarity of leaves, stems, and carpels. Plant Cell Physiology. 45(4): 369-385.

Zuker, M. (2003). Mfold web server for nucleic acid folding and hybridization prediction. Nucleic Acids Res 31, 1-10.

Equivalents

Those skilled in the art will recognize, or be able to ascertain using no more than routine experimentation, many equivalents to the specific embodiments of the invention described herein. Such equivalents are intended to be encompassed by the following claims.

TABLE 1

Table 1 Kinetic analysis of RISC
Summary of kinetic data from the analysis in FIG. 17A. For comparison, the $K_M$ and $k_{cat}$ values of four well studied protein enzymes are provided[43,44]. $K_M$ and $k_{cat}$ ± error of fit are reported.

| Mismatches, position | $K_M$ (nM) | $V_{max}$ (nM s$^{-1}$) | [RISC] (nM) | $k_{cat}$ (s$^{-1}$) | $k_{cat} K_M^{-1}$ (nM$^{-1}$ s$^{-1}$) | fold change, $k_{cat} K_M^{-1}$ |
|---|---|---|---|---|---|---|
| none | 8.4 ± 1.6 | 0.0071 | 1 | 7.1 × 10$^{-3}$ | 8.4 × 10$^{-4}$ | 1.00 |
| three nt 3' | 2.7 ± 0.6 | 0.0022 | 2 | 1.1 × 10$^{-3}$ | 3.8 × 10$^{-4}$ | 0.46 |

TABLE 1-continued

Table 1 Kinetic analysis of RISC
Summary of kinetic data from the analysis in FIG. 17A. For comparison, the $K_M$ and $k_{cat}$ values of four well studied protein enzymes are provided[43,44]. $K_M$ and $k_{cat}$ ± error of fit are reported.

| | | | | | | |
|---|---|---|---|---|---|---|
| five nt 3' | 6.0 ± 1.8 | 0.0054 | 2 | $2.7 \times 10^{-4}$ | $4.5 \times 10^{-5}$ | 0.05 |
| three nt 5' | 4.7 ± 1.3 | 0.0063 | 2 | $3.2 \times 10^{-3}$ | $6.7 \times 10^{-4}$ | 0.80 |

| Reference enzymes | $K_M$ (nM) | $k_{cat}$ (s$^{-1}$) | $k_{cat} K_M^{-1}$ (nM$^{-1}$ s$^{-1}$) | $k_{cat} K_M^{-1}$ relative to RISC |
|---|---|---|---|---|
| Urease (ref 43) | $2.5 \times 10^7$ | $1 \times 10^4$ | $4.0 \times 10^{-4}$ | 0.47 |
| Fumarase (ref 43) | $5.0 \times 10^3$ | $8 \times 10^2$ | $1.6 \times 10^{-1}$ | 190 |
| Catalase (ref 43) | $2.5 \times 10^7$ | $1 \times 10^7$ | $4.0 \times 10^{-1}$ | 8940 |
| RNase H1 (ref 44) | $3.8 \times 10^1$ | $5 \times 10^2$ | $1.3 \times 10^{-3}$ | 0.03 |

---

What is claimed:

1. A method of producing a dsRNAi agent having decreased off-target silencing activity, the method comprising:

(a) identifying an off-target silencing activity mediated by a sense strand of a first dsRNAi agent, wherein the first dsRNAi agent directs cleavage by a RISC complex at a phosphodiester bond within a desired target mRNA; and (b) synthesizing a substituted dsRNAi agent comprising one or more substituted base pairs with respect to the first dsRNAi agent, wherein the substituted dsRNAi agent comprises a sense and an antisense strand, each strand having a 5' end and a 3' end, wherein the substituted dsRNAi agent directs cleavage by the RISC complex at the same phosphodiester bond within the desired target mRNA, wherein the one or more substituted base pairs are within about 5 base pairs from the 5' end of the antisense strand (AS 5') and the 3' end of the sense strand (S 3') and are selected from the group consisting of a mismatched base pair, a wobble base pair, a base pair comprising a rare nucleotide and a base pair comprising a base-modified nucleotide, such that the sense strand of the substituted dsRNAi agent is less effective than the sense strand of the first dsRNAi agent at entering the RISC complex;

such that the substituted dsRNAi agent has decreased off-target silencing activity relative to the off-target silencing activity of the first dsRNAi agent.

2. The method of claim 1, wherein the one or more substituted base pairs comprise at least one mismatched base pair.

3. The method of claim 2, wherein the mismatched base pair is selected from the group consisting of G:A, C:A, C:T, C:U, G:G, A:A, C:C, U:T, and U:U.

4. The method of claim 1, wherein the one or more substituted base pairs comprise at least one wobble base pair.

5. The method of claim 4, wherein the wobble base pair is selected from the group consisting of a G:U or G:T.

6. The method of claim 1, wherein the one or more substituted base pairs comprise at least one base pair comprising a rare nucleotide.

7. The method of claim 6, wherein the rare nucleotide is inosine (I).

8. The method of claim 6, wherein the base pair is selected from the group consisting of an I:A, I:U and I:C.

9. The method of claim 1, wherein the one or more substituted base pairs comprise at least one base pair comprising a base-modified nucleotide.

10. The method of claim 9, wherein the base-modified nucleotide is selected from the group consisting of 2-amino-G, 2-amino-A, 2,6-diamino-G, and 2,6-diamino-A.

11. A method of decreasing off-target silencing of an inadvertent target mRNA by a dsRNAi agent, the method comprising:

(a) identifying off-target silencing of an inadvertent target mRNA by a sense strand of a first dsRNAi agent, wherein the first dsRNAi agent directs cleavage by a RISC complex at a phosphodiester bond within a desired target mRNA; and (b) contacting a cell or subject having an RNAi pathway and the inadvertent target mRNA with a substituted dsRNAi agent comprising one or more substituted base pairs with respect to the first dsRNAi agent, wherein the substituted dsRNAi agent comprises a sense strand and an antisense strand, each strand having a 5' end and a 3' end, and wherein the substituted dsRNAi agent directs cleavage by the RISC complex at the same phosphodiester bond within the desired target mRNA, wherein the one or more substituted base pairs are within about 5 base pairs from the 5' end of the antisense strand (AS 5') and the 3' end of the sense strand (S 3') and are selected from the group consisting of a mismatched base pair, a wobble base pair, a base pair comprising a rare nucleotide and a base pair comprising a base-modified nucleotide, such that the sense strand of the substituted dsRNAi agent is less effective than the sense strand of the first dsRNAi agent at entering the RISC complex; such that off-target silencing of the inadvertent target mRNA by the substituted dsRNAi agent is decreased relative to the off-target silencing of the inadvertent target mRNA by the first dsRNAi agent.

12. The method of claim 1 or 11, wherein the dsRNAi agent is a siRNA duplex.

13. The method of claim 1 or 11, wherein the dsRNAi agent is derived from an engineered precursor.

14. A method of producing an siRNA-like duplex having decreased off-target silencing activity, the method comprising:
   (a) identifying an off-target silencing activity mediated by a miRNA* strand of a first siRNA-like duplex, wherein the first siRNA-like duplex directs silencing by a RISC complex of a desired target mRNA; and
   (b) synthesizing a substituted siRNA-like duplex comprising one or more substituted base pairs with respect to the first siRNA-like duplex, wherein the substituted siRNA-like duplex comprises a miRNA* strand and a miRNA strand, each strand having a 5' end and a 3' end, wherein the substituted siRNA-like duplex directs silencing by the RISC complex of the desired target mRNA, wherein the one or more substituted base pairs are within about 5 base pairs from the 5' end of the miRNA strand (miRNA 5') and the 3' end of the miRNA* strand (miRNA* 3') and are selected from the group consisting of a mismatched base pair, a wobble base pair, a base pair comprising a rare nucleotide and a base pair comprising a base-modified nucleotide, such that the miRNA* strand of the substituted siRNA-like duplex is less effective than the miRNA* strand of the first siRNA-duplex at entering the RISC complex;
such that the substituted siRNA-like duplex has decreased off-target silencing activity relative to the off-targeting silencing activity of the first siRNA-like duplex.

15. The method of claim 14, wherein the one or more substituted base pairs comprise at least one mismatched base pair.

16. The method of claim 14, wherein the mismatched base pair is selected from the group consisting of G:A, C:A, C:T, C:U, G:G, A:A, C:C, U:T, and U:U.

17. The method of claim 14, wherein the one or more substituted base pairs comprise at least one wobble base pair.

18. The method of claim 17, wherein the wobble base pair is selected from the group consisting of a G:U or G:T.

19. The method of claim 14, wherein the one or more substituted base pairs comprise at least one base pair comprising a rare nucleotide.

20. The method of claim 19, wherein the rare nucleotide is inosine (I).

21. The method of claim 19, wherein the base pair is selected from the group consisting of an I:A, I:U and I:C.

22. The method of claim 14, wherein the one or more substituted base pairs comprise at least one base pair comprising a base-modified nucleotide.

23. The method of claim 22, wherein the base-modified nucleotide is selected from the group consisting of 2-amino-G, 2-amino-A, 2,6-diamino-G, and 2,6-diamino-A.

24. A method of decreasing off-target silencing of inadvertent target mRNA by a siRNA-like duplex, the method comprising:
   (a) identifying an off-target silencing activity mediated by a miRNA* strand of a first siRNA-like duplex, wherein the first siRNA-like duplex directs silencing by a RISC complex of a desired target mRNA; and
   (b) contacting a cell or subject having an RNAi pathway, with a substituted siRNA-like duplex comprising one or more substituted base pairs with respect to the first siRNA-like duplex, wherein the substituted siRNA-like duplex comprises a miRNA strand and a miRNA* strand, each strand having a 5' end and a 3' end, and wherein the substituted siRNA-like duplex directs silencing by the RISC complex of the desired target mRNA, wherein the one or more substituted base pairs are within about 5 base pairs from the 5' end of the miRNA strand (miRNA 5') and the 3' end of the miRNA* strand (miRNA* 3') and are selected from the group consisting of a wobble base pair, a base pair comprising a rare nucleotide, and a base pair comprising a base-modified nucleotide, such that the miRNA* strand of the substituted siRNA-like duplex is less effective than the miRNA* strand of the first siRNA-like duplex at entering the RISC complex;
such that off-target silencing of the inadvertent target mRNA by the substituted siRNA-like duplex is decreased relative to the off-target silencing of the inadvertent target mRNA by the first siRNA-like duplex.

25. The method of claim 14 or 24, wherein the siRNA like duplex silencing agent is derived from an engineered precursor.

26. The method of claim 1, further comprising contacting a cell or subject having an RNAi pathway and an inadvertent target mRNA with the substituted dsRNAi agent produced by step (b) such that silencing of the inadvertent target mRNA in the cell or subject by the substituted dsRNAi agent is decreased relative to silencing of the inadvertent target mRNA by the first dsRNAi agent.

27. The method of claim 14, further comprising
   contacting a cell or subject having an RNAi pathway and an inadvertent target mRNA with the substituted siRNA-like duplex of step (b) such that silencing of the inadvertent target mRNA in the cell or subject by the substituted siRNA-like duplex is decreased relative to silencing of the inadvertent target mRNA by the first dsRNAi agent.

28. The method of claim 11 or 14, wherein the one or more substituted base pairs comprise at least one mismatched base pair.

29. The method of claim 28, wherein the mismatched base pair is selected from the group consisting of G:A, C:A, C:T, C:U, G:G, A:A, C:C, U:T, and U:U.

30. The method of claim 11 or 14, wherein the one or more substituted base pairs comprise at least one wobble base pair.

31. The method of claim 30, wherein the wobble base pair is selected from the group consisting of a G:U or G:T.

32. The method of claim 11 or 14, wherein the one or more substituted base pairs comprise at least one base pair comprising a rare nucleotide.

33. The method of claim 32, wherein the rare nucleotide is inosine (I).

34. The method of claim 32, wherein the base pair is selected from the group consisting of an I:A, I:U and I:C.

35. The method of claim 11 or 14, wherein the one or more substituted base pairs comprise at least one base pair comprising a base-modified nucleotide.

36. The method of claim 35, wherein the base-modified nucleotide is selected from the group consisting of 2-amino-G, 2-amino-A, 2,6-diamino-G, and 2,6-diamino-A.

* * * * *

UNITED STATES PATENT AND TRADEMARK OFFICE
CERTIFICATE OF CORRECTION

PATENT NO. : 7,750,144 B2
APPLICATION NO. : 10/912440
DATED : July 6, 2010
INVENTOR(S) : Phillip D. Zamore et al.

Page 1 of 1

It is certified that error appears in the above-identified patent and that said Letters Patent is hereby corrected as shown below:

In the Claims:

At column 129, claim number 16, line number 56 of the printed patent, "The method of claim 14" should read --The method of claim 15--.

Signed and Sealed this
Twenty-third Day of October, 2012

David J. Kappos
*Director of the United States Patent and Trademark Office*

(12) EX PARTE REEXAMINATION CERTIFICATE (8761st)

United States Patent
Zamore et al.

(10) Number: US 7,750,144 C1
(45) Certificate Issued: Dec. 13, 2011

(54) METHODS AND COMPOSITIONS FOR ENHANCING THE EFFICACY AND SPECIFICITY OF RNA SILENCING

(75) Inventors: Phillip D. Zamore, Northboro, MA (US); György Hutvágner, Worcester, MA (US); Dianne Schwarz, Westborough, MA (US); Martin Simard, Deschambault (CA)

(73) Assignee: The United States of America as represented by the Department of Health and Human Services, Washington, DC (US)

Reexamination Request:
No. 90/011,124, Jul. 30, 2010

Reexamination Certificate for:
Patent No.: 7,750,144
Issued: Jul. 6, 2010
Appl. No.: 10/912,440
Filed: Aug. 4, 2004

Related U.S. Application Data

(63) Continuation-in-part of application No. 10/859,321, filed on Jun. 2, 2004.
(60) Provisional application No. 60/575,268, filed on May 28, 2004, provisional application No. 60/507,928, filed on Sep. 30, 2003, and provisional application No. 60/475,331, filed on Jun. 2, 2003.

(51) Int. Cl.
*C07H 21/00* (2006.01)
*C07H 21/02* (2006.01)
*C07H 21/04* (2006.01)
*C12P 19/34* (2006.01)

(52) U.S. Cl. ............... 536/25.3; 435/95.1; 536/23.1; 536/24.5

(58) Field of Classification Search ............... 536/25.3
See application file for complete search history.

(56) References Cited

To view the complete listing of prior art documents cited during the proceeding for Reexamination Control Number 90/011,124, please refer to the USPTO's public Patent Application Information Retrieval (PAIR) system under the Display References tab.

*Primary Examiner* — Sharon Turner

(57) ABSTRACT

The present invention provides methods of enhancing the efficacy and specificity of RNA silencing. The invention also provides compositions for mediating RNA silencing. In particular, the invention provides siRNAs, siRNA-like molecules, shRNAs, vectors and transgenes having improved specificity and efficacy in mediating silencing of a target gene. Therapeutic methods are also featured.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-36 is confirmed.

* * * * *